(12) United States Patent
Schneider et al.

(10) Patent No.: US 11,986,445 B2
(45) Date of Patent: *May 21, 2024

(54) NUTRITIONAL COMPOSITION AND INFANT FORMULA FOR PROMOTING MYELINATION OF THE BRAIN

(71) Applicant: SOCIÉTÉ DES PRODUITS NESTLÉ S.A., Vevey (CH)

(72) Inventors: Nora Schneider, Epalinges (CH); Jonas Hauser, Lausanne (CH); Sean Deoni, Providence, RI (US); Tamas Bartfai, Stockholm (SE)

(73) Assignee: Societe des Produits Nestle S.A., Vevey (CH)

( * ) Notice: Subject to any disclaimer, the term of this patent is extended or adjusted under 35 U.S.C. 154(b) by 425 days.

This patent is subject to a terminal disclaimer.

(21) Appl. No.: 16/061,063

(22) PCT Filed: Dec. 13, 2016

(86) PCT No.: PCT/EP2016/080772
§ 371 (c)(1),
(2) Date: Jun. 11, 2018

(87) PCT Pub. No.: WO2017/102712
PCT Pub. Date: Jun. 22, 2017

(65) Prior Publication Data
US 2019/0254994 A1    Aug. 22, 2019

Related U.S. Application Data

(60) Provisional application No. 62/328,062, filed on Apr. 27, 2016, provisional application No. 62/315,224, (Continued)

(30) Foreign Application Priority Data

Dec. 14, 2015  (EP) .................................... 15199752
Dec. 14, 2015  (EP) .................................... 15199757
Dec. 14, 2015  (EP) .................................... 15199758
Dec. 14, 2015  (EP) .................................... 15199764
Dec. 14, 2015  (EP) .................................... 15199769

(51) Int. Cl.
| | |
|---|---|
| *A61K 31/14* | (2006.01) |
| *A23L 33/00* | (2016.01) |
| *A23L 33/10* | (2016.01) |
| *A23L 33/12* | (2016.01) |
| *A23L 33/15* | (2016.01) |
| *A23L 33/16* | (2016.01) |
| *A61K 31/20* | (2006.01) |
| *A61K 31/201* | (2006.01) |
| *A61K 31/202* | (2006.01) |
| *A61K 31/519* | (2006.01) |
| *A61K 31/683* | (2006.01) |
| *A61K 31/685* | (2006.01) |

(Continued)

(52) U.S. Cl.
CPC .............. *A61K 31/14* (2013.01); *A23L 33/10* (2016.08); *A23L 33/12* (2016.08); *A23L 33/15* (2016.08); *A23L 33/16* (2016.08); *A23L 33/30* (2016.08); *A23L 33/40* (2016.08); *A61K 31/20* (2013.01); *A61K 31/201* (2013.01); *A61K 31/202* (2013.01); *A61K 31/519* (2013.01); *A61K 31/683* (2013.01); *A61K 31/685* (2013.01); *A61K 31/688* (2013.01); *A61K 31/714* (2013.01); *A61K 33/06* (2013.01); *A61K 33/26* (2013.01); *A61K 33/30* (2013.01); *A61P 3/02* (2018.01); *A23V 2002/00* (2013.01)

(58) Field of Classification Search
CPC ....... A23V 2002/00; A61P 3/02; A23L 33/10; A23L 33/40; A23L 33/30; A23L 33/15; A23L 33/12; A23L 33/16; A61K 31/14; A61K 31/519; A61K 31/714; A61K 313/26; A61K 31/202; A61K 31/688; A61K 33/30; A61K 31/685; A61K 33/06; A61K 31/683; A61K 31/201; A61K 31/20
See application file for complete search history.

(56) References Cited

U.S. PATENT DOCUMENTS

| | | | |
|---|---|---|---|
| 2005/0175759 A1* | 8/2005 | Singhal | ................... A23L 33/40 426/590 |
| 2007/0031537 A1* | 2/2007 | Secretin | ............... A61K 31/202 426/61 |

(Continued)

FOREIGN PATENT DOCUMENTS

| | | | |
|---|---|---|---|
| CN | 101316521 A | 12/2008 | |
| CN | 102046028 A | 5/2011 | |
| WO | WO-2010139702 A2 * | 12/2010 | ............. A23L 33/40 |

OTHER PUBLICATIONS

Georgieff "Nutrition and the developing brain: nutrient priorities and measurement" American Journal of Clinical Nutrition, 2007, vol. 85, pp. 614S-620S.

(Continued)

*Primary Examiner* — Sean M Basquill
(74) *Attorney, Agent, or Firm* — K&L Gates LLP

(57) ABSTRACT

A synthetic nutritional composition comprising choline for use to promote, support or optimise de novo myelination, in particular the de novo myelination trajectory, and/or brain structure, and/or brain connectivity, and/or intellectual potential and/or cognitive potential and/or learning potential and/or cognitive functioning in a subject, in particular a formula fed subject.

9 Claims, 49 Drawing Sheets

Related U.S. Application Data filed on Mar. 30, 2016, provisional application No. 62/315,187, filed on Mar. 30, 2016, provisional application No. 62/315,238, filed on Mar. 30, 2016, provisional application No. 62/315,249, filed on Mar. 30, 2016, provisional application No. 62/315,198, filed on Mar. 30, 2016.

(51) Int. Cl.
*A61K 31/688* (2006.01)
*A61K 31/714* (2006.01)
*A61K 33/06* (2006.01)
*A61K 33/26* (2006.01)
*A61K 33/30* (2006.01)
*A61P 3/02* (2006.01)

(56) References Cited

U.S. PATENT DOCUMENTS

| | | |
|---|---|---|
| 2007/0203235 A1 | 8/2007 | Rosales et al. |
| 2009/0318394 A1 | 12/2009 | Nauroth et al. |
| 2012/0171178 A1 | 7/2012 | Fleith et al. |
| 2014/0065259 A1 | 3/2014 | Koenig et al. |

OTHER PUBLICATIONS

Prado et al. "Nutrition and brain development in early life" Nutrition Reviews, 2014, vol. 72, No. 4, pp. 267-284.

Brochure Entitled "Infant Formal Milk (Stage 1)" Mintel, Jul. 2014, 4 pages.

Holmes-Mc-Nary et al. "Choline and choline esters in human and rat milk and in infant formulas" American Journal of Clinical Nutrition, 1996, vol. 64, pp. 572-576.

Nyaradi et al. "The role of nutrition in children's neurocognitive development, from pregnancy through childhood" Frontiers in Human Neuroscience, Mar. 2013, vol. 7, article 97, pp. 1-16.

Colombo et al., "Long-chain polyunsaturated fatty acid supplementation in infancy reduces heart rate and positively affects distribution of attention", Pediatric research, vol. 70, Issue No. 4, 2011, pp. 406 to 410.

Russian Office Action for Appl No. 2018110560/10(016369) dated Dec. 19, 2020.

Zeisel, "Nutrition in Pregnancy: the Argument for Including a Source of Choline", International Journal of Women's Health, vol. 5, Apr. 20, 2013, pp. 193-199.

Caudill et al., "Pre- and Postnatal Health: Evidence of Increased Choline Needs", Journal of the American Dietetic Association, vol. 110, Issue No. 8, 2010, pp. 1198-1206.

Jiang et al., "Maternal Choline Supplementation: a Nutritional Approach for Improving Offspring Health?", Trends in Endocrinology and Metabolism, vol. 25, Issue No. 5, May 2014, pp. 263-273.

Martinez et al., "MRI Evidence that Docosahexaenoic Acid Ethyl Ester Improves Myelination in Generalized Peroxisomal Disorders", American Academy of Neurology, vol. 51, Issue No. 1, Jul. 1998, pp. 26-32.

Chinese Office Action for Appl No. 2016800072958.9 dated Nov. 19, 2020.

Krysin, "Explanatory Dictionary of Foreign Words", Russian Academy of Sciences, 2006, 4 Pages.

Russia Patent Office Action Received for Application No. 2018125688, mailed on Apr. 14, 2020, 13 pages.

\* cited by examiner

NUTRITIONAL COMPOSITION AND INFANT FORMULA FOR PROMOTING MYELINATION OF THE BRAIN

CROSS REFERENCE TO RELATED APPLICATIONS

The present application is a National Stage of International Application No. PCT/EP2016/080772, filed on Dec. 13, 2016, which claims priority to European Patent Application No. 15199752.5, filed on Dec. 14, 2015, European Patent Application No. 15199757.4, filed on Dec. 14, 2015, European Patent Application No. 15199758.2, filed on Dec. 14, 2015, European Patent Application No. 15199764.0, filed on Dec. 14, 2015, European Patent Application No. 15199769.9, filed on Dec. 14, 2015, U.S. Provisional Patent Application No. 62/315,187, filed on Mar. 30, 2016, U.S. Provisional Patent Application No. 62/315,198, filed on Mar. 30, 2016, U.S. Provisional Patent Application No. 62/315,224, filed on Mar. 30, 2016, U.S. Provisional Patent Application No. 62/315,238, filed on Mar. 30, 2016, U.S. Provisional Patent Application No. 62/315,249, filed on Mar. 30, 2016, and U.S. Provisional Patent Application No. 62/328,062, filed on Apr. 27, 2016, the entire contents of which are being incorporated herein by reference.

FIELD OF THE INVENTION

The present invention relates to a composition for use to promote, support or optimise de novo myelination, and/or brain structure, and/or brain connectivity, and/or one or more of cognitive potential, learning potential, and intellectual potential, and/or cognitive functioning in a subject.

BACKGROUND TO THE INVENTION

Breast-feeding is recommended for all infants. However, in some cases breast-feeding is insufficient or not possible for medical reasons. In these situations infant formula can be used as an alternative to mother's milk. However, studies have shown that infant formula does not always induce identical effects on the body as mother's milk.

In a recent study it was demonstrated that the brain structure, in particular the amount and/or temporal-spatial distribution of myelinated matter throughout the brain, of exclusively breastfed infants can differ from infants fed infant formula, and that these differences can be correlated with enhanced intelligence, learning, and/or cognitive functioning in the breastfed infants, in particular in later life, even when confounding factors are accounted for ("Breast-feeding and early white matter development: a cross sectional study", Deoni et al, NeuroImage 82, (2013), 77-86). Said study also clearly demonstrates that there is an association, in particular a temporal association, between de novo myelination, and in particular the de novo myelination trajectory and brain structure.

Previously longitudinal structural studies of the brains of breastfed and formula fed infants were not available and identified differences in cognitive functioning and ability were often merely attributed to factors such as socio economic status and a mother's educational status. Possible differences in the brain structure of breastfed and formula fed infants were neither considered nor measurable in the manner that is now possible since the MRI of infant brains has become practice cf. Deoni et al.

The relevance of brain structure, in particular the amount and/or spatial distribution of myelinated matter throughout the brain, for cognitive functioning and intelligence is well documented. In itself myelin in the brain provides an insulating sheet along neurons permitting much faster conduction of nerve impulses. However, it is brain structure, in particular the amount and/or spatial distribution of myelin throughout the brain, that affects brain connectivity e.g. via what pathway and how quickly and efficiently, messages in the form of neural impulses are communicated within the brain and in particular between different brain regions. This interbrain communication can play a role in cognitive functioning and learning, and may affect or even may serve to physiological limit intellectual, cognitive and/or learning potential and to regulate cognitive functioning.

Accordingly, there is a need to find ways to promote, support or optimise de novo myelination, in particular the de novo myelination trajectory, and/or brain structure, in particular the amount and/or spatial distribution of myelinated matter throughout the brain, and/or brain connectivity in a subject, in particular a formula fed subject.

In addition there is a need to find ways to optimise intellectual potential and/or cognitive potential and/or learning potential and/or cognitive functioning in a subject, in particular a formula fed subject.

Surprisingly the inventors have now found that a composition comprising choline may promote, support or optimise de novo myelination, in particular the de novo myelination trajectory, and/or brain structure, in particular the amount and/or spatial distribution of myelinated matter throughout the brain, in a subject, in particular a formula fed subject.

More particularly the inventors have found that a composition comprising choline may promote, support or optimise de novo myelination, in particular the de novo myelination trajectory, and/or brain structure, in particular the amount and/or spatial distribution of myelinated matter throughout the brain, in a subject fed infant formula, and may bring one or more of the above more in line or closer to those observed in a breastfed, more particularly exclusively breastfed, subject.

This finding stems from the nutritional analysis of the results of a longitudinal cognitive and brain imaging study wherein de novo myelination, in particular the de novo myelination trajectory, and/or brain structures, in particular the amount and spatial distribution of myelinated matter throughout the brain, in particular as determined by de novo myelination and the de novo myelination trajectory, of breastfed and infant formula fed subjects were examined and compared. Further details of this study and the results are given in the examples included herein.

SUMMARY OF THE INVENTION

The invention is set out in the claims and in further detail in the detailed description included herein.

The present invention encompasses a synthetic nutritional composition comprising choline that may be used to promote, support or optimise one or more of the following:
- de novo myelination, in particular the de novo myelination trajectory,
- brain structure, in particular the amount and spatial distribution of myelinated matter throughout the brain, and/or in specific brain regions,
- brain connectivity,
- intellectual potential,
- cognitive potential,
- learning potential,
- cognitive functioning in a subject, in particular a formula fed subject. More particularly said subject may be a human infant or child, and even more particularly a formula fed human infant or child.

Said synthetic nutritional composition may be a composition selected from the group consisting of; an infant formula, a growing up milk, a composition for infants that is intended to be added or diluted with human breast milk, and a food stuff intended for consumption by an infant and/or child either alone or in combination with human breast milk.

Said composition may optimises the de novo myelination trajectory in a subject, in particular a formula fed subject, and brings it closer, by any amount, to the mean de novo myelination trajectory observed for breast fed subjects, in particular exclusively breastfed subjects, in the brain as a whole or in one or more brain area, when compared to a composition wherein all other components are the same with the exception of the choline content.

Said composition may additionally comprise one or more of the following ingredients:
  A phospholipid, in particular a phospholipid of formula (I) or a mixture of compounds of formula (I) as defined herein, and more particularly may be phosphatidylcholine, phosphatidylinositole, phosphatidylserine, phosphatidylethanolamine, sphingomyelin, or a mixture thereof,
  A vitamin, in particular vitamin B12 and/or folic acid,
  A mineral, in particular iron, zinc, copper, calcium, phosphorus, magnesium and any combination thereof,
  A fatty acid derivative wherein, said fatty acid derivative is a compound comprising a fatty acid, other than a phospholipid, wherein said fatty acid derivative may be selected from the group consisting of a free fatty acid, a monoacylglycerol, a diacylglycerol, a triacylgylcerol, a cholesterol ester and a combination thereof, and wherein said fatty acid may comprise docosahexaenoic acid and/or arachidonic acid and/or stearic acid and/or nervonic acid.

If the composition additionally comprises one or more of these ingredients it may be more effective.

Particularly beneficial concentration for the above mentioned ingredients are set out in the claims and in the detailed description included herein.

DETAILED DESCRIPTION

Figure 1:
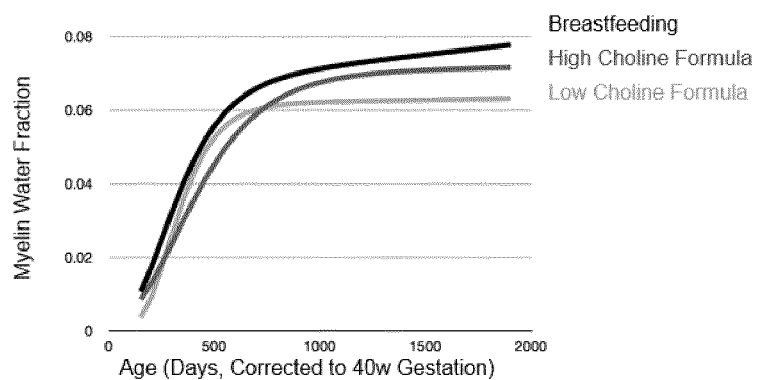
FIG. 1—Shows the mean whole brain (all white matter) myelination trajectories in infants and young children breastfed vs fed with two commercial formulas comprising different levels of choline.

In an aspect of the present invention there is provided a synthetic composition comprising choline, the composition may be for use to promote support or optimise de novo myelination, in particular the de novo myelination trajectory, and/or brain structure, and/or brain connectivity, and/or intellectual potential and/or cognitive potential and/or learning potential, and/or cognitive functioning in a subject, in particular a formula fed subject.

By promoting, supporting and/or optimising de novo myelination, in particular the de novo myelination trajectory, and/or brain structure, in particular the amount and spatial distribution of myelinated matter throughout the brain, in particular as determined by de novo myelination and the de novo myelination trajectory, and/or the intellectual potential and/or cognitive potential and/or learning potential, and/or cognitive functioning in a subject, in particular in a formula fed subject, the composition of the present invention may prevent, reduce the risk and/or mitigate a sub-optimal de novo myelination, in particular a sub-optimal de novo myelination trajectory, and/or a sub-optimal brain structure, and/or sub-optimal brain connectivity, and/or a sub-optimal intellectual potential and/or a sub-optimal cognitive potential and/or a sub-optimal learning potential and/or sub-optimal cognitive functioning in said subject. This may be nontherapeutic or therapeutic.

The term "promote" as used herein refers to a factor or a number of factors causing a certain process to occur.

The term "support" as used herein refers to a factor or a number of factors sustaining a certain process once it has started to occur.

The term subject as used herein refers to a mammal, in particular a cat, dog or human, more particularly the term refers to a human, even more particularly a human infant or child and even more particularly still a human infant or child fed infant formula and/or growing up milk.

The term "infant" as used herein refers to a human infant of up to 12 months of age and includes preterm and very preterm born infants, infants having a low birth weight i.e. a new born having a body weight below 2500 g (5.5 pounds) either because of preterm birth or restricted fetal growth, and infants born small for gestational age (SGA) i.e. babies with birth weights below the 10th percentile for babies of the same gestational age.

The term "child" as used herein refers to a human of 1 to 18 years of age, more specifically a human of 1 to 10 years of age, even more specifically a human of 1 to 5 years of age, and even more specifically a human of 1 to 2 years of age.

The term "formula fed infant or child" as used herein refers to an infant or child fed either infant formula and/or growing up milk.

The term "breastfed subject" as used herein refers to a mammal, in particular a cat, dog or human, more particularly the term refers to a human, even more particularly a human infant or child and even more particularly still a human infant or child, fed human breastmilk, in particular from a nutritionally replete mother.

The term "de novo myelination" as used herein refers to development myelination and in particular the process by which naked axons in the brain of a subject are myelinated during growth and development. It is a process that starts, in particular in specific brain regions, in utero and continues post natally, and that is most prolific in the of a human subject's life, in particular the first 2 or 3 years of a human's life, more particularly the first year of a human's life.

The term "de novo myelination trajectory" as used herein refers to the extent of denovo myelination, or the accumulation of new myelin (as measured for example by the Myelin Water Fraction) as a function of time, and in particular in and across infancy and childhood, in particular early childhood, and more particularly in the first 5 years of a human subject's life, more particularly the first 2 or 3 years of a human's life, even more particularly the first year or first 6 months of a human's life when infant formula may be the sole form of nutrition for some infants.

The term "brain structure" as used herein refers to the structure of grey and white matter within the brain and specific brain regions, and in particular to myelinated white matter within the brain and specific brain regions as determined by de novo myelination and in particular the de novo myelination trajectory i.e. by the de novo structural deposition of myelin. More particularly the term refers to the amount and/or spatial distribution of myelinated matter throughout the brain, and/or in specific brain regions, and even more particularly the amount and/or temporal spatial distribution of myelinated matter throughout the brain and/or in specific brain regions.

The term "intellectual potential" as used herein refers to the possible intellectual ability or capacity attainable by a subject as determined by physiological factors. In particular intellectual potential may refer to fluid intelligence.

The term "fluid intelligence" as used herein refers to a subject's neural potential and/or a subject's novel or abstract problem solving capability as determined by physiological factors. This is distinct from crystallized intelligence which is determined, at least in part by learned or acculturated knowledge.

The term "cognitive potential" as used herein refers to the possible cognitive and/or mental ability or capacity possibly attainable by a subject as determined by physiological factors. In particular the term may refer to one or more of; information processing potential, perception potential, attention potential, thinking potential, reasoning potential, understanding and remembering potential, psychomotor potential including gross motor and fine motor potential, visual potential including visual reception potential, auditory potential, language potential including expressive and receptive language potential, memory and recall potential, concentration potential, executive function potential including problem-solving, decision-making and inhibition potential.

The term "learning potential" as used herein refers to the possible ability or capacity a subject has to learn e.g. how easily and/or quickly a subject may be able to acquire knowledge or skills through experience, study or being taught, as determined by physiological factors. As well as the possible ability a subject has to adapt in response to environmental factors, as determined by physiological factors.

The term "Learning" as used herein refers to the acquisition of knowledge or skills through experience, study, or by being taught.

The term "cognition" as used herein refers to the intellectual processes by which one individual becomes aware of, perceives, or comprehends ideas; thus, the ability to think and understand.

Cognition includes all aspects of information processing, perception, attention, thinking, reasoning, understanding and remembering as well as psychomotor, language, memory, concentration, executive functions and problem-solving abilities.

The term "optimise" as used herein refers to an improvement or enhancement.

Since human breastmilk is the gold standard when it comes to infant nutrition, the de novo myelination trajectory measured or observed in breastfed, more particularly exclusively breastfed subjects, in particular of well-nourished or nutritionally replete mothers, may be considered optimal. A composition of the invention may therefore be considered to optimise a subject's myelination trajectory if it brings a subject's, in particular formula fed subject's, de novo myelination trajectory in line or closer to that measured or observed in a breastfed, more particularly exclusively breastfed subject, in particular of a well-nourished or nutritionally replete mother.

A subject's de novo myelination trajectory may be considered to be in line or closer to that measured or observed in a breastfed, more particularly exclusively breastfed subject, in particular of a well-nourished or nutritionally replete mother, if the distance between any equivalent/same measurement points on the subject's trajectory and said breastfed subject's trajectory is up to 50%, in particular up to 25%, more particularly up to 20%. Non limiting examples within the range of up to 50% include, 50%, 40%, 30%, 25%, 20%, 10%, 5%, 1%, 0.5%, and 0.01%. In particular the trajectories will be considered bioequivalent.

The myelination trajectory can be measured at any combination of time points. In particular the time points are within the first 5 years of a human's life, more particularly the first 2 or 3 years of a human's life, even more particularly in the first year or first 6 months of a human's life.

The de novo myelination trajectory may be determined by measuring any marker of myelination repeatedly over time in a subject. In particular the denovo myelination trajectory may be measured by measuring the myelin associated water fraction (myelin water fraction) and/or the myelin associated water pool (myelin water pool) in a subject at different times points, in particular at different time points across the first 5 years of a human subject's life, more particularly the first 2 or 3 years of a human's life, even more particularly the $1^{st}$ year or first 6 months of a human's life. The myelin associated water fraction and/or the myelin associated water pool in a subject may be measured using a multicomponent relaxation (MCR) magnetic resonance imaging (MRI) technique and in particular using the mcDESPOT technique (Deoni et al 2008). In particular the de novo myelination trajectory may be determined by repeatedly measuring the myelin associated water pool using the mcDESPOT technique over time (Magn.Reson.Med.2008 60:1372-1387 the subject matter of which is hereby incorporated by reference).

A composition of the invention may be considered to optimise a subject's cognitive functioning and/or intelligence if it brings one or more subjects', in particular a formula fed subject's, scores in a standardized cognitive test including intelligence test, school performance test and/or on a neurodevelopmental test, for example on the Mullen Scales of Early Learning, in line or closer to that measured or observed in a breastfed, more particularly exclusively breastfed subject, in particular of a well-nourished or nutritionally replete mother. A subject's cognitive and neurodevelopmental functioning may be considered to be in line or closer to that measured in said breastfed subject, if the difference between one or more of said subject's standardized neurodevelopmental test scores, for example Mullen's T scores, and that of said breastfed subject is less than one standard deviation, more particularly less than half a standard deviation of a standardized test score, for example less than 10 points, more particularly less than 5 points for the Mullen's T score, in particular less than 2 points. Said standardized neurodevelopmental test scores, for example Mullen's T scores, being measured at the same time point in said subject and said breastfed subject.

Said Mullen's score can be measured at any appropriate time point and in particular within the first 5 years, 3 years of a human's life, more particularly the first 2 years of a human's life, even more particularly in the first year or first 6 months of a human's life.

In promoting supporting or optimising cognitive potential, learning potential and/or intellectual potential, the compositions of the invention may have a short term or long term effect on cognitive functioning, including the development of cognitive functions, and/or learning, and on preventing or minimising any neuro cognitive deficits, impairment or delay.

Said short term effect may only be apparent in days, weeks, or months.

Said long term effect may only be apparent in years e.g. 1, 2, 3, 4, 5, 6, 7, 8, 9, 10, 20, 30, 40, 50, 60. 70, 80, 90 years.

A composition comprising choline may be particularly effective at supporting, promoting or optimising de novo myelination, in particular the de novo myelination trajectory, and/or brain structure, in the following brain areas; cerebellum, visual cortex, thalamus, parietal cortex, and frontal lobe. These brain areas are associated with motor function (including coordination and execution of movement), vision, working memory and/or executive functioning and/or social-emotional reasoning and/or spatial reasoning. Accordingly, a composition comprising choline may be particularly effective at promoting, supporting or optimising motor function potential (including coordination and execution of movement potential) and/or psychomotor potential, vision potential, working memory potential, and/or executive functioning potential, and/or social-emotional reasoning potential, and/or spatial reasoning potential.

In an embodiment of the invention cognitive potential is selected from the group consisting of motor function potential (including coordination and execution of movement potential) and/or psychomotor potential, vision potential, working memory potential, executive functioning potential, social-emotional reasoning potential, and spatial reasoning potential.

In promoting supporting or optimising-motor function potential (including coordination and execution of movement potential), vision potential, working memory potential, and/or executive functioning potential, and/or social-emotional reasoning potential, and/or spatial reasoning potential, the compositions of the invention may have a short term or long term effect e.g. enhancement effect on-motor and psychomotor function (including coordination and execution of movement), and/or vision, and/or working memory, and/or executive functioning, and/or social-emotional reasoning, and/or spatial reasoning. Said short term effect may only be apparent in days, weeks, or months.

Said long term effect may only be apparent in years e.g. 1, 2, 3, 4, 5, 6, 7, 8, 9, 10, 20, 30, 40, 50, 60. 70, 80, 90 years.

The term "choline" identifies quaternary ammonium salts containing the N,N,N-trimethylethanolammonium cation and having the structure shown below:

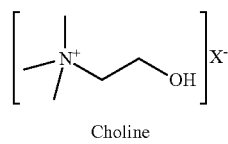

Choline

Counterion $X^-$ may in particular be chloride, hydroxide, citrate, bitartrate and mixtures thereof.

Unless stated otherwise, within the context of the present invention, the term "choline" should be intended to identify all the choline present in the nutritional composition of the invention, in free form (or as a salt thereof).

Choline may be comprised in the composition of the invention in an amount up to 99.999% of the composition.

In particular choline may be comprised in the composition in an amount higher than 30 mg/100 g the dry the composition.

In an embodiment, the composition according to the present invention comprises choline in an amount selected from the group consisting of; higher than 30 mg, higher than 50 mg, higher than 100 mg, higher than 111 mg, higher than 170 mg, ranging from 30 and 1000 mg, ranging from 30 to 700 mg, ranging from 50 and 1000 mg, ranging from 50 to 700 mg, ranging from 50 and 500 mg, ranging from 100 to 400 mg, ranging from 111 to 180, ranging from 170 mg to 300 mg wherein all weights are per 100 g of the dry composition.

In an embodiment, the composition according to the present invention comprises levels of choline in free form (or as a salt thereof) or as derived from structures comprising it such that the total daily intake derived from the nutritional composition of the invention will not exceed 1 g.

Choline may be incorporated in the composition of the invention as such or in the form of one physiologically acceptable salt such as, for example: choline chloride, choline citrate, choline bitartrate or mixtures thereof.

It may be particularly beneficial if the composition of the invention further comprises one or more of the following ingredient: vitamins and/or minerals and/or phospholipids and/or fatty acid derivatives.

When the composition of the invention comprises a choline and one or more of these ingredients it may have an improved effect in terms of promoting supporting and/or optimising de novo myelination, in particular the de novo myelination trajectory, and/or brain structure, and/or brain connectivity, and/or cognitive potential, and/or intellectual potential, and/or learning potential and/or cognitive functioning in a subject, in particular a formula fed subject. This may for example be because said ingredients effect de novo myelination in the same and/or separate complementary brain areas. The improved effect may be synergistic.

In an embodiment the composition of the invention further comprises a vitamin and/or a mineral and/or a phospholipid and/or a fatty acid derivative.

The term vitamin as used herein refers to any vitamin. Non limiting examples of vitamins include: vitamin A, vitamin B1, vitamin B2, vitamin B6, vitamin K, vitamin C, vitamin D, niacin, biotin, pantothenic acid, folic acid, vitamin B12, and combinations thereof.

Particularly effective vitamins may be folic acid, vitamin B12 and vitamin B6, in particular folic acid and vitamin B12, in particular folic acid.

In an embodiment of the invention the vitamin is vitamin B12, folic acid and/or a combination thereof.

A vitamin may be comprised in a composition of the invention in an amount up to 99.999% of the composition.

Folic acid may be comprised in the composition of the invention in an amount up to 99.999% of the composition.

In particular folic acid may be comprised in an amount of higher than 50 mcg/100 g of the dry composition, more particularly 50 mcg to 500 mcg/100 g of the dry composition.

In an embodiment the composition of the invention comprises folic acid in an amount selected from the group consisting of; higher than 50 mcg, higher than 65, higher than 70 mcg, higher than 100 mcg, higher than 110 mcg, higher than 160, ranging from 50 to 500 mcg, ranging from 50 to 400 mcg, ranging from 70 to 170 mcg, ranging from 110 to 500 mcg, ranging from 110 to 400 mcg, ranging from 110 to 400 mcg, ranging from 110 to 350 mcg, wherein all weights are per 100 g of the dry composition.

In an embodiment, the composition according to the present invention comprises an amount of folic acid such that the total daily intake derived from the nutritional composition of the invention will not exceed 400 mcg.

Folic acid may be incorporated in the nutritional compositions of the invention as such or in the form of a physiologically acceptable salt thereof (folate) or mixtures thereof.

Vitamin B12 may be comprised in the composition of the invention in an amount up to 99.999% of the composition.

In particular vitamin B12 may be comprised in the composition in an amount of selected from the group consisting of; higher than 0.01 mcg, in particular higher than 0.04 mcg, in particular higher than 0.05 mcg, wherein all weights are/100 g of the dry composition.

In an embodiment the composition of the invention comprises vitamin B12 in an amount selected from the group consisting of; higher than 0.01 mcg, higher than 0.5 mcg, higher than 0.7, higher than 5 mcg, ranging from 0.1 to 10 mcg, 0.4 to 5 mcg, 0.5 to 2 mcg, 1 to 1.5 mcg, 4 to 8.5 mcg, ranging from 5 to 8 mcg, wherein all weights are per 100 g of the dry composition.

In an embodiment, the composition according to the present invention comprises an amount of vitamin B12 such that the total daily intake derived from the nutritional composition of the invention will not exceed 7.6 mcg/100 g of the dry composition (77.6 mcg/Kg of the dry composition).

Vitamin B12 may be incorporated in the nutritional compositions of the invention as such or in the form of a physiologically acceptable salt thereof or mixtures thereof, or via any source comprising vitamin B12. In particular vitamin B12 may be incorporated into the composition in its pure form, as cyanocobalamin, hydroxocobalamin, and any combination thereof.

A composition comprising a vitamin, in particularly folic acid and/or vitamin B12, may be particularly effective at supporting, promoting or optimising de novo myelination, in particular the de novo myelination trajectory, and/or brain structure in one or more of the following brain areas; cerebellum, visual cortex, motor and somatosensory cortices. These brain areas are associated withMotor function (including coordination and execution of movement), visual function and psychomotor function.

The term mineral as used herein refers to any mineral. Non limiting examples of minerals include: iron, zinc, calcium, phosphorus, copper, magnesium iodine, manganese, chloride, potassium, sodium, selenium, chromium, and combinations thereof. Minerals are usually added in salt form.

Particularly effective minerals may be iron, zinc, calcium, phosphorus, copper, and magnesium, in particular iron.

In an embodiment the composition of the invention comprises iron and/or zinc and/or calcium and/or phosphorus and/or copper and/or and magnesium, in particular iron and zinc, more particularly iron.

In an embodiment, the nutritional composition according to the present invention comprise Iron. Iron may be comprised in the composition of the invention in an amount constituting up to 99.999% of the composition.

In particular iron may be comprised in the composition in an amount higher than 5 mg/100 g of the dry composition.

In an embodiment, the composition according to the present invention comprise Iron in an amount selected from the group consisting of; higher than 4 mg, higher than 9 mg, ranging from 5 to 40 mg, ranging from 9 to 40 mg, ranging from 5 and 20 mg, ranging from 9 to 20 mg, ranging from 5 to 15 mg, ranging from 9 to 15 mg, ranging from 3.5 to 7 mg, wherein all weights are per 100 g of the dry composition.

Iron may be incorporated in the compositions of the invention in the form of one physiologically acceptable salt such as, for example: ferric citrate, ferric phosphate, ferric pyrophosphate, ferrous ascorbate, ferrous carbonate, ferrous citrate, ferrous fumarate, ferrous gluconate, ferrous lactate, ferrous sulfate or mixtures thereof.

Iron may be incorporated in the composition of the invention in the form of a physiologically acceptable iron complex (such as for example EDTA ferric sodium salt) or mixtures thereof.

Fe2+ is more bioavailable and it may therefore be more beneficial if iron is added into the composition in the form of a ferrous salt or complex e.g. a ferrous salts listed hereinabove.

In an embodiment, the composition according to the present invention comprises levels of iron such that the total daily intake derived from the nutritional composition of the invention will not exceed 40 mg.

In an embodiment, the nutritional composition according to the present invention comprise zinc. Zinc may be comprised in the composition of the invention in an amount constituting up to 99.999% of the composition.

In particular zinc may be comprised in the composition in an amount higher than 0.08 mg, higher than 0.3 mg, higher than 0.5 mg, wherein all weights are/100 g of the dry composition.

In an embodiment, the composition according to the present invention comprises zinc in an amount selected from the group consisting of; ranging from 0.5 to 8 mg, 2 to 5.5 mg, 2.5 to 4.5 mg, 3 to 4 mg, 4 to 7.5 mg, 6 to 7.5 mg, wherein all weights are per 100 g of the dry composition.

In an embodiment, the composition according to the present invention comprises levels of zinc such that the total daily intake derived from the nutritional composition of the invention will not exceed 302.4 mg/day, or will not exceed 245 mg/day, or will not exceed 166 mg/day, or will not exceed 98.9 mg/day, or will not exceed 95.6 mg/day.

Zinc may be incorporated in the compositions of the invention in the form of a physiologically acceptable salt such as, for example: zinc nitrate, zinc sulfate, zinc gluconate, zinc acetate or mixtures thereof, or in the form of a physiologically acceptable zinc complex (such as for example zinc picolinate) or mixtures thereof.

In an embodiment, the composition according to the present invention comprises copper. Copper may be comprised in the composition of the invention in an amount up to 99.999% of the composition.

In particular copper may be comprised in the composition in an amount higher than 10 mcg, higher than 40 mcg, higher than 60 mcg, wherein all weight are/100 g dry weight of the composition.

In an embodiment, the composition according to the present invention comprises copper in an amount selected from the group consisting of; higher than 100 mcg, ranging from 100 to 850 mcg, 180 to 650 mcg, 200 to 400 mcg, 210 to 300 mcg, 210 to 240 mcg, 450 to 850 mcg, 800 to 840 mcg, wherein all weights are per 100 g of the dry composition.

In an embodiment, the composition according to the present invention comprises levels of copper such that the total daily intake derived from the nutritional composition of the invention will not exceed 1426 mcg/day, or will not exceed 488 mcg/day.

Copper may be incorporated in the composition of the invention as such or in the form of a physiologically acceptable salt and/or via any source comprising copper, more specifically Cu2+. For example copper may be incorporated into the composition as: copper sulfate and/or copper gluconate and/or copper carbonate, and/or copper citrate, and/or copper-lysine complex.

In an embodiment, the composition according to the present invention comprises magnesium. Magnesium may be comprised in the composition of the invention in an amount up to 99.999% of the composition.

In particular magnesium may be comprised in the composition in an amount higher than 0.2 mg, higher than 0.35 mg, higher than 0.5 mg, wherein all weights are/100 g dry weight of the composition.

In an embodiment, the composition according to the present invention comprises magnesium in an amount selected from the group consisting of; ranging from 0.35 to 90 mg, ranging from 25 to 70 mg, 30 to 65 mg, 35 to 60 mg, 40 to 50 mg, 35 to 55 mg, wherein all weights are per 100 g of the dry composition.

In an embodiment, the composition according to the present invention comprises levels of magnesium such that the total daily intake derived from the nutritional composition of the invention will not exceed 110 mg/day, or will not exceed 65 mg/day.

Magnesium may be incorporated in the composition of the invention as such or in the form of a physiologically acceptable salt and/or via any source comprising magnesium, more specifically Mg2+. For example magnesium carbonate, magnesium chloride, magnesium oxide, magnesium sulphate, magnesium gluconate, magnesium hydroxide, magnesium salts of citric acid, magnesium salts of orthophosphoric acid.

In an embodiment, the composition according to the present invention comprises calcium. Calcium may be comprised in the composition of the invention in an amount up to 99.999% of the composition.

In particular calcium may be comprised in the composition in an amount higher than 0.84 mg. higher than 2.52 mg, higher than 4.62 mg, wherein all weights are/100 g dry weight of the composition.

In an embodiment, the composition according to the present invention comprises calcium in an amount selected from the group consisting of; ranging from 84 to 760 mg, ranging from 200 to 550 mg, ranging from 250 to 450 mg, ranging from 280 to 520, 350 to 650 mg, wherein all weights are per 100 g of the dry composition.

In an embodiment, the composition according to the present invention comprises levels of calcium such that the total daily intake derived from the nutritional composition of the invention will not exceed 482 mg/day, or will not exceed 477 mg/day.

Calcium may be incorporated in the composition of the invention as such or in the form of a physiologically acceptable salt and/or via any source comprising calcium, more specifically Ca2+. For example calcium carbonate, calcium chloride, calcium salts of citric acid, calcium gluconate, calcium glycerophosphate, calcium lactate, calcium hydroxide, calcium salts of orthophosphoric acid.

In an embodiment, the composition according to the present invention comprises phosphorus. Phosphorus may be comprised in the composition of the invention in an amount up to 99.999% of the composition.

In particular phosphorus may be comprised in the composition in an amount higher than 1.7 mg, higher than 14.3 mg, higher than 27.3 mg/100 g dry weight of the composition.

In an embodiment, the composition according to the present invention comprises phosphorus in an amount selected from the group consisting of; ranging from 17 to 516 mg, ranging from 129 to 400 mg, ranging from 140 to 390 mg, ranging from 150 to 370 mg, 160 to 365 mg, ranging from 270 to 350 mg, 200 to 360 mg, wherein all weights are per 100 g of the dry composition.

In an embodiment, the composition according to the present invention comprises levels of phosphorus such that the total daily intake derived from the nutritional composition of the invention will not exceed 863 mg/day, or will not exceed 787 mg/day.

Phosphorus may be incorporated in the composition of the invention as such or in the form of a physiologically acceptable salt and/or via any source comprising phosphorus for example: calcium phosphate, calcium hydrogen phosphate.

A composition comprising a mineral, in particular one or more of iron, zinc, copper, calcium, magnesium and phosphorus, may be particularly effective at supporting, promoting or optimising de novo myelination, in particular the de novo myelination trajectory, and/or brain structure, in one or more of the following brain areas; Cerebellum, visual cortex, motor and somatosensory cortices, corpus callosum, frontal cortex, temporal white matter, internal capsule, prefrontal cortex, motor cortex. These brain areas are associated withMotor function (including coordination and execution of movement), visual function, hemispherical interaction, executive functioning, working memory, problem solving, social-emotional functioning, language, auditory function, problem solving, and/or working memory.

In an embodiment the composition of the invention comprises a phospholipid a metabolic precursor or metabolite thereof.

The term "phospholipid" as used herein refers to any phospholipid, and in particular a compound of formula (I)

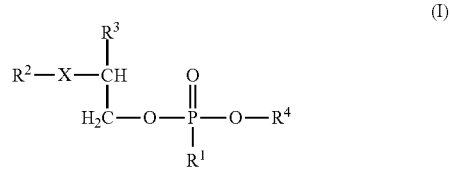

(I)

Wherein,
R$^1$ is O,
X is NH or O
R$^2$ is a C2-C44 saturated or unsaturated, linear or branched acyl group;
R$^3$ is a substituent of formula (II) or formula (III)

(II)

-continued

(III)

Wherein, $R^5$ is a C2-C44 saturated or unsaturated, linear or branched acyl group and $R^6$ is a C2-C44 saturated alkyl or alkenyl group; and $R^4$ is selected from; a C5 or C6 substituted or unsubstituted cyclic alkyl or alkenyl group, or, —(CH2)n-$R^7$, wherein n is an integer ranging from 1 to 4, in particular 1 to 2 and $R^7$ is —N(CH3), NH3, or a substituent of formula (IV) and,

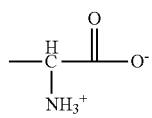

(IV)

in particular $R^4$ is a C6 cyclic alkyl or alkenyl group substituted with one or more hydroxy groups, more particular $R^4$ is derived from inositol (C6H12O6), and even more particularly myo-inositol e.g. $R^4$ is:

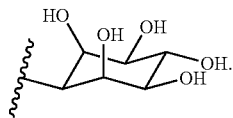

Non limiting examples of phospholipids include phosphatidylinositole, phosphatidylserine, phosphatidylethanolamine, sphingomyelin and phosphatidylcholine.

In an embodiment of the present invention the phospholipid is selected from the group consisting of; phosphatidylcholine, phosphatidylinositole, phosphatidylserine, phosphatidylethanolamine, sphingomyelin and/or combinations thereof.

Phosphatidylinositole is a compound of formula (V)

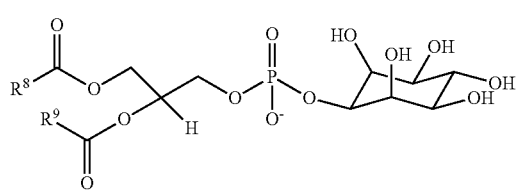

(V)

Wherein $R^8$ is a C2 to C43 branched or unbranched acyclic alkyl, or acyclic alkenyl group and, $R^9$ is a C2 to C43 branched or unbranched acyclic alkyl, or acyclic alkenyl group.

More particularly $R^8$ and $R^9$ are, independently of each other, C13 to C43 branched or unbranched acyclic alkyl, or acyclic alkenyl groups which together with their adjacent carbonyl groups correspond to C14 to C44 saturated or unsaturated fatty acid residues, and even more particularly $R^8$ and $R^9$ are, independently of each other, C13 to C23 branched or unbranched acyclic alkyl, or acyclic alkenyl groups which together with their adjacent carbonyl group correspond to C14 to C24 saturated or unsaturated fatty acid residues.

More particularly, $R^8$ and $R^9$ are C13 to C23 branched or unbranched acyclic alkyl, or acyclic alkenyl groups which together with their adjacent carbonyl group are C14 to C24 saturated or unsaturated fatty acid residues, wherein the fatty acids from which the fatty acid residues stem are selected from the group consisting of; C14:0, C15:0, C16:0, C18:0, C20:0, C20:3, C20:4, C21:0, C22:0, C23:0, C24:0, C18:1n-9, C18:2n-6, and C24:1n-9. Even more particularly C18:0, C18:1n-9, C18:2, C20:3, and C20:4.

As the skilled person would appreciate. The term Phosphatidylserine as used herein refers to Phosphatidyl-L-serine.

Phosphatidylserine is a compound of formula (VI)

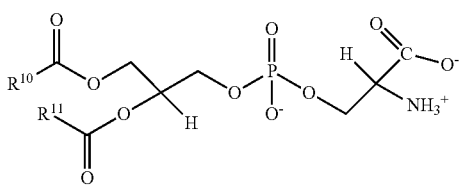

(VI)

(VI)

Wherein $R^{10}$ is a C2 to C43 branched or unbranched acyclic alkyl, or acyclic alkenyl group and, $R^{11}$ is a C2 to C43 branched or unbranched acyclic alkyl, or acyclic alkenyl group. More particularly, $R^{10}$ and $R^{11}$ are, independently of each other, C13 to C43 branched or unbranched acyclic alkyl, or acyclic alkenyl groups which together with their adjacent carbonyl groups correspond to C14 to C44 saturated or unsaturated fatty acid residues, and even more particularly $R^{10}$ and $R^{11}$ are, independently of each other, C13 to C23 branched or unbranched acyclic alkyl, or acyclic alkenyl groups which together with their adjacent carbonyl group correspond to C14 to C24 saturated or unsaturated fatty acid residues.

More particularly, $R^{10}$ and $R^{11}$ are C13 to C23 branched or unbranched acyclic alkyl, or acyclic alkenyl groups which together with their adjacent carbonyl group are C14 to C24 saturated or unsaturated fatty acid residues, wherein the fatty acids from which the fatty acid residues stem are selected from the group consisting of; C14:0, C15:0, C16:0, C18:0, C20:0, C20:3, C20:4, C21:0, C22:0, C23:0, C24:0, C18:1n-9, C18:2n-6, and C24:1n-9. Even more particularly C18:0, C18:1n-9, C20:4, and C22:6.

Phosphatidylethanolamine is a compound of formula (VII)

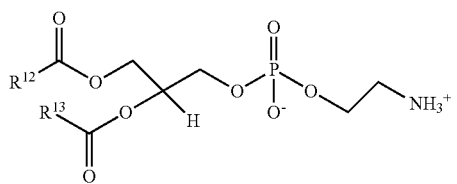

(VII)

Wherein $R^{12}$ is a C2 to C43 branched or unbranched acyclic alkyl, or acyclic alkenyl group and, $R^{13}$ is a C2 to C43 branched or unbranched acyclic alkyl, or acyclic alkenyl group. More particularly, $R^{12}$ and $R^{13}$ are, independently of each other, C13 to C43 branched or unbranched acyclic alkyl, or acyclic alkenyl groups which together with their adjacent carbonyl groups correspond to C14 to C44 saturated or unsaturated fatty acid residues, and even more particularly $R^{12}$ and $R^{13}$ are, independently of each other, C13 to C23 branched or unbranched acyclic alkyl, or acyclic alkenyl groups which together with their adjacent carbonyl group correspond to C14 to C24 saturated or unsaturated fatty acid residues.

The term "sphingomyelin" as used herein refers to a lipid molecule, or mixture of lipid molecules, wherein a sphingosine or sphinganine backbone is esterified with a fatty acid residue at the amino group (—NH2) through an amide bond and wherein the hydroxyl group at position 1 of the sphingosine backbone is linked to a phosphorylcholine moiety.

In a particular sphingomyelin is a compound of formula (VIII) or a mixture of compounds of formula (VIII)

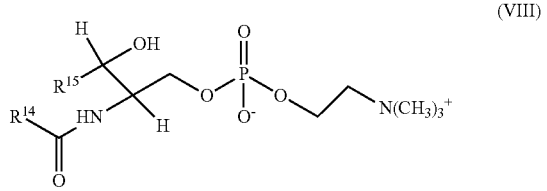

Wherein $R^{14}$ is a C2 to C43 branched or unbranched acyclic alkyl, or acyclic alkenyl group, $R^{15}$ is a C2 to C43 branched or unbranched acyclic alkyl, or acyclic alkenyl group.

More particularly, $R^{14}$ is a C13 to C43 branched or unbranched acyclic alkyl, or acyclic alkenyl group which together with the adjacent carbonyl group corresponds to a C14 to C44 saturated or unsaturated fatty acid residue.

Non limiting examples of C14 to C44 saturated or unsaturated fatty acids from which the fatty acid residue may stem include; C14:0, C15:0, C16:0, C18:0, C20:0, C21:0, C22:0, C23:0, C24:1, C25:0, C28:1, C30:2, C30:1, C30:0, C32:3, C32:2, C32:1, C32:0, C33:1, C34:3, C34:2, C34:1, C34:0, C35:2, C35:0, C36:4, C36:3, C36:2, C36:1, C36:0, C37:1, C37:0, C38:4, C38:3, C38:1, C38:0, C39:1, C39:0, C40:2, C40:1, C40:0, C41:2, C41:1, C41:0, C42:47, C42:3, C42:2, C42:1, C42:0, C44:3, C44:1.

Even more particularly, $R^{14}$ is a C13 to C23 branched or unbranched acyclic alkyl, or acyclic alkenyl group which together with the adjacent carbonyl group corresponds to a C14 to C24 saturated or unsaturated fatty acid residue, wherein the fatty acid from which the fatty acid residue stemmed is selected from the group consisting of; C14:0, C15:0, C16:0, C18:0, C20:0, C21:0, C22:0, C23:0, C24:0, C18:1n-9, C18:2n-6, and C24:1n-9.

Even more particularly still, sphingomyelin is a mixture of compounds of formula (VIII) wherein the mixture is such that the total number of fatty acid residues ($R^{14}$ together with the adjacent carbonyl group) comprised in the mixture are predominately saturated fatty acids, and the least predominant are unsaturated fatty acids. More particularly the mixture will be such that that 80% to 96% of said fatty acid residues in the mixture are saturated fatty acids, in particular C14, C15, C16, C18, C20, C22, C23, C24 saturated fatty acids more particularly C16, C18, C20, C22 and C24.

Phosphatidylcholine is a compound of formula (IX)

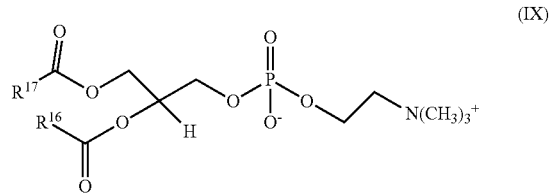

Wherein $R^{16}$ is a C2 to C43 branched or unbranched acyclic alkyl, or acyclic alkenyl group and, $R^{17}$ is a C2 to C43 branched or unbranched acyclic alkyl, or acyclic alkenyl group.

More particularly, $R^{16}$ and $R^{17}$ are, independently of each other, C13 to C43 branched or unbranched acyclic alkyl, or acyclic alkenyl groups which together with their adjacent carbonyl groups correspond to C14 to C44 saturated or unsaturated fatty acid residues, and even more particularly $R^{16}$ and $R^{17}$ are, independently of each other, C13 to C23 branched or unbranched acyclic alkyl, or acyclic alkenyl groups which together with their adjacent carbonyl group correspond to C14 to C24 saturated or unsaturated fatty acid residues.

More particularly, $R^{16}$ and $R^{17}$ are C13 to C23 branched or unbranched acyclic alkyl, or acyclic alkenyl groups which together with their adjacent carbonyl group are C14 to C24 saturated or unsaturated fatty acid residues, wherein the fatty acids from which the fatty acid residues stem are selected from the group consisting of; C14:0, C15:0, C16:0, C16:1, C18:0, C20:0, C20:1, C20:3, C20:4, C21:0, C22:0, C22:6, C23:0, C24:0, C18:1n-9, C18:2n-6, and C24:1n-9. Even more particularly C14:0, C16:0, C18:0, C18:1n-9, C18:2n-6, C20:1, C20:3, C20:4, and C22:6.

A phospholipid, a metabolic precursor and/or metabolite thereof may be comprised in a composition in an amount up to 99.999% of the composition.

In particular sphingomyelin, a metabolic precursor and/or metabolite thereof may be comprised in a composition in an amount up to 99.999% of the composition.

More particularly the composition will comprise sphingomyelin in an amount higher than 200 mg/kg of the dry weight of the composition, more particularly ranging from 200 mg to 2.5 g/kg of the dry weight of the composition.

In an embodiment the composition comprises sphingomyelin in an amount selected from the group consisting of; higher than 200 mg/kg, higher than 300 mg/kg, ranging from 200 mg to 2.5 g/kg, ranging from 200 mg to 2 g/kg, in amount ranging from 300 mg to 1.5 g/kg or from 400 mg to 1 g/Kg, ranging from 200 to 850 mg/kg, or 300 to 820 mg/kg. All weights being per dry weight of the composition.

In particular phosphatidylcholine, a metabolic precursor and/or metabolite thereof may be comprised in a composition in an amount up to 99.999% of the composition.

More particularly the composition will comprise phosphatidylcholine in an amount higher than 200 mg/kg of the dry weight of the composition, more particularly ranging from 200 mg to 2.5 g/kg of the dry weight of the composition.

In an embodiment the composition comprises phosphatidylcholine in an amount selected from the group consisting of; higher than 200 mg/kg, higher than 300 mg/kg, higher than 400 mg/kg, ranging from 200 mg to 2.5 g/kg, ranging from 200 mg to 2 g/kg, in amount ranging from 300 mg to 1.5 g/kg or from 400 mg to 1 g/Kg, 500 to 1.3 g/kg. All weights being per dry weight of the composition.

In particular phosphatidylinositole, a metabolic precursor and/or metabolite thereof may be comprised in a composition in an amount up to 99.999% of the composition.

More particularly the composition will comprise phosphatidylinositole in an amount higher than 50 mg/kg of the dry weight of the composition, more particularly ranging from 200 mg to 1.5 g/kg of the dry weight of the composition.

In an embodiment the composition comprises phosphatidylinositole in an amount selected from the group consisting of; higher than 200 mg/kg, higher than 300 mg/kg, ranging from 200 mg to 2.5 g/kg, ranging from 200 mg to 2 g/kg, in amount ranging from 250 mg to 800 mg/kg or from 400 mg to 1.5 g/Kg or from 400 mg to 800 mg/Kg. All weights being per dry weight of the composition.

In particular phosphatidylserine, a metabolic precursor and/or metabolite thereof may be comprised in a composition in an amount up to 99.999% of the composition.

More particularly the composition will comprise phosphatidylserine in an amount higher than 50 mg/kg of the dry weight of the composition, higher than 200 mg/kg of the dry weight of the composition, more particularly ranging from 150 mg to 1.5 g/kg of the dry weight of the composition, from 200 mg to 1 g/kg of the dry weight of the composition.

In an embodiment the composition comprises phosphatidylserine in an amount selected from the group consisting of; higher than 150, higher than 200 mg/kg, higher than 300 mg/kg, ranging from 200 mg to 2.5 g/kg, ranging from 200 mg to 2 g/kg, in amount ranging from 250 mg to 1000 mg/kg or from 400 mg to 1 g/Kg. All weights being per dry weight of the composition.

In particular phosphatidylethanolamine, a metabolic precursor and/or metabolite thereof may be comprised in a composition in an amount up to 99.999% of the composition.

More particularly the composition will comprise phosphatidylethanolamine in an amount higher than 150 mg/kg of the dry weight of the composition, higher than 200 mg/kg of the dry weight of the composition, more particularly ranging from 150 mg to 1.5 g/kg of the dry weight of the composition.

In an embodiment the composition comprises phosphatidylethanolamine in an amount selected from the group consisting of; higher than 170 mg/kg, higher than 180 mg/kg, higher than 200 mg/kg, ranging from 200 mg to 2.5 g/kg, ranging from 200 mg to 2 g/kg, in amount ranging from 250 mg to 800 mg/kg or from 200 mg to 1 g/Kg. All weights being per dry weight of the composition.

In an embodiment the composition of the invention comprises phospholipids including phosphatidylinositole, phosphatidylserine, phosphatidylethanolamine, sphingomyelin and phosphatidylcholine such that the total concentration does not exceed 15.4 g/kg.

If a metabolic precursor and/or metabolite of one or more phospholipid is used in a composition in place of or in combination with a phospholipid, said compounds may be used in amounts such that the level of phospholipids physiologically delivered by said composition is in line with those set out hereinabove. It is well within the purview of the skilled person to determine appropriate amounts.

The term metabolic precursor and/or metabolite of one or more phospholipid as used herein does not include choline.

Non limiting examples of metabolic precursors and/or a metabolite of phospholipids, in particular sphingomyelin, phosphatidylcholine, phosphatidylinositole, phosphatidylserine and/or phosphatidylethanolamine are: galactoceramides, glucoceramides, sphingosine, sphingosine-1-phosphate, ceramide, D-erythro-dihydroceramide and ceramide-1-phosphate and gangliosides.

Particularly effective phospholipids may be phosphatidylcholine, phosphatidylserine, phosphatidylinositol and/or sphingomyelin, in particular sphingomyelin.

In an embodiment of the present invention the phospholipid is phosphatidylcholine, phosphatidylserine, phosphatidylinositol, sphingomyelin and/or a metabolic precursor and/or metabolite of any of the foregoing and/or combinations of any of the foregoing. In particular the phospholipid is sphingomyelin, a metabolic precursor and/or metabolite thereof.

Particularly effective metabolic precursors and/or a metabolite of phospholipids, in particular sphingomyelin may be ceramide and gangliosides and ceramide-1-phosphate and d-erythro-dihydroceramide.

The term "ceramide" indicates a lipid molecule wherein the sphingosine or sphinganine backbone is esterified with a fatty acid residue through an amide bond. When the term ceramide is used in the present specifications, it may identify a single ceramide species as well as a mixture of single ceramide species.

In particular ceramide is a compound of formula (IXa), or a mixture of compounds of formula (IXa)

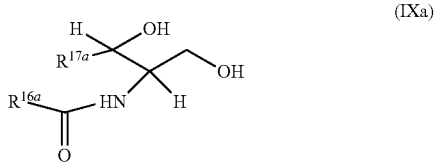

wherein,
$R^{16a}$ is a C2 to C43 branched or unbranched acyclic alkyl, or acyclic alkenyl group,
$R^{17a}$ is a C2 to C43 branched or unbranched acyclic alkyl, or acyclic alkenyl group.

More particularly, $R^{16a}$ is a C13 to C43 branched or unbranched acyclic alkyl, or acyclic alkenyl group which together with the adjacent carbonyl group corresponds to a C14 to C44 saturated or unsaturated fatty acid residue.

Non limiting examples of C14 to C44 saturated or unsaturated fatty acids from which the fatty acid residue may stem include; C14:0, C15:0, C16:0, C18:0, C20:0, C21:0, C22:0, C23:0, C24:1, C25:0, C28:1, C30:2, C30:1, C30:0, C32:3, C32:2, C32:1, C32:0, C33:1, C34:3, C34:2, C34:1, C34:0, C35:2, C35:0, C36:4, C36:3, C36:2, C36:1, C36:0, C37:1, C37:0, C38:4, C38:3, C38:1, C38:0, C39:1, C39:0, C40:2, C40:1, C40:0, C41:2, C41:1, C41:0, C42:47, C42:3, C42:2, C42:1, C42:0, C44:3, C44:1.

Even more particularly, $R^{16a}$ is a C13 to C23 branched or unbranched acyclic alkyl, or acyclic alkenyl group which together with the adjacent carbonyl group corresponds to a C14 to C24 saturated or unsaturated fatty acid residue, wherein the fatty acid from which the fatty acid residue stemmed is selected from the group consisting of; C14:0, C15:0, C16:0, C18:0, C20:0, C21:0, C22:0, C23:0, C24:0, C18:1n-9, C18:2n-6, and C24:1n-9, and more particularly the group consisting of C16:0, C18:0, C20:0, C22:0 and C24:0.

Even more particularly still, ceramide is a mixture of compounds of formula (IXa) wherein the mixture is such that the total number of fatty acid residues ($R^{16a}$ together with the adjacent carbonyl group) comprised in the mixture are predominately saturated fatty acids, and the least predominant are unsaturated fatty acids. More particularly the mixture will be such that that 80% to 96% of said fatty acid residues in the mixture are saturated fatty acids, in particular C14, C15, C16, C18, C20, C22, C23, C24 saturated fatty acids, more particularly C16, C18, C20, C22 and C24.

The term "ganglioside" as used herein indicates an oligoglycosylceramide lipid molecule comprising the residue of a ceramide of formula IXa as defined herein. When the term ganglioside is used in the present specifications, it may identify a single ganglioside species as well as a mixture of single ganglioside species comprising the residue of a ceramide of formula IXa as defined herein.

Particularly effective gangliosides may be monosialoganglioside-3 (GM3) gangliosides and/or disialogangliosides 3 (GD3) gangliosides.

Ceramide-1-phosphate and d-erythro-dihydroceramide with comprise a residue of a ceramide of formula IXa as defined herein.

Gangliosides and/or ceramides and/or Ceramide-1-phosphate and/or d-erythro-dihydroceramide may be comprised in the composition in any amount.

Concentrations in the range of 2-11.5 mg/100 g of GD3 and/or GM3 may be particularly effective.

Sphingomyelin may be synthesised from ceramide and phosphatidylcholine, accordingly, it may be particularly beneficial if ceramide and/or one or more ganglioside is used in combination with phosphatidylcholine a metabolic precursor or metabolite thereof.

The phospholipid, metabolic precursors and/or metabolite thereof, comprised in the composition of the invention may be natural, synthetic or a mixture thereof. Said metabolic precursors and/or a metabolite, may be used in the composition of the invention in their pure form, or substantially pure form. Alternatively, they may be added in the form of a source comprising them.

Any source of a phospholipid metabolic precursors and/or metabolite thereof, suitable for ingestion by a subject for which the composition is intended to be consumed may be used in the invention.

In particular the phospholipid, metabolic precursor, or metabolite thereof, will come from natural sources, non limiting examples of which include, eggs, soy, bovine brains, and/or mammalian milk or extracts thereof. Non limiting examples of soy sources include soy lecithin-food additive, non limiting examples of mammalian milk include bovine, camel, sheep, goat milk including skilled milks. Non limiting extracts of milk include protein extracts e.g. whey protein and casein, milk fat globule membranes (MFGM) and extracts comprising them.

A particularly useful source of a phospholipids a metabolic precursor or metabolite thereof, in particular sphingomyelin, that may be used in the present invention may be a bovine milk whey protein concentrate enriched in alpha-lactalbumin, and/or none pure alpha-lactalbumin which has been extracted from milk whey protein, in particular bovine milk whey protein.

Alpha-Lactalbumin is a high-quality, easy-to-digest e.g. by human infants whey protein and is the primary protein found in HM. Alpha-lactalbumin and/or an alpha-lactalbumin enriched milk fraction is ideal for use in lower protein infant formulas due to its high content of essential amino acids, particularly tryptophan. Although alpha-Lactalbumin is in itself a protein non pure sources may comprise sphingomyelin.

In an embodiment a phospholipid a metabolic precursor or metabolite thereof, in particular sphingomyelin, is used in the form of a whey protein concentrate enriched in alpha-lactalbumin or as alpha-lactalbumin.

In a more particular embodiment, a bovine whey protein concentrate enriched in alpha-lactalbumin or alpha-lactalbumin having a phospholipid content, in particular sphingomyelin content higher than 500 mg/100 g, 900 mg/100 g, 1000 mg/100 g dry weight of the composition is used.

Another particularly useful source of phospholipids a metabolic precursor, or metabolite thereof, may be milk fat globule membrane (hereinafter MFGM) or extracts comprising them, in particular MFGM, or extracts comprising them from bovine milk. It may be particularly beneficial if the MFGM or extracts comprising them comprises at least 1%, 2%, 5%, 10%, 20%, 30%, 40% phospholipids and/or at least 0.1%, 0.2%, 0.5% to 5%, 0.8% to 3%, 1% to 2%, 1.6%, 1.9%, 1.8% of phosphatidylcholine, phosphatidylinositole, phosphatidylserine, phosphatidylethanolamine, and/or sphingomyelin. The MFGM may also further comprise magnesium, phosphorus and or calcium, in particular in concentrations ranging from 0.05% to 2%, 0.1% to 0.4%.

A composition comprising a phospholipid and/or a metabolic precursor and/or a metabolite thereof, in particular sphingomyelin, phosphatidylcholine and/or phosphatidylinositol, may be particularly effective at supporting, promoting or optimising de novo myelination, in particular the de novo myelination trajectory, and/or brain structure, in one or more of the following brain areas; cerebellum, visual cortex, corpus callosum, internal capsule, frontal lobe, parietal lobe, temporal lobe, motor cortex, frontal cortex. These brain areas are associated with one or more of the following: vision, motor function (including coordination and execution of movement), hemispherical interaction, language function, auditory function (including listening and attention), working memory, executive functioning including problem solving, social processing, and behaviour interaction, spatial reasoning, and language.

In an embodiment the composition of the invention comprises a fatty acid derivative.

A fatty acid derivative may be comprised in the composition of the invention in an amount constituting up to 99.999% of the composition.

The term "fatty acid derivative" as used herein refers to a compound comprising a fatty acid, other than a phospholipid, and in particular to a free fatty acid, and/or a monoacylglycerol (hereinafter MAG), and/or a diacylglycerol (hereinafter DAG), and/or a triacylgylcerol (hereinafter TAG) and/or a cholesterol ester. More particularly the term refers to a MAG, DAG, TAG and/or a cholesterol ester. Even more particularly the term refers to a TAG.

The term "MAG" as used herein refers to a glycerol molecule in which one of the OH groups has formed an ester bond with a fatty acid. In particular the term "MAG" as used herein refers to a compound of formula (X)

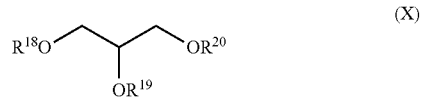

Wherein, two of $R^{18}$ $R^{19}$ or $R^{20}$ are H and wherein one of $R^{18}$ $R^{19}$ or $R^{20}$ is a C4 to C44 saturated or unsaturated acyl group.

More particularly, two of $R^{18}$ $R^{19}$ or $R^{20}$ are H and one of $R^{18}$ $R^{19}$ or $R^{20}$ is a C10 to C24 saturated or unsaturated acyl group, and even more particularly a C14 to C24 saturated or unsaturated acyl group.

The term "DAG" as used herein refers to glycerol molecule in which two of the OH groups have formed an ester bond with two fatty acids. In particular the term "DAG" as used herein refers to a compound of formula (X)

Wherein,
one of $R^{11}$ $R^{19}$ or $R^{20}$ are H and wherein two of $R^{18}$ $R^{19}$ or $R^{20}$ are C4 to C44 saturated or unsaturated acyl group. More particularly C10 to C24 saturated or unsaturated acyl group, and even more particularly C14 to C24 saturated or unsaturated acyl groups. The two C4 to C44 saturated or unsaturated acyl groups of $R^{18}$ $R^{19}$ or $R^{20}$ may be the same or different.

The term "TAG" as used herein refers to glycerol molecule in which three of the OH groups have formed an ester bond with three fatty acids. In particular the term "TAG" as used herein refers to a compound of formula (X)

Wherein,
Wherein all $R^{18}$ $R^{19}$ or $R^{20}$ are C4 to C44 saturated or unsaturated acyl groups, more particularly C10 to C24 saturated or unsaturated acyl groups, and even more particularly C14 to C24 saturated or unsaturated acyl groups. The three C4 to C44 saturated or unsaturated acyl groups may all be the same, all different, or two may be the same and one different.

The term "cholesterol ester" as used herein refers to a compound of formula (XI)

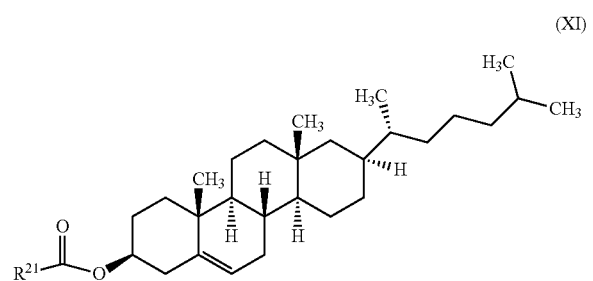

(XI)

Wherein,
$R^{21}$ is a C2 to C43 branched or unbranched acyclic alkyl, or acyclic alkenyl group.

More particularly, $R^{21}$ is a C9 to C43 branched or unbranched acyclic alkyl, or acyclic alkenyl groups which together with their adjacent carbonyl group correspond to C10 to C44 saturated or unsaturated fatty acid residues, and even more particularly a C14 to C24 saturated or unsaturated fatty acid residue.

The term "fatty acid" as used herein refers to a compound of formula (XII)

(XII)

Wherein
$R^{22}$ is a C2 to C43 branched or unbranched acyclic alkyl, or acyclic alkenyl group.

More particularly, $R^{22}$ is a C9 to C43 branched or unbranched acyclic alkyl, or acyclic alkenyl group and even more particularly a C13 to C 23 branched or unbranched acyclic alkyl, or acyclic alkenyl group.

Non limiting examples of C10 to C44 saturated or unsaturated fatty acids that may be comprised in the fatty acid derivative i.e. that may be the free fatty acid or fatty acid from which the fatty acid residue(s) of the MAG, DAG, TAG and/or cholesterol ester may stem include; C10:0, C12:0, C14:0, C15:0, C16:0, C16:1n-7, C18:0, C18:1n-7, C18:1n-9, C18:2n-6, 18:3n-3, C20:0, C20:1n-9, C20:2n-6, C20:3n-6, C20:4n-6, 20:5n-3, C21:0, C22:0, C22:1n-9, C22:6n-3 C23:0, C24:1, in particular 24:1n-9, C25:0, C28:1, C30:2, C30:1, C30:0, C32:3, C32:2, C32:1, C32:0, C33:1, C34:3, C34:2, C34:1, C34:0, C35:2, C35:0, C36:4, C36:3, C36:2, C36:1, C36:0, C37:1, C37:0, C38:4, C38:3, C38:1, C38:0, C39:1, C39:0, C40:2, C40:1, C40:0, C41:2, C41:1, C41:0, C42:47, C42:3, C42:2, C42:1, C42:0, C44:3, C44:1. In particular said fatty acids will be selected from the group consisting of: C10:0, C12:0, C14:0, C16:0, C16:1n-7, C18:0, C18:1n-7, C18:1n-9, C18:2n-6, 18:3n-3, C20:0, C20:1n-9, C20:2n-6, C20:3n-6, C20:4n-6, 20:5n-3, C22:0, C22:1n-9, C22:6n-3, C24:1, 24:1n-.

Any fatty acid derivative suitable for ingestion by a subject for which the composition is intended to be consumed may be used in the invention.

In particular the fatty acid derivative will come from natural sources, non limiting examples of which include, eggs, algae, fish oil, mould, yeast, seeds, plants e.g. soy, and animal sources e.g. bovine brains, and/or mammalian milk or extracts thereof. Non limiting examples of soy sources include soy lecithin-food additive, non limiting examples of mammalian milk include bovine, camel, sheep, goat milk including skilled milks. Non limiting extracts of milk include protein extracts, milk fat globule membranes (MFGM) and extracts comprising them. Fatty acid derivatives may also come from palm oil, tallow, lard, cotton seed oil, peanut oil.

It may be particularly beneficial if the fatty acid derivative comprises a saturated or unsaturated fatty acid selected from the group consisting of: C20:4n-6, C22:6n-3, C24:1n-9, C16:0, C18:1n-9, and C18.0. In particular C20:4n-6 and/or C22:6n-3 and/or C18:0. More particularly 22:6n-3 and/or C18:0.

A composition comprising a phospholipid, in particular sphingomyelin, phosphatidylcholine, phosphatidylserine, phosphatidylinositol, more particularly sphingomyelin, may be particularly effective if used in combination with one or more of these fatty acids.

C20:4n-6 is arachidonic acid (hereinafter ARA or AA). C22:6n-3 is docosahexaenoic acid (hereinafter DHA). 24:1n-9 is nervonic acid. C18.0 is stearic acid. C16:0 is palmitic acid. C18:1n-9 is Oleic acid.

In an embodiment the composition according to the invention comprises a fatty acid derivative comprising DHA and/or ARA and/or nervonic acid and/or stearic acid, in particular a fatty acid derivative comprising DHA and/or ARA and/or Stearic acid. Most particularly a fatty acid derivative comprising DHA and/or Stearic acid.

A fatty acid derivative comprising DHA and/or ARA and/or nervonic acid and/or stearic acid may be comprised in the composition of the invention in an amount constituting up to 99.999% of the composition.

In particular a fatty acid derivative comprising DHA and/or ARA and/or nervonic acid and/or stearic acid, may be comprised in the composition of the invention in an amount of 15 to 350 mg/100 g dry weight of the composition, more particularly 30 mg to 300 mg/100 g dry weight of the composition.

In an embodiment, the composition according to the present invention comprise a fatty acid derivative comprising DHA and/or ARA and/or nervonic acid and/or stearic acid, in an amount selected from the group consisting of; higher than 15 mg/100 g, higher than 30 mg/100 g, higher than 50 mg/100 g, higher than 55 mg/100 g, ranging from 30 to 300 mg/100 g, ranging from 30 to 200 mg/100 g or from 30 to 150 mg/100 g, ranging from 50 to 300 mg/100 g, ranging from 50 to 200 mg/100 g, ranging from 50 to 150 mg/100 g, ranging from 150 to 350, ranging from 60 to 350 mg/100 g, ranging from 60 to 120 mg/100 g, ranging from 100 to 110 mg/100 g. All concentrations are by dry weight of the composition.

Fatty acid derivatives comprising stearic acid are present in natural sources for example palm oil, tallow, lard, cotton seed oil, peanut oil.

Fatty acid derivatives comprising nervonic acid are resent in natural sources for example the seed oils of *Cardamine gracea, Heliphila longifola, Thlaspi perfoliatum, Tropaeolum speciosum, Lunaria biennis, Lunaria annua* and *Malania oleifera*; the moulds *Neocallismastix frontalis, Erysiphe graminis* and *Sphaerotheca humuli*; the bacterium *Pseudomonas atlantica*; the yeast *Saccharomyces cerevisiae* and the marine diatom *Nitzschia cylindrus*.

Fatty acid derivatives comprising DHA and/or ARA are present in natural sources such as for example egg, algae, fungus or fish oil, and in plants.

Oils comprising fatty acid derivatives comprising DHA and/or ARA and generally other polyunsaturated fatty acids (PUFAs), in particular EPA (eicosapentaenoic acid), may be of various origin. Preferably, fatty acid derivatives comprising DHA are provided in the form of a fish oil comprising fatty acid derivatives comprising DHA and/or ARA. Fish oils generally comprise 5 wt. % or more, preferably 10 wt. % or more of fatty acid derivatives comprising DHA and/or ARA. Oils comprising substantial amounts of fatty acid derivatives comprising DHA and/or ARA, obtained from algae or microorganisms in general are also available. For example, oils harvested from algae comprising 10 wt. % or more, for example 20 wt. % or more of fatty acid derivatives, may be used.

If the nutritional composition according to the present invention comprises fatty acid derivatives comprising ARA and DHA. Said ingredients may for example be comprised in the composition of the invention in amounts resulting in a weight ratio of DHA:ARA in the range of 4:1 to 1:4, for example 3:1 to 1:3, for example 2:1 to 1:2, for example 1.5:1 to 1:1.5, in particular 1.1:1 to 1:1.1.

It may also be beneficial if the composition of the invention comprises a mixture of fatty acid derivatives wherein, the mixture is such that the weight ratio of unsaturated to saturated fatty acids and/or fatty acid residues in the composition of the invention is within the range 1:1 to 1:2; 1:1.2 to 1:1.9, 1:1.25 to 1:1.5; 1:3 to 1:4.

Further, when high amounts of fatty acid derivatives comprising DHA and/or ARA are comprised in the composition of the invention, it may be particularly beneficial if the total amount of fatty acid derivatives comprising saturated long chain fatty acids, in particular C20/24 is increased. These saturated long chain fatty acids may be an important component of myelin enabling it to wrap around and enrobe axons. The weight ratio of DHA and/or AA to these saturated long fatty acids in the composition of the invention may for example be within the range 1:1 1:10; 1:2 to 1:9, 1:3 to 1:4.5, 1:3.5 to 1:4.5.

A composition of the invention comprising a fatty acid derivative e.g. a fatty acid derivative comprising DHA and/or AA may be particularly effective at supporting, promoting or optimising de novo myelination, in particular the de novo myelination trajectory, and/or brain structure, in one or more of the following brain areas: cerebellum, internal capsule, parietal lobe, motor and sensory cortices (including coordination and execution of movement), visual cortex, frontal cortices. This brain areas are associated with vision function, motor function and psychomotor function (including coordination and execution of movement function), and/or executive functions, and social-emotional functioning.

The person skilled in the art may identify appropriate amounts of the above mentioned nutrients, metabolic precursors or metabolites thereof based on the nature, purpose, the target subject and the dosage of the composition e.g. how many times per day the composition is to be ingested by the subject. Typically an effective dose will depend on age, size and health status of the subject, on the subject's lifestyle, the amounts of nutrients in the composition, and maybe on the gender of the subject.

An effective dose may be any dose that promotes, supports or optimises de novo myelination, in particular the de novo myelination trajectory, and/or brain structure, and/or brain connectivity, and/or intellectual potential and/or cognitive potential and/or learning potential and/or cognitive functioning in a subject.

For an infant formula or growing up milk, the skilled person may base amounts or ratios of the compounds or nutrients disclosed herein e.g. choline, on those amounts found in human breast milk produced for an infant or child of the same age, in particular by a nutritionally replete mother.

It is well within the purview of the skilled person to determine an effective dose based upon the information herein and the knowledge in the field.

In an embodiment, the composition according to the invention comprises choline, a vitamin, in particular vitamin B12 and/or folic acid, a phospholipid, in particular phosphatidylcholine, and/or phosphatidylserine, and/or phosphatidylinositol, and/or sphingomyelin, and/or a metabolic precursor or metabolite of any of the foregoing, a mineral, in particular iron, and/or zinc, and/or calcium and/or magnesium, and/or phosphorus, and/or copper, and a fatty acid derivative in particular comprising DHA and/or AA and/or nervonic acid and/or stearic acid.

Particularly beneficial concentrations/amounts of said ingredients in said composition may be sphingomyelin in an amount of at least 300 or 420 mg/kg, in particular more than 800 mg/kg and more particularly more than 900 mg/kg, phosphatidylcholine in an amount of at least 1000 mg/kg, phosphatidylserine in an amount of at least 900 mg/kg, phosphatidylinositol in an amount of at least 700 mg/kg, folic acid in amount of at least 140 mg/kg more particularly at least 160 mg/kg, vitamin B12 in amount of at least 2.34 mcg/100 g, in particular more than 5 mcg/100 g, more particularly 7 mcg/100 g, iron in an amount of at least 6 mg/100 g or at least 8.6 mg/100 g more particularly 11.5 mg/100 g, even more particularly more than 16 mg/kg, choline in an amount of at least 124 mg/kg more particularly 140 mg/kg, a fatty acid derivative comprising DHA in an amount of at least 89 mg/100 g, a fatty acid derivative comprising AA in an amount of at least 89 mg/100 g or at least 175 mg/100 g, zinc in an amount of at least 4 or at least 4.7 mg/100 g more particularly 7 mg/100 g, calcium in an amount of at least 200 mg or at least 500 mg/100 g, phosphorus in an amount of at least 140 mg/100 g or at least 350 mg/100 g, copper in an amount of at least 250 mcg/100 g or at least 600 mcg/100 g, magnesium in an amount of at least 30 mg/100 g or at least 50 mg/100 g. Wherein all weights are by dry weight of the composition.

A concentration falling within established error margins for any analytical technique used to measure the concentration of one or more of the above ingredients, should be considered as falling within the concentrations set out herein.

In an embodiment, the composition according to the invention comprises choline, vitamin B12 and/or folic acid, sphingomyelin and/or a metabolic precursor or metabolite thereof, iron, zinc, and a fatty acid derivative comprising DHA and/or AA.

In an embodiment, the composition according to the invention comprises a fatty acid derivative comprising DHA and/or ARA, vitamin B12 and/or folic acid, sphingomyelin and iron. in a more specific embodiment the composition according to the invention comprises a fatty acid derivative comprising DHA in a concentration of 102 mg/100 g, ARA in a concentration of 102 mg/100 g, vitamin B12 in a concentration of 5.4 mcg/100 g, folic acid in a concentration of 169 mcg/100 g, sphingomyelin in a concentration of 81.4 mg/100 g and iron in a concentration of 6.7 mg/100 g.

The composition of the invention may be any type of composition suitable for direct administration to a subject.

In particular the composition will be a synthetic nutritional composition.

The term "nutritional composition" as used herein refers to a synthetic composition that nourishes a subject. This nutritional composition may be taken enterally, parenterally or intravenously. In particular the composition will be taken enterally and more particularly orally.

In an embodiment of the invention said the composition will be a synthetic nutritional composition selected from the group consisting of; growing up milk, infant formula or a composition for infants that is intended to be added or diluted with human breast milk (hereinafter "HM") e.g. HM fortifier, or a food stuff intended for consumption by an infant and/or child either alone or in combination with HM e.g. complementary foods.

The compositions of the invention can also comprise any other ingredients or excipients known to be employed in the type of composition in question e.g. infant formula.

Non limiting examples of such ingredients include: proteins, amino acids, carbohydrates, oligosaccharides, lipids, prebiotics or probiotics, nucleotides, nucleosides, other vitamins, minerals and other micronutrients.

In one typical embodiment of the present invention, the composition will contain a protein source, a lipid source and a carbohydrate source.

For example such a composition may comprise protein in the range of about 2 to 6 g/100 kcal, lipids in the range of about 1.5 to 3 g/100 kcal and/or carbohydrates in the range of about 1.7 to 12 g/100 kcal.

If the composition is liquid, its energy density may be between 60 and 75 kcal/100 ml.

If the composition is solid, its energy density may be between 60 and 75 kcal/100 g.

The type of protein is not believed to be critical to the present invention. However, in the case of synthetic compositions for infants and/or children e.g. infant formula or growing up milks, said protein should support the growth of an infant and/or child so that said infant and/or child may adhere to the growth curves typical for its genetic background, birth weight and health state.

Non limiting examples of proteins include: casein, alpha-lactalbumin, whey, beta lactoglobulin, soy protein, rice protein, corn protein, oat protein, barley protein, wheat protein, rye protein, pea protein, egg protein, sunflower seed protein, potato protein, fish protein, meat protein, lactoferrin, serum albumin, immunoglobins, and combinations thereof.

Non limiting examples of amino acids include leucine, threonine, tyrosine, Isoleucine, arginine, alanine, histidine, isoleucine, proline, valine, cysteine, glutamine, glutamic acid, glycine, serine, arginine, lysine, methionine, phenylalanine, tryptophane, asparagine, aspartic acid, and combinations thereof.

Non limiting examples of carbohydrates include lactose, saccharose, maltodexirin, starch, and combinations thereof.

Non limiting examples of lipids include: palm olein, high oleic sunflower oil, high oleic safflower oil, canola oil, fish oil, coconut oil, bovine milk fat, and combinations thereof.

It may be particularly beneficial if the composition comprises fat in an amount of 25 to 30 g/100 g dry weight of the composition.

Non limiting examples of essential fatty acids include: linoleic acid (LA), α-linolenic acid (ALA). The compositions of the invention may further contain gangliosides monosialoganglioside-3 (GM3) and disialogangliosides 3 (GD3), and combinations thereof.

None limiting examples of prebiotics include: oligosaccharides optionally containing fructose, galactose, mannose; dietary fibers, in particular soluble fibers, soy fibers; inulin; and combinations thereof. Preferred prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof, and combinations of the foregoing.

Further examples of oligosaccharide are described in Wrodnigg, T. M.; Stutz, A. E. (1999) Angew. Chem. Int. Ed. 38:827-828 and in WO 2012/069416 which is incorporated herein by reference. Non limiting examples of probiotics include: *Bifidobacterium, Lactobacillus, Lactococcus, Enterococcus, Streptococcus, Kluyveromyces, Saccharoymces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM I-2618), *Bifidobacterium longum* NCC490 (CNCM I-2170), *Bifidobacterium lactis* NCC2818 (CNCM I-3446), *Bifidobacterium breve* strain A, *Lactobacillus paracasei* NCC2461 (CNCM I-2116), *Lactobacillus johnsonii* NCC533 (CNCM I-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and combinations thereof.

Non limiting examples of Nucleotides include: cytidine monophosphate (CMP), uridine monophosphate (UMP), adenosine monophosphate (AMP), guanosine monophosphate (GMP), and combinations thereof.

Other suitable and desirable ingredients of nutritional compositions that may be employed in the nutritional composition of the invention may be described in guidelines issued by the Codex Alimentarius with respect to the type of nutritional composition in question e.g. Infant formula, HM fortifier, follow on formula, or food stuffs intended for consumption by infants e.g. complementary foods.

In an even more specific embodiment the composition of the invention is an infant formula having the composition set out in example 5 and specifically table 11a.

The synthetic nutritional composition, for example an infant formula, for use in the invention may be prepared in any suitable manner. For example, an infant formula may be prepared by blending together the protein source, the carbohydrate source, and the fat source in appropriate proportions. If used, the emulsifiers may be included in the blend. The choline, any vitamins and any minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger. The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point. The homogenised mixture is transferred to a suitable drying apparatus such as a spray drier or freeze drier and converted to powder. The powder should have a moisture content of less than about 5% by weight. If it is desired to add probiotic(s), they may be cultured according to any suitable method and prepared for addition to the infant formula by freeze-drying or spray-drying for example. Alternatively, bacterial preparations can be bought from specialist suppliers such as Christian Hansen and Morinaga already prepared in a suitable form for addition to food products such as infant formula. Such bacterial preparations may be added to the powdered infant formula by dry mixing.

As evident from the above disclosure, the composition of the invention may be used to promote, support or optimise de novo myelination, in particular the de novo myelination trajectory, and/or brain structure, and/or brain connectivity and/or intellectual potential, and/or cognitive potential and/or learning potential and/or cognitive functioning in a subject, in particular a formula fed subject.

In another aspect of the present invention there is provided a method of promoting, supporting or optimising de novo myelination, in particular the de novo myelination trajectory, and/or brain structure, and/or brain connectivity and/or intellectual potential, and/or cognitive potential and/or learning potential and/or cognitive functioning in a subject, in particular a formula fed subject, said method comprising feeding to said subject a composition comprising choline as defined herein.

In another aspect of the present invention there is provided a composition comprising choline, as defined herein for use in the manufacture of a composition for promoting, supporting or optimising de novo myelination, in particular the de novo myelination trajectory, and/or brain structure, and/or brain connectivity and/or intellectual potential, and/or cognitive potential and/or learning potential and/or cognitive functioning in a subject, in particular a formula fed subject.

It may be particularly beneficial if the composition of the invention is administered to an infant of 9 months of age or less, in particular 6 months of age or less, more particularly 3 months of age or less.

Non limiting examples of an age 3 months of age or less are up to 2 weeks of age, up to 1 month of age, up to 2 months of age, up to 3 months of age, 1 to 3 months of age.

The effects of the composition of the invention described herein may have long term health benefits. Dementia e.g. Alzheimer's disease, causes a decrease in a subject's ability to think and remember, as well as emotional and language problems. The risk of a subject suffering from dementia, in particular Alzheimer's disease has been associated with a person's intellectual ability or intelligence. Accordingly, by optimising a subject's intellectual, cognitive and or learning potential the risk of a subject developing dementia in particular Alzheimer's disease may be reduced. Said long term effect may only be apparent in years e.g. 40, 50, 60. 70, 80, 90 years.

Further, A variety of psychiatric and/or neurological disorders e.g. anxiety, depression, autism and schizophrenia, are linked to brain structure. By promoting, supporting or optimising de novo myelination, in particular the de novo myelination trajectory, and/or brain structure, in particular as determined by de novo myelination and the de novo myelination trajectory, in a subject, it may be that psychiatric and/or neurological disorders e.g. anxiety, depression, autism and schizophrenia are prevented or that the risk of them developing is reduced, or that the severity of said condition(s) is reduced. Said effect may only be apparent in years e.g. 1, 2, 3, 4, 5, 6, 7, 8, 9, 10, 20, 30, 40, 50, 60. 70, 80, 90 years.

All percentages expressed herein are by weight unless otherwise stated.

In the context of the present invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

As will be evident to the skilled person, the same benefits as disclosed herein may be obtainable by taking choline directly as opposed to in the form of a composition. Accordingly, choline may be employed directly in place of the composition of the present invention in any method or use set out herein.

As would be further evident to the skilled person, it may be particularly beneficial if choline is administered i.e. consumed, separately, sequentially and/or simultaneously to one or more of the following ingredient: a vitamin, in particular vitamin B12 and/or folic acid and/or a mineral, in particular iron and/or zinc and/or calcium and/or phosphorus and/or magnesium and/or copper, a fatty acid derivative, in particular a fatty acid derivative comprising docosahexaenoic acid and/or arachidonic acid and/or nervonic acid and/or stearic acid, and/or a phospholipid, in particular phosphatidylcholine, phosphatidylserine, phosphatidylinositol, and/or sphingomyelin.

All particulars of the invention apply equally to the composition comprising choline and to the direct use of choline.

It should be appreciated that all features of the present invention disclosed herein can be freely combined and that variations and modifications may be made without departing from the scope of the invention as defined in the claims. Furthermore, where known equivalents exist to specific features, such equivalents are incorporated as if specifically referred to in this specification.

The terms "in particular" or "more particularly" as used herein should not be considered limiting but should be interpreted as being synonymous with "for example" or "especially".

There now follows a series of non-limiting examples that serve to illustrate the invention.

Experimental Section

Methods, Definitions and Materials

MRI (Magnetic Resonance Imaging): MRI brain scans of infants and children between 0 and 5 years were acquired using a white matter imaging technique. This technique provides a quantitative measure, the Myelin Water Fraction (MWF), which is a surrogate marker of myelin content in the brain. When mapped as a function of time across early childhood, myelination trajectories can be generated.

Infant formula composition: six infant formulas fed to infants participating in a study were analyzed for their composition/level of myelin-relevant nutrients.

Nutritional compositions were tested in standard, commercially-available infant formulas of different brands/suppliers and showing variable levels on the nutrients therein contained.

Cognitive abilities: Age-standardized (T)-scores of gross motor, visual reception and language (expressive and receptive) derived from the Mullen Scales of Early Learning, a standardized and validated measurement tool of early cognitive development for infants and children 6 years of age or younger.

Nutrient Analysis

Nutrients in each of the 6 infant formula compositions are shown in table 1.

TABLE 1

| Nutrient | Unit | Concentration range across the 6 infant formulas included in the analysis |
| --- | --- | --- |
| Alpha Lactalbumin | g/100 g protein | ND-1.01 |
| Fat | g/100 g | 26.3-29.5 |
| AA | mg/100 g | 94.2-180 |
| DHA | mg/100 g | 42.3-89.8 |
| Iron | mg/100 g | 8.42-11.7 |
| Calcium | mg/100 g | 397-566 |
| Phosphorus | mg/100 g | 234-358 |
| Sodium | mg/100 g | 135-189 |
| Potassium | mg/100 g | 593-834 |
| Copper | mcg/100 g | 471-834 |
| Zinc | mg/100 g | 4.23-7.25 |

TABLE 1-continued

| Nutrient | Unit | Concentration range across the 6 infant formulas included in the analysis |
| --- | --- | --- |
| Magnesium | mg/100 g | 38.4-53.9 |
| Magnese | mcg/100 g | 60.6-140.3 |
| Vitamin B12 | mcg/100 g | 4.93-8.34 |
| Folic acid | mcg/100 g | 98.8-306 |
| Choline | mg/100 g | 35.7-170 |
| Beta lactoglobulim | g/100 g | ND-4.21 |
| Phospahtidylcholine | mg/kg | 397-1287 |
| Phosphatidylinositole | mg/kg | 266-788 |
| Phosphatidylserine | mg/kg | <LQ (144)-977 |
| Phosphatidylethanolamine | mg/kg | <LQ(174) |
| Sphingomyelin | mg/kg | <LQ(100)-480 |

Clinical Study

Infant Participants

Infants included in this study were drawn from a larger longitudinal study of normal brain and behavioral development: the Brown University Assessment of Myelination and Behavior Across Maturation (BAMBAM). To focus on neurotypical development, children with known potential risk factors for learning, neurologic, or psychiatric disorders were specifically excluded during recruitment and enrollment. Thus, children with in utero alcohol or illicit substance exposure, premature (<37 weeks gestation) or multiple birth, fetal ultrasound abnormalities, complicated pregnancy (e.g., preeclampsia), APGAR scores <8, NICU admission, neurological disorder (e.g., head injury, epilepsy), psychiatric or developmental disorders in the infant, parents or siblings (including maternal depression requiring medication) were excluded. Ongoing screenings, such as the MCAT for autism, or CBCL for behavioral problems, were further used to remove enrolled children with clinically concerning behaviors or overt medical conditions (such as autism spectrum disorders).

A combination of retrospective and prospective data were acquired from parents via detailed medical histories and parental interview on the type of infant formula used, percentage of breastfeeding to formula feeding, and length of exclusive breastfeeding. This information was updated at each study visit, which occurred approximately every 6 months for children under 2 years, and yearly for older children. Using this information, children were categorized into one of 2 groups: #1. Exclusively formula-fed; and #2. Exclusively breastfed for at least 90 days (3 months). Children who were fed a combination of breastmilk and formula within 3 months were excluded from our analysis. Infants within the exclusively formula-fed group were further sub-divided based on parental reports of the main infant formula used throughout the first 3 months. Main formula was defined as that given 90% of the time or more (in the case were parents used an alternate brand during vacation, for example).

Using these criteria, 94 exclusively formula-fed infants and young children were selected into group #1. These included 13 children who received formula #2; 28 who received formula #5; 8 who received formula #3; 39 who received formula #4; 5 who received formula #1 and 1 who received formula #6. A sample of 52 exclusively breast-fed infants were also selected and matched to the over formula-fed group with regards to mean age, gestation duration, birth weight, male:female ratio, ethnicity ratio, maternal education, family size, and number of languages spoken in the home (in addition to English). Groupings for each formula are provided in Table 1a.

TABLE 1a

Data breakdown for longitudinal and nutritional analysis

| | Formula 1 | Formula 2 | Formula 5 | Formula 3 | Formula 4 | Formula 6 | Breast-fed |
|---|---|---|---|---|---|---|---|
| $N_{children}$ | 5 | 13 | 28 | 8 | 39 | 1 | 52 |
| $N_{Measurements}$ | 11 | 27 | 56 | 14 | 64 | 3 | 106 |

Imaging Methods and Analysis

Each infant was scanned using the mcDESPOT (multi-component Driven Equilibrium Single Pulse Observation of $T_1$ and $T_2$) white matter imaging technique Deoni et al. (Magn. Reson. Med. 2008, 60:1372-1387), which provides a quantitative measure of the myelin water fraction (MWF)—a measure of myelin content—at each point throughout the brain. All infants were scanned during natural (i.e. non-sedated) sleep using acoustically-muffled mcDESPOT imaging protocols. Total imaging times ranged from 19 minutes for the youngest toddlers to 24 minutes for the older 4 year-old children.

All data were acquired on a Siemens 3T Tim Trio scanner equipped with a 12 channel head RF array. To minimize intra-scan motion, children were swaddled with a pediatric MedVac vacuum immobilization bag (CFI Medical Solutions, USA) and foam cushions. Scanner noise was reduced by lessening the peak gradient amplitudes and slew-rates, and using a noise-insulating scanner bore insert (Quiet Barrier HD Composite, UltraBarrier, USA). MiniMuff pediatric ear covers and electrodynamic headphones (MR Confon, Germany) were also used. Children were continuously monitored with a pediatric pulse-oximetry system and infrared camera. All children remained asleep for the duration of the MRI scan and no motion-artifacts were present in the analyzed data.

Following image alignment, non-brain signal removal, and correction for main and transmit magnetic field ($B_0$ and $B_1$) inhomogeneities, a three-pool signal model (comprising the myelin-associated water; intra-extra axonal water; and a non-exchanging free-water pool) was fit to the mcDESPOT data to derive voxel-wise MWF maps.

Each child's map was then non-linearly aligned to a study specific template. White matter masks, corresponding to 5 bilateral regions (frontal, temporal, occipital, parietal, and cerebellar WM) as well as the body, genu, and splenium of the corpus callosum were created from common databases, registered to the common template, and superimposed onto each child's MWF map. Mean values for each region were then determined for each child and used for subsequent developmental analysis and trajectory modeling.

Developmental Differences:

To examine developmental differences between the breastmilk and formula-fed infants, as well as between the different formula-fed infants, a non-linear mixed effects modeling approach was used. Modified Gompertz growth models were fit to groups #1 and #2, and each formula sub-group independently. Each of the four Gompertz model parameters were then compared between the breast and formula-fed groups using an unpaired t-test, and between the 4 formula sub-groups using an analysis of variance followed by post-hoc Tuckey tests to determine which of the formula groups differed.

Cognitive Assessments and Analysis

Alongside MR imaging, general cognitive ability and skills were evaluated in each child within 7 days of scanning using the Mullen Scales of Early Learning, MSEL (Mullen EM, 1995). The MSEL provide a broad assessment of behavioral development in the domains of fine and gross motor control, receptive and expressive language, and visual reception. Age-normalized T-scores from these domains can be combined into three composite scores: the early learning composite (ELC, comprising fine motor, visual reception, expressive and receptive language); the non-verbal development quotient (NVDQ, comprising fine motor and visual reception scores); and the verbal development quotient (VDQ, comprising the expressive and receptive language scores).

As with the MWF MRI data, potential group mean differences in ELC, VDQ and NVDQ between the breast-milk and formula-fed infants, as well as between the different formula sub-groups were examined. In addition to mean comparisons, longitudinal changes in these three composite values were investigated using mixed effects modeling assuming a linear trend.

Example 1

Nutritional Drivers Identification from Cross-Sectional Analyses

From the cohort described above, children up to 5 years of age that were fed different infant formulas during infancy were included in a large correlation analysis to examine the relationship between formula nutrient composition and brain myelination. The 6 most frequently used formulas in that cohort were analyzed for their nutritional composition. A single general linear model (GLM) was constructed that modeled all quantified nutrients and child age.

Spearman rank correlations were then calculated between the nutrient content and myelin content value (adjusted for child age) at each image voxel, or point within the brain. Significance was defined as $p<0.05$ corrected for type 1 error using a cluster based correction approach. An association or trend was defined as $p<0.15$. In initial analysis, inclusion of all 22 nutrients shown in Table 1 resulted in an underpowered model. To reduce the number of nutritional components in the model, we examined the inter-nutritional correlation. Using a conservative threshold of 0.9, we excluded nutritional components that were highly correlated with each other across the various formulas. This yielded a final model that included iron, sphingomyelin, folic acid, choline, DHA, zinc, and phosphatidylcholine.

$P<0.05$: iron, sphingomyelin, folic acid, choline, DHA.
$P<0.15$: zinc, and phosphatidylcholine.

Nutritional components that were found to be highly correlated with each other were: Folic acid and vitamin B12.
DHA and AA.
Zinc, calcium, magnesium, copper, and phosphorus.
Phosphatidylcholine, phosphatidylserine and phosphatidylinositol.

For choline, an association with myelination (myelin water fraction) was observed over time in the brain, in particular in the cerebellum, visual cortex, thalamus, parietal cortex, and frontal lobe. Results are reported in FIG. 1b.

For sphingomyelin, an association with myelination (myelin water fraction) was observed over time in the brain, in particular in the cerebellum, visual cortex, internal capsule, frontal lobe, parietal lobe, temporal lobe. Results are reported in FIG. 1c.

For phosphatidylinositol, an association with myelination (myelin water fraction) was observed over time in the brain, in particular in the cerebellum, visual cortex, motor cortex, frontal cortex. Results are reported in FIG. 1d.

For phosphatidylcholine, an association with myelination (myelin water fraction) was observed over time in the brain, in particular in the cerebellum, visual cortex, internal capsule, frontal lobe, parietal lobe, temporal lobe. Results are reported in FIG. 1e.

For folic acid, an association with myelination (myelin water fraction) was observed over time in the brain, in particular in the cerebellum, motor cortex, visual cortex. Results are reported in FIG. 1f.

For vitamin B12, an association with myelination (myelin water fraction) was observed over time in the brain, in particular in the cerebellum, visual Cortex, Motor & Somatosensory Cortices. Results are reported in FIG. 1g.

For iron, an association with myelination (myelin water fraction) was observed over time in the brain, in particular in the cerebellum, visual cortex, internal capsule, motor & somatosensory cortices, corpus callosum, frontal cortex, temporal white matter. Results are reported in FIG. 1h.

For zinc, an association with myelination (myelin water fraction) was observed over time in the brain, in particular in the cerebellum, visual cortex, internal capsule, motor & somatosensory cortices, corpus callosum, frontal cortex, temporal white matter. Results are reported in FIG. 1i.

For calcium, an association with myelination (myelin water fraction) was observed over time in the brain, in particular in the cerebellum, visual cortex, Motor & Somatosensory Cortices, Corpus Callosum, Frontal Cortex, Temporal White Matter. Results are reported in FIG. 1j.

For phosphorus, an association with myelination (myelin water fraction) was observed over time in the brain, in particular in the cerebellum, visual cortex, motor & somatosensory cortices, prefrontal cortex. Results are reported in FIG. 1k For magnesium, an association with myelination (myelin water fraction) was observed over time in the brain, in particular in the cerebellum, visual cortex, internal capsule, corpus callosum, frontal cortex, motor cortex. Results are reported in FIG. 1l For DHA, an association with myelination (myelin water fraction) was observed over time in the brain, in particular in the cerebellum, primary & secondary motor cortices, internal capsule, visual Cortex, frontal Cortex. Results are reported in FIG. 1m.

For AA, an association with myelination (myelin water fraction) was observed over time in the brain, in particular in the cerebellum, internal capsule, parietal lobe, motor and sensory cortices, visual Cortex, frontal Cortices. Results are reported in FIG. 1n.

Example 2 a) Whole Brain Myelination Trajectory from Longitudinal Study

From the available data, trajectories of longitudinal myelin development (de novo myelination) were calculated using repeated MWF data from children for whose infant formulas contained a differing amount of choline (composition of such formulas is reported below in Table 2).

Trajectories were calculated using a longitudinal nonlinear mixed effects approach. Modified Gompertz growth models were fitted to the data of children for each formula group. Results are reported in FIG. 1.

TABLE 2

|  | (low choline content) | (high choline content) |
|---|---|---|
| Choline | 35.7 mg/100 g | 170 mg/100 g | b) Mean Regional Brain Myelination Trajectory from Longitudinal Study

From the available data, a mean regional trajectory of longitudinal myelin development (de novo myelination) was calculated using repeated MWF data from children for whose infant formulas contained a differing amount of choline (composition of such formulas is reported below in Table 2a). Trajectories were calculated using a longitudinal nonlinear mixed effects approach and modified Gompertz growth models were fitted to the data of children for each formula group. Results are reported in FIG. 1a.

TABLE 2a

|  | (low choline content) | (high choline content) |
|---|---|---|
| Choline | 111 mg/100 g | 170 mg/100 g |

Figure 1A:
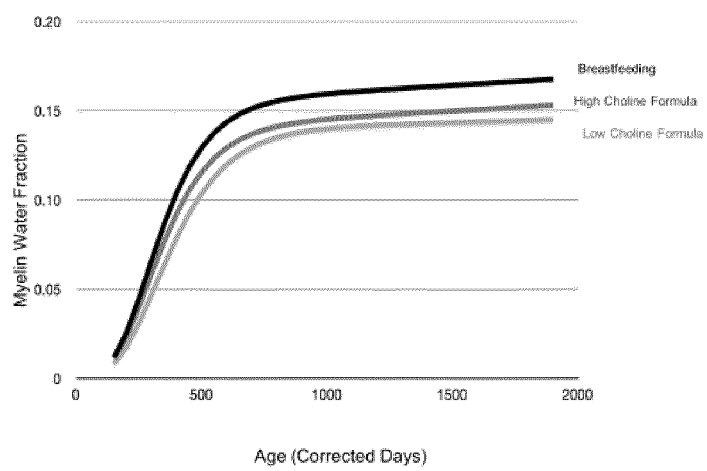
FIG. 1a—Shows the mean regional myelination trajectories in infants and young children breastfed vs fed with two commercial formulas comprising different levels of choline.
Figure 1B:
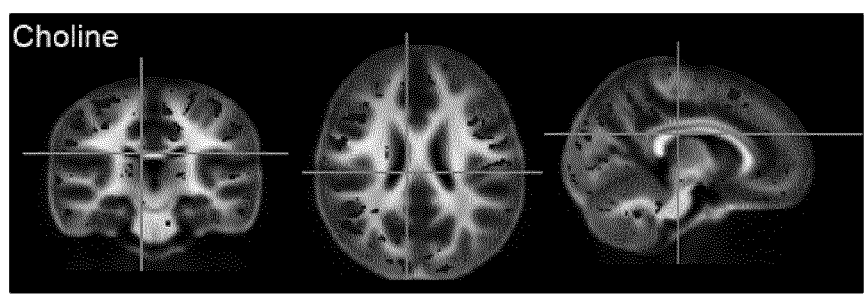
FIG. 1b—Is a brain image showing the myelinated brain regions associated with choline.
Figure 1C:
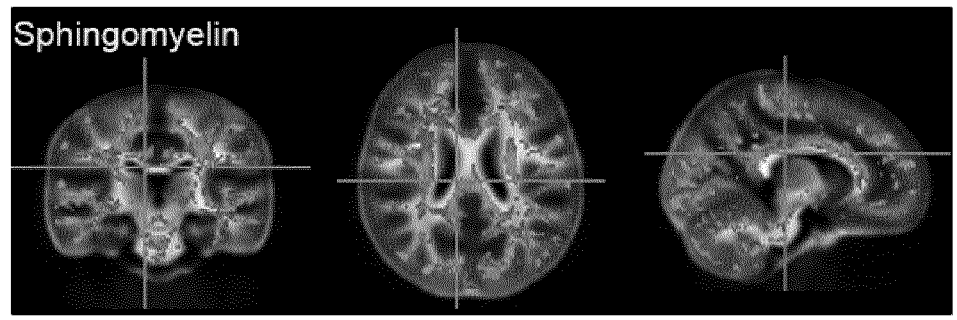
FIG. 1c—Is a brain image showing the myelinated brain regions associated with sphingomyelin.
Figure 1D:
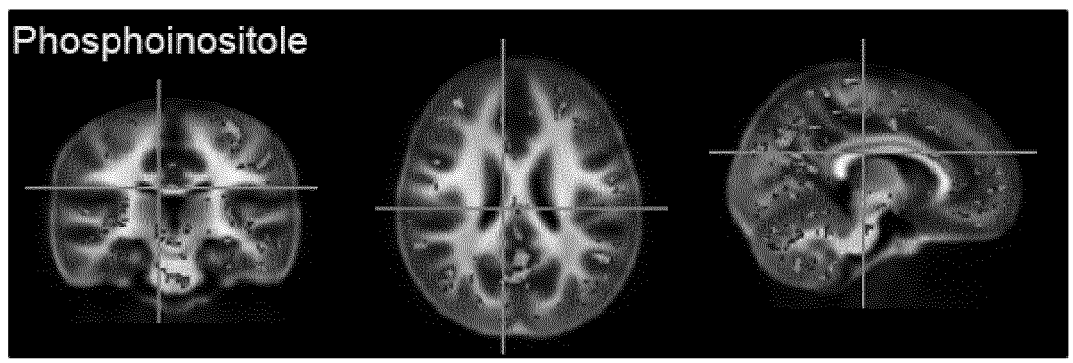
FIG. 1d—Is a brain image showing the myelinated brain regions associated with phosphatidylinositol.
Figure 1E:
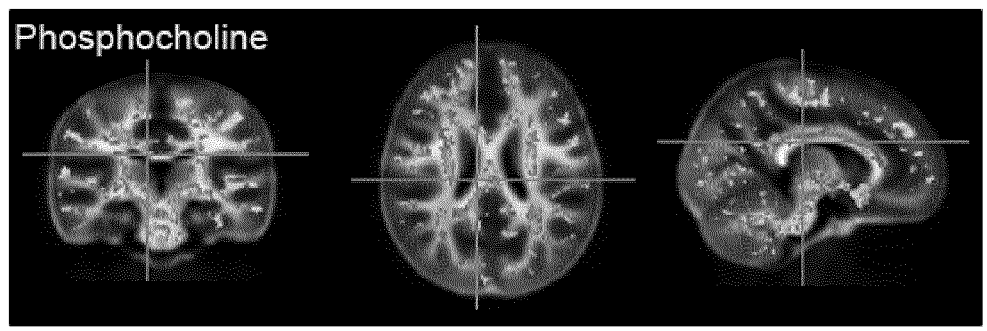
FIG. 1e—Is a brain image showing the myelinated brain regions associated with phosphatidylcholine.
Figure 1F:
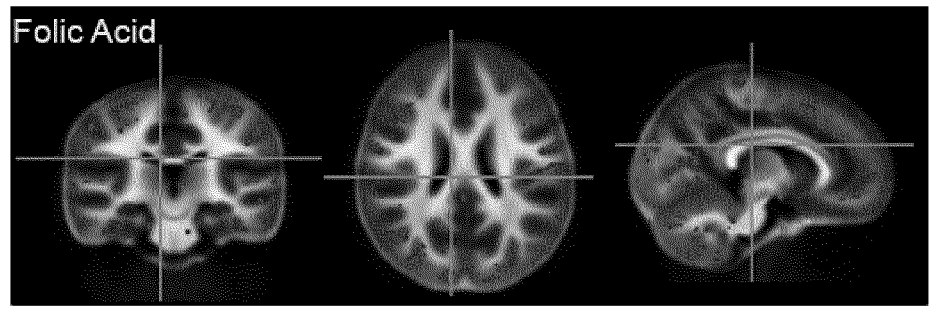
FIG. 1f—Is a brain image showing the myelinated brain regions associated with folic acid.
Figure 1G:
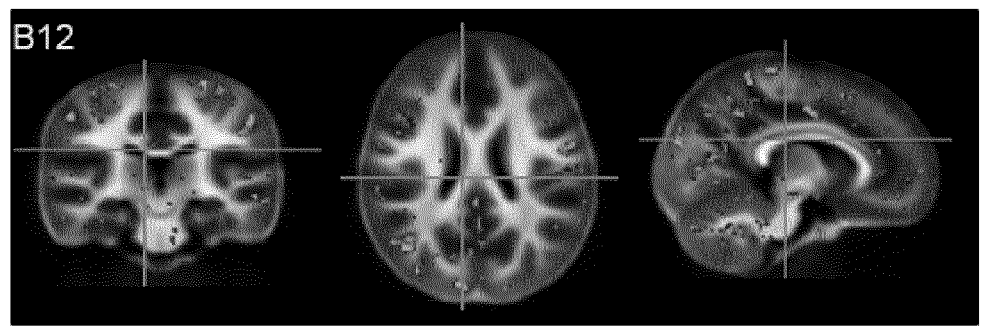
FIG. 1g—Is a brain image showing the myelinated brain regions associated with vitamin B12.
Figure 1H:
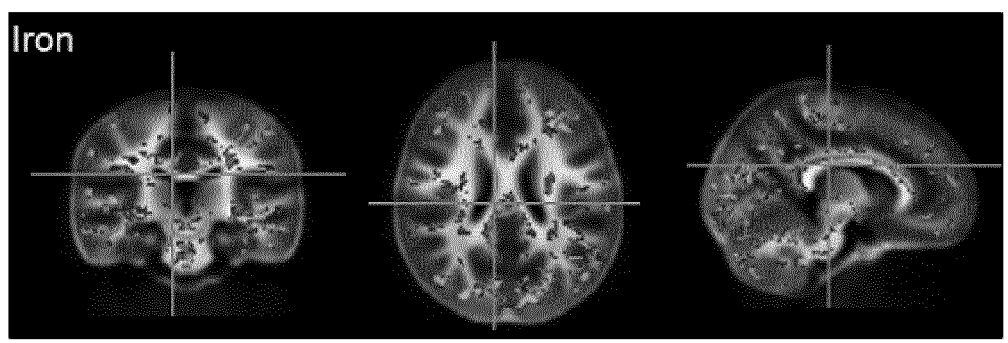
FIG. 1h—Is a brain image showing the myelinated brain regions associated with Iron.
Figure 1I:
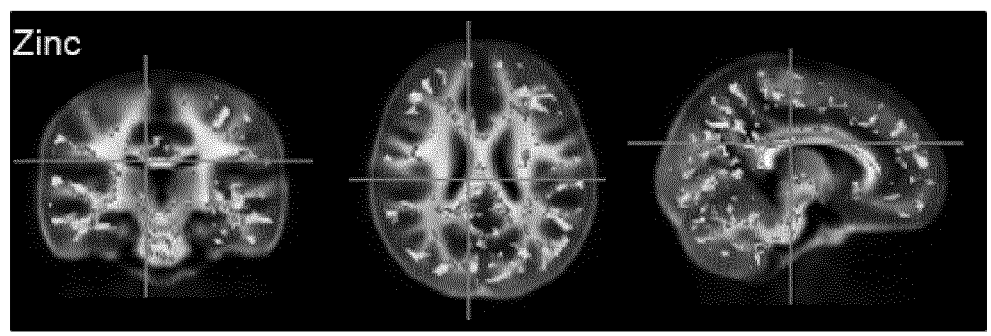
FIG. 1i—Is a brain image showing the myelinated brain regions associated with Zinc.
Figure 1J:
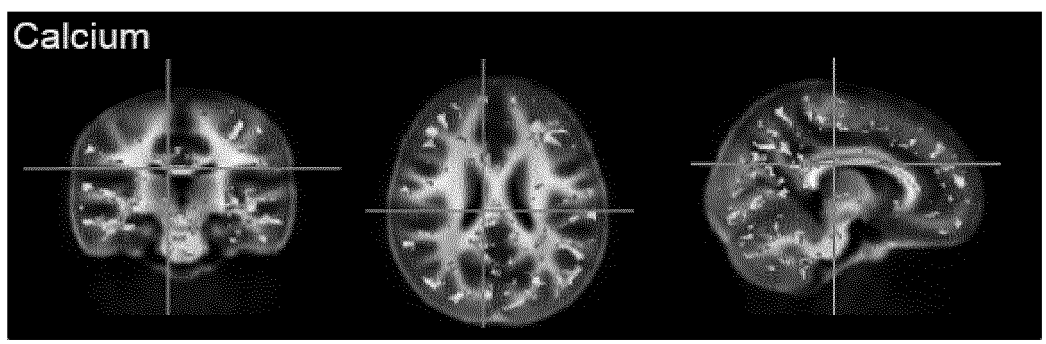
FIG. 1j—Is a brain image showing the myelinated brain regions associated with Calcium.
Figure 1K:
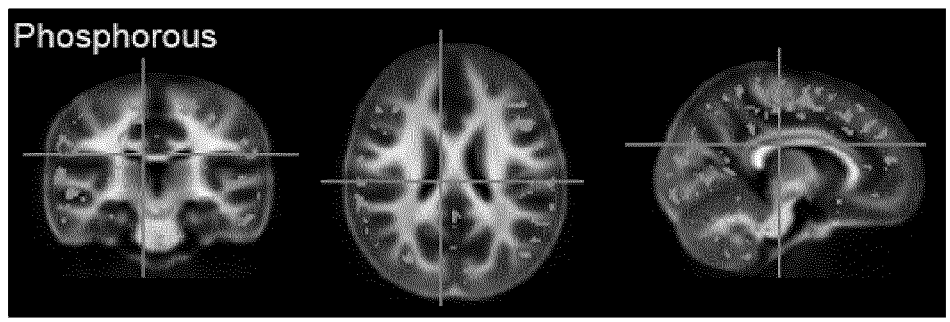
FIG. 1k—Is a brain image showing the myelinated brain regions associated with Phosphorus.
Figure 1L:
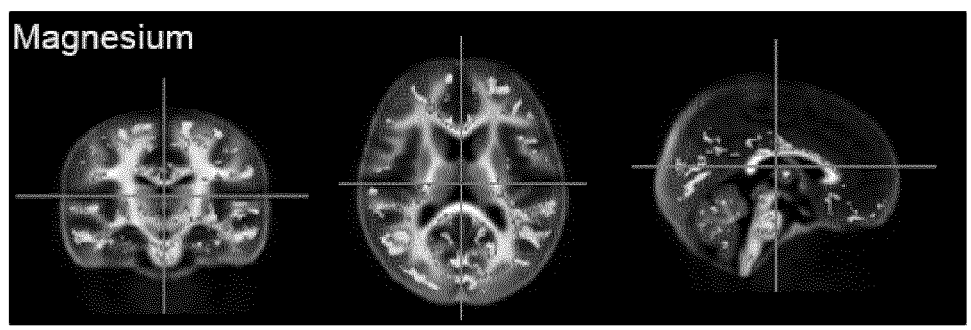
FIG. 1l—Is a brain image showing the myelinated brain regions associated with Magnesium.
Figure 1M:
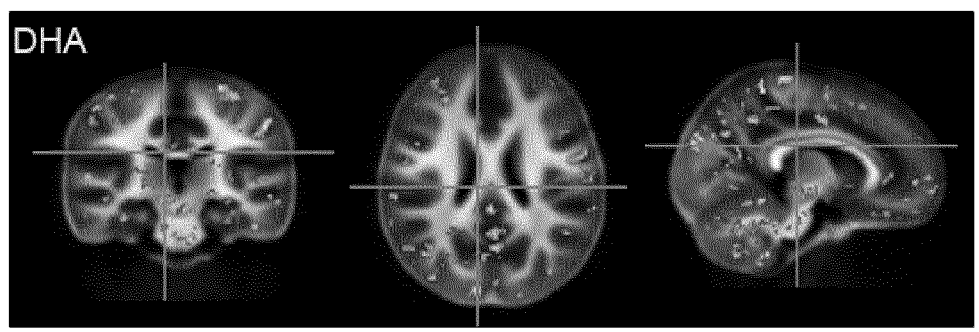
FIG. 1m—Is a brain image showing the myelinated brain regions associated with docosahexaenoic acid.
Figure 1N:
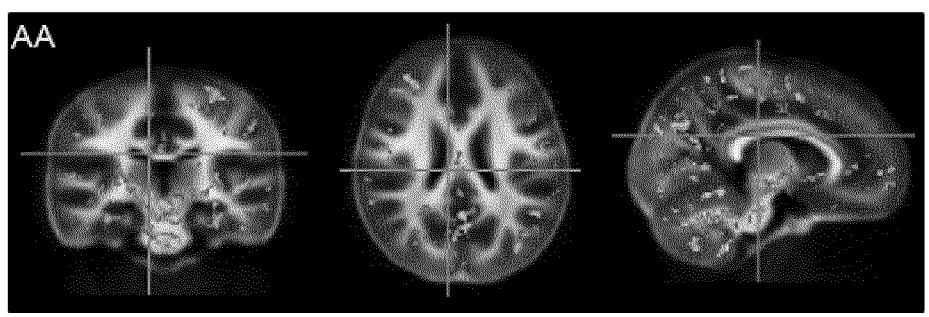
FIG. 1n—Is a brain image showing the myelinated brain regions associated with arachidonic acid.
Figure 2:
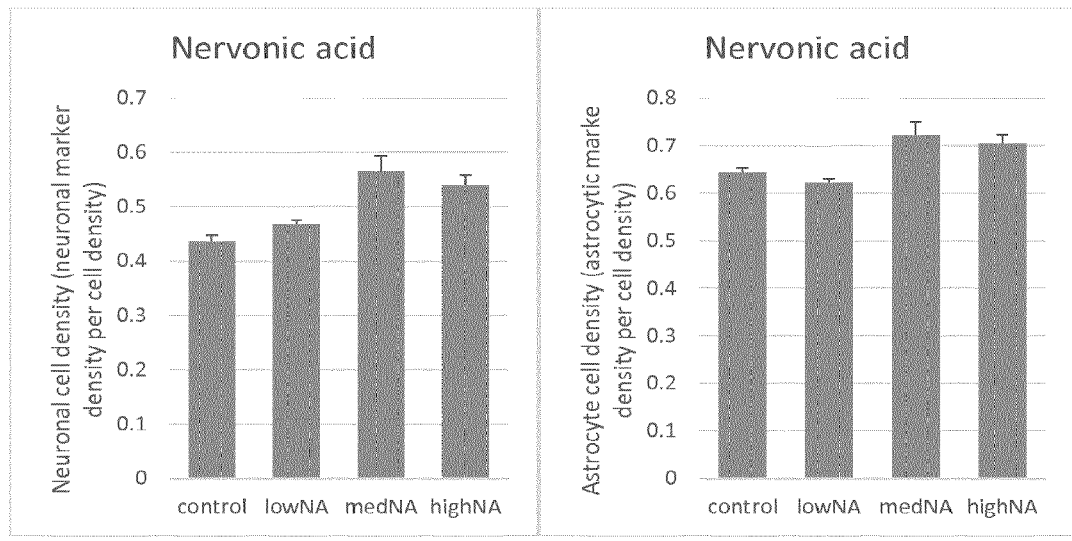
FIG. 2: Shows the effect of nervonic acid on neuronal cell density and astrocyte cell density.
Figure 3:
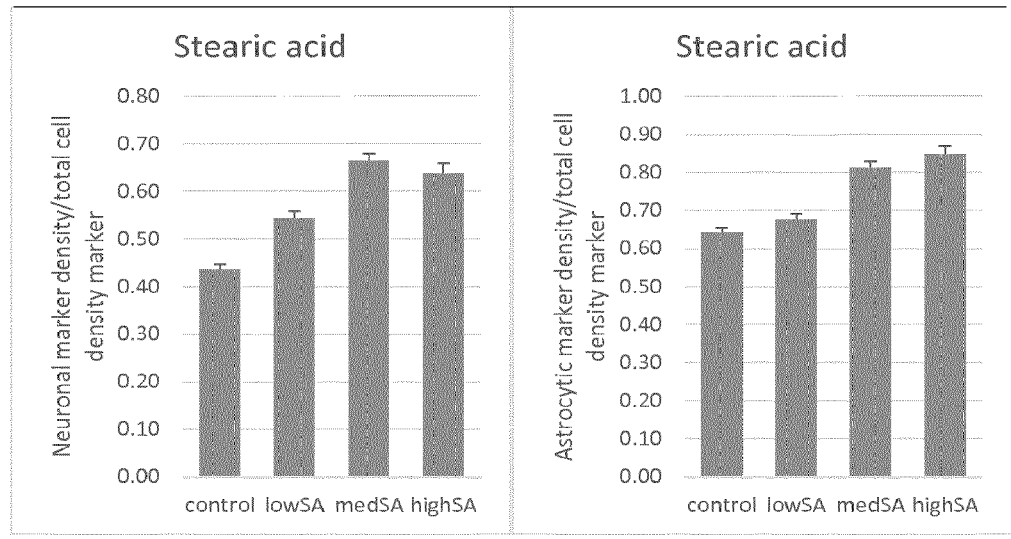
FIG. 3: Shows the effect of stearic acid on neuronal cell density and astrocyte cell density.
Figure 4:
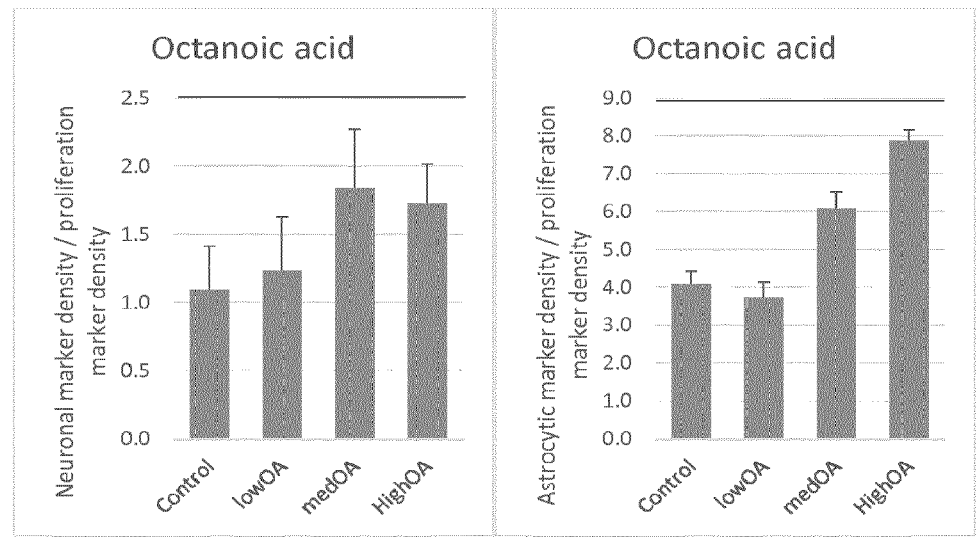
FIG. 4: Shows the effect of octanoic acid on neuronal cell density and astrocyte cell density.
Figure 5:
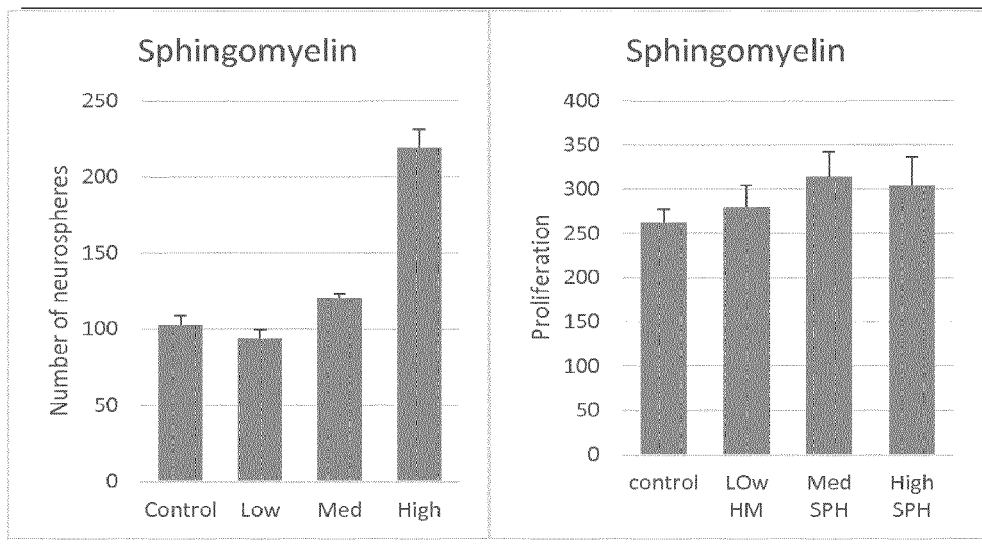
FIG. 5: Shows the effect of sphingomyelin on number of neurospheres and neuronal proliferation.

Results are reported in FIG. 1a.

Example 3

Vendors and Stock Solutions

| Compound | Company | Cat# | Cas# | Stock |
|---|---|---|---|---|
| Octanoic Acid | sigma | O3907 | 12407-2 | 50 mM |
| Nervonic Acid | Fluka | 87117 | 50637-6 | 10 mM |
| Stearic Acid | Fluka | 85679 | 57-114 | 10 mM |
| Sphingomyelin | sigma | S0756 | 8518710-6 | 10 mM |

Vehicles and Doses

| Compound | Vehicle/dissolved in | Dose 1 | Dose 2 | Dose 3 |
|---|---|---|---|---|
| Octanoic Acid | DMSO | 10 μM | 50 μM | 250 μM |
| Nervonic Acid | DMSO | 10 nM | 100 nM | 1 μm |
| Stearic Acid | DMSO | 100 nM | 1 μm | 10 μM |
| Sphingomyelin | Dissolved in ETOH/diluted in DMSO | 10 nM | 100 nM | 1 μm |

Media Compositions and Culture Methods
1) Neurobasal Complete Media
Neurobasal media (LIFE TECHNOLOGIES CORP, #21103-049)
50× B27 supplement (LIFE TECHNOLOGIES CORP, #12587-010)
2 mM L-Glutamine (LIFE TECHNOLOGIES CORP, #25030-149)

1x Pen-Strep (LIFE TECHNOLOGIES CORP, #15140-122)
2) Neurobasal Media Complete with Growth Factors (GF)
Above recipe with GF mix
1M Tris (MW 121.14, Fisher SCI BP152)
Heparin (sigma H3149)
BSA (Sigma A7030)
DNAse, RNase, Protease free water (Fisher SCI AC327390010)
EGF (GIBCO PHG0311)
bFGF vial (GIBCO PHG0021)
3) Neurobasal Media No Choline (Life Technologies, Formulated Custom, No L-Glutamine, No Phenol Red)
Note: complete and complete with GF made the same as above.
Generation of Neural Progenitor Cell (NPCs) Libraries: dissociation of E14 mouse neocortex
Reagents Needed:
DPBS (1x)+10% Pen/Strep
Neurobasal media/10% Pen/Strep/10x Hepes ul of GF for every 10 mL media). Cells were then grown overnight, and then use in the experiments.

Plating Cells in 96-Well Plates for Neurosphere Counts and Diameters Only

Corning Costar 3474, 96 well plate, Ultra low attachment

Dissociation and Plating of cells 3-4 mLs of cells were taken out of the tilted plate and add to a 15 ml conical. Some of the remaining media was used to rinse down the plate. All remaining media was drawn up and put into a 15 ml conical tube, and Spun at 130 G for 5 min. All media was removed. The cells were gently resuspended in 5 mls of warm PBS, spun again. PBS was then removed and the cells were then gently resuspended in 500 µl of Accutase (Corning™ Accutase™ Cell Detachment Solution, #25058Cl). The cells were then Pipetted gently with a 1000 µl tip to break up pellet, and then they were placed in a shaking water bath for 5-10 minutes, after which time they were swirled by hand frequently.

Media was prepared as indicated below, all media had GF:

| Compound | | | | | | |
|---|---|---|---|---|---|---|
| Octanoic Acid | Control/Vehicle | Low choline/Vehicle | 1% BSA | low | Med | 1:5 Oct:dec |
| Nervonic Acid | Control/Vehicle | Low choline/Vehicle | Med choline/Vehicle | low | Med | High |
| Stearic Acid | Control/Vehicle | Low choline/Vehicle | Med choline/Vehicle | low | Med | high |
| Sphingomyelin | Control/Vehicle | Low choline/Vehicle | Med choline/Vehicle | low | Med | high |

Procedure:
E14 pup brains were harvested and placed in ice cold DPBS (1x)+10% Pen/Strep, then they were dissected using a dissecting microscope. From each pup, one brain hemisphere was placed in 2 ml of Neurobasal media/10% P/S/10x Hepes and another brain hemisphere was placed in another tube.

The tissue from each tube was aseptically and manually dissociate into single cells, neurobasal complete medium was added and centrifuged at 130 G for 5 min. The tissue was then re-suspended in neurobasal complete media with GF and placed in a corning suspension culture dish 100 mm×20 mm (#430591). Cells were passage twice using a 1:3 ratio, after what they were centrifuged (130 g 5 min), resuspended in freezing media (10% DMSO and neurobasal complete media, no GF) and frozen in liquid nitrogen (LN2).

Thawing Cells for Compound Screen

Vials were remove from LN2, quickly defrosted, and cells were transferred, dropwise, to a 15 mL conical flask. 10 mls of complete neurobasal media was added. Cells were transferred to a suspension culture dish, and placed in an incubator for 2 hours. At 1.5 hours, cells were examined. Based on the health and number, the number of plates needed was estimated and the appropriate amount of complete neurobasal media was warmed. After 2 hours, cells were put in a 15 mL conical tube and spun at 130 G, 5 min. Cells were then resuspended in Neurobasal media complete with GF (3

Control and compound media was made with #2 media and contain 29 uM Choline,
Low (5 uM) and medium (70 uM) choline media was made with #3 media.

| Compound | Company | Cat | cas # | Stock | Vehicle/dissolved | Dose 1 | Dose 2 |
|---|---|---|---|---|---|---|---|
| Choline chloride | Sigma | 26978 | 67-48-L | 7 mM | PBS | 5 µm | 70 µm |

The media was Pipetted GENTLY using a 1000 µl tip and a then a 200 ul tip to further disperse cells.

Clumps were no bigger than ~3-5 cells. 5-10 mls of warm media (GF) was added to dilute enzyme. 2 mls of media was added. This was pipetted with a 1000 ul pipette, then 3 mls with added with a serological pipette. Cells were strained through a cell culture approved 40 uM strainer before they were plated.

1 ml was taken off to count cells. The cells were spun again. Media was removed from the cell pellet. 1 mls of prepared media (no GF) was added. The cells were pipetted with a 1000 ul pipette. Cell dilutions (24,000 cells/well) in 250 uL of appropriate media were made. Cells were swirled daily and grown for 2 days.

Fixation and Staining

1. The cells were fixed in the hood. For fixation and subsequent immunohistochemical analysis 100 ul of medium was removed and 100 ul 4% PFA in 1xPBS was added to fix the cells whilst counting the neurospheres by hand, then the cells were washed twice with 1xPBS for 5 min, and left in 1xPBS, wrapped in foil and left overnight at 4° C., or Dapi staining was carried out. 100 uL of PBS was removed and 100 uL of antibody (AB) staining solution (1% Goat serum, 1×PBS, and 0.1% triton X) block was added at room temp for 1 hour. AB staining solution was removed. The cells were then Stained with Dapi 1:5000 in AB staining solution, 100 ul per well, the cells were then incubated at room temp for 15 min in the dark. The cells were then washed 2 times in AB staining solution for five min. Imaging was carried out using a GE Cytell imager or LSM 710, Zeiss confocal microscope and the diameters of neurospheres with ImageJ software (National Institutes of Health) was analysed.

Plating Cells in 24 Well Plate for Monolayer Differentiation or EdU Incorporation Assays

| Compound | | | | | | |
|---|---|---|---|---|---|---|
| Octanoic Acid | Control/Vehicle | Low choline/Vehicle | Med choline/Vehicle | low | Med | High |
| Nervonic Acid | Control/Vehicle | Low choline/Vehicle | Med choline/Vehicle | low | Med | High |
| Stearic Acid | Control/Vehicle | Low choline/Vehicle | Med choline/Vehicle | low | Med | high |
| Sphingomyelin | Control/Vehicle | Low choline/Vehicle | Med choline/Vehicle | low | Med | high |

24 well glass bottom plates (Mat Tek P24G-1.0-13-F Case, glass bottom 24 well plates) were coated with poly-L-ornithin (Sigma P4957) and Fibronection (Sigma F1141) before use in the assay below.

See Dissociation and Plating of cells above.

Cells were plated (10,000 cells per well) in Complete media with GF for 24 hours (500 ul per well). Once cells had been attached they were switched to choline deficient media, other compound media, or appropriate media.

Differentiation Assay: Quantification of Neuronal, Glial and NPC Marker Expression After 24 hours, it was ensured that cells were attached to the plate, then the medium was carefully removed.

500 µL of compound media containing 2% Nu Serum (serum substitute) (Corning™ Nu-Serum Growth Medium Supplement, #CB55004), control, low choline, or medium choline media, was added. Note: medium contains no GF.

Control and compound media were made with #2 media and contain 29 uM Choline, low (5 uM) and medium (70 uM) choline media was made with #3 media.

The cells were culture for 9 d in media plus 2% Nu Serum, the medium was changed every 2nd day. For fixation and subsequent immunohistochemical analysis the medium was removed, the cells were rinsed once with 1×PBS for 5 min, and fixed with 4% PFA in 1×PBS for 15 min at 4° C. The cells were then washed twice with 1×PBS for 5 min, left in 1×PBS, wrapped in foil and left overnight at 4 C, or they were immediately primary antibody staining was carried out.

Staining for Differentiation

PBS was removed and enough AB staining solution (1% Goat serum, 1×PBS, and 0.1% triton X) was added to cover the bottom, the block was kept at room temp for 1 hour.

Primary antibody dilutions were made in appropriate amount of AB staining solution, 250 ul per well (the antibodies were only kept out on ice for a short time, mouse anti-MAP2 or TUJ1 1:500 (neuron marker), rabbit anti-GFAP (glial marker) 1:1000, chicken anti-Nestin CFP (EGFP antibody (progenitor cell marker)) 1:1000. AB staining solution was removed and a solution of primary antibodies was added to each chamber. The cells were wrapped in foil and kept overnight 4° C. The cells were then washed with 400 ul of AB staining solution for 5 min once to remove primary antibodies. Secondary antibody solutions were made (enough for 250 ul of each chamber) (Goat anti-mouse alexa 488 1:2000, anti-rabbit Cy3 (1:500), anti-chicken alexa 647 1:500, and 1:5000 Dapi).

The cells were incubated at room temp for 1 hour in the dark and washed 2 time in AB staining solution for five mins. They were then kept at 4° C. or Imaged using a GE Cytell imager or LSM 710, Zeiss confocal microscope and analyze with ImageJ software (National Institutes of Health).

Microtubule-Associated Protein 2 (MAP2), Neuronal Beta-Tubulin III (TuJ1), Glial Fibrillary Acidic Protein (GFAP), and Nestin CFP (EGFP Antibody).

Each marker expression was measured on collected images (integrated density measure in ImageJ) and normalized to DAPI fluorescence, marking all nuclei (integrated density measure).

Octanoic Acid were labeled with neuronal beta-tubulin III (TuJ1), subsequent compounds were labeled with Microtubule-associated protein 2 (MAP2).

Monolayer Culture NPC Proliferation Assay (Incorporation of EdU—S Phase Marker)

After 24 h, it was ensured that cells had attached to the plate then the medium was carefully removed. 500 µL of compound media plus GF. was added. The cells were cultured for 3 days in appropriate media.

Control and compound media was made with #2 media and contains 29 uM Choline, Low (5 uM) and medium (70 uM) choline media was made with #3 media.

EDU incorporation was measured using Click-iT® EdU Alexa Fluor® 555 Imaging Kit (Life technologies, #c10338).

At the end of day 3 EdU was added to each well at 10 µM for 30 minutes prior to fixation. For fixation and subsequent immunohistochemical analysis, the medium was removed, the cells were rinsed once with 1×PBS for 5 min, and fixed with 4% PFA in 1×PBS for 15 min at 4° C., then the cells were washed twice with 1×PBS for 5 min, left in 1×PBS, wrapped in foil and leave overnight at 4° C., or staining was proceeded with.

PBS was removed and enough AB staining solution (1% Goat serum, 1×PBS, and 0.1% triton X) added to cover the bottom, the block was kept at room temp for 1 hour. The cells were stained for EDU. The cells were Incubated for 30 min at room temp, in the dark. The cells were washed with 1×PBS and stained with Dapi 1:5000 ul for 15 min. The cells were washed once with 1×PBS, then left in PBS at 4° C., or Imaged immediately using a GE Cytell imager (cell viability application), or LSM 710, Zeiss confocal microscope (with ImageJ software (National Institutes of Health) analysis).

Results are shown in Tables 3-7 and FIGS. 2 to 5.

TABLE 3

Effect of Nervonic acid on Neuronal Cell density and astrocyte cell density

|         | neuronal | astrocytic |
|---------|----------|------------|
| control | 0.436189 | 0.642448   |
| lowNA   | 0.467588 | 0.621784   |
| medNA   | 0.56563  | 0.721512   |
| highNA  | 0.539448 | 0.70279    |

TABLE 4

Effect of Stearic acid on Neuronal Cell density and astrocyte cell density

|         | Neuronal | astrocytic |
|---------|----------|------------|
| control | 0.44     | 0.64       |
| lowSA   | 0.54     | 0.68       |
| medSA   | 0.66     | 0.81       |
| highSA  | 0.64     | 0.85       |

TABLE 5

Effect of Octanoic acid on Neuronal Cell density and astrocyte cell density

|         | Neuronal | Astrocytic |
|---------|----------|------------|
| Control | 1.1      | 4.1        |
| lowOA   | 1.2      | 3.7        |
| medOA   | 1.8      | 6.1        |
| HighOA  | 1.7      | 7.9        |

TABLE 6

Effect of Sphingomyelin on number of neurospheres

| Sphingomyelin  | Control | Low | Med | High |
|----------------|---------|-----|-----|------|
| Average (Mean) | 103     | 94  | 121 | 219  |

TABLE 7

Effect of Sphingomyelin on neuronal proliferation

|         | DAPI |
|---------|------|
| control | 262  |
| lowSM   | 280  |
| medSM   | 314  |
| highSM  | 305  |

Example 4

Experimental Part

Samples

Ingredient C2 a whey protein concentrate enriched in alpha lactalbumin (Sample Manager ID: K2Q-00030); first infant milk containing whey protein concentrate enriched in alpha Lactalbumin (Sample Manager ID: K2Q-00032); cow's milk (whole milk); human breast milk (quality control pool of 6 individual samples, collected after week 4 following child birth; Lee Biosolutions, St Louis, MI, USA).

Extraction of Phospholipids from Milk Products

Milk powder: A quantity of 1 g of homogenized powder was weighed into a 50-mL glass flask and diluted into 20 mL of pure distilled water. The solution was heated at 40° C. for 30 min in a water bath. A volume of 500 µL of this solution was put in a 10-mL glass tube.

Cow milk and Human milk: A quantity of 500 µL of homogenized liquid was aliquoted to a 10-mL glass tube.

Analytes were extracted following the MP on quantification of human breast milk by UPLC-MS/MS (RDLS-MP-80138-Rev01) in triplicate using 9.5 mL of a mixture of chloroform/methanol (2+1). Briefly, the tubes were shaken and placed in an ultrasonic bath at 40° C. for 15 min, followed by centrifugation for 10 min at 2500 rpm. A volume of 2 mL of potassium chloride solution (0.88%, m/m) was added to the liquid phase then shaken and centrifuged for 10 min at 2500 rpm. The lower organic phase was transferred into a glass vial, evaporated to dryness under gentle $N_2$ stream and reconstituted in 500 µL of chloroform/methanol (9+1) before injection into the LC-MS.

Analysis of Phospholipids by Liquid Chromatography Coupled to Mass Spectrometry (LC-MS)

Analyses were performed on a Q Exactive Plus Orbitrap (Thermo Fisher Scientific, Bremen, Germany) equipped with a Thermo Scientific Dionex UltiMate 3000 Rapid Separation LC system. Separation was performed on an HILIC column (100×2.1 (i.d.) mm; 1.7 µm) with a mobile phase composition of (A) ammonium acetate 10 mM and (B) acetonitrile. The injection volume was set to 10 µL and the gradient started from 95% B to 70% B over 15 min, maintained 1 min at 70% B, returned to initial conditions in 3 min and equilibrated for 6 min.

Q Exactive Plus Orbitrap was equipped with an atmospheric pressure chemical ionization (APCI) probe operated in the positive ion mode. APCI and MS parameters were as follows: corona discharge current 4.0 µA, sheath gas and auxiliary gas 24 and 5 arbitrary units, respectively; capillary and vaporizer temperatures 320 and 390° C., respectively, sweep gas flow rate was 0 arbitrary unit and s-lens RF level was 80. Automatic gain control (AGC) target value was set at $1\times10^6$ charges and maximum injection time at 100 ms with resolution of 35,000 and 1 microscan per full MS. AGC was set to $1\times10^6$ charges and maximum injection time of 250 ms with resolution of 17,500 with 1 microscan in the data independent fragmentation mode. An inclusion list of selected parent ions was used with normalized collision energy of 30%. Data were acquired over the mass range 133-2000 Da in profile mode. External mass calibration was applied. The system was controlled by Xcalibur 3.0 (Thermo Fisher Scientific).

SM species were extracted from total ion chromatogram using accurate mass. Parent ions corresponded to in-source loss of phosphatidylcholine into ceramide. An inclusion list was used for specific fragmentation of 57 SM regioisomers built on parent ions corresponding to m/z of ceramide with loss of water [Cer-$H_2O+H^+$], based on LipidView database and literature (Trenerry V. C., Akbaridoust G., Plozza T., Rochfort S., Wales W. J., Auldist M., Ajilouni S. Ultra-high-performance liquid chromatography-ion trap mass spectrometry characterisation of milk polar lipids from dairy cows fed different diets. Food Chemistry 2013, 141, 1451-1460; Godzien J., Ciborowski M., Martinez-Alcazar M. P., Samczuk P., Kretowski A., Barbas C. Rapid and reliable identification of phospholipids for untargeted metabolomics with LC-ESI-QTOF-MS/MS. Journal of Proteome Research 2015, 14, 3204-3216).

Analysis of Fatty Acid Methyl Ester (FAME) by Gas Chromatography with Flame Ionization Detector (GC-FID)

SM fractions were collected between 8.5 and 10 min into glass tubes 5 times for each sample. After solvent evaporation under $N_2$ stream, FAME analyses were conducted in triplicate following the MP for quantification of fatty acid in human milk by gas chromatography (RDLS-MP-8980-00030-Rev01-FAME_Human milk fat 2012, Vers. 1.0).

Result and Discussion

Hydrophilic interaction liquid chromatography (HILIC) was used to separate PL classes (i.e. phosphatidylinositol (PI), phosphatidylserine (PS), phosphatidylethanolamine (PE), phosphatidylcholine (PC) and SM). The number of carbons and unsaturation within the individual SM species was assigned based on the accurate mass of the pseudo-molecular ion detected in the Orbitrap mass spectrometer. Relative abundance of SM species was determined for comparison between ingredient, infant formula, cow's milk and human milk.

SM Species in Different Milk Products

45 SM species were detected in the analysed samples (Table 8).

TABLE 8

SM species detected (indicated by x) in ingredient, infant formula, cow's milk and human milk samples. SM species that were only detected in human milk are indicated in bold.

| SM | Ingredient | Infant Formula | Cow's Milk | Human Milk |
|---|---|---|---|---|
| SM 24:1 | | | | X |
| SM 25:0 | X | X | X | X |
| SM 28:1 | X | X | X | X |
| SM 28:0 | X | X | X | X |
| SM 30:2 | X | X | X | X |
| SM 30:1 | X | X | X | X |
| SM 30:0 | X | X | X | X |
| SM 32:3 | X | X | X | X |
| SM 32:2 | X | X | X | X |
| SM 32:1 | X | X | X | X |
| SM 32:0 | X | X | X | X |
| SM 33:1 | X | X | X | X |
| SM 34:3 | X | X | X | X |
| SM 34:2 | X | X | X | X |
| SM 34:1 | X | X | X | X |
| SM 34:0 | X | X | X | X |
| SM 35:2 | X | X | X | X |
| SM 35:0 | X | X | X | X |
| SM 36:4 | X | X | X | X |
| SM 36:3 | X | X | X | X |
| SM 36:2 | X | X | X | X |
| SM 36:1 | X | X | X | X |
| SM 36:0 | X | X | X | X |
| SM 37:1 | X | X | X | X |
| SM 37:0 | X | X | X | X |
| SM 38:4 | | | | X |
| SM 38:3 | | | | X |
| SM 38:2 | X | X | X | X |
| SM 38:1 | X | X | X | X |
| SM 38:0 | X | X | X | X |
| SM 39:1 | X | X | X | X |
| SM 39:0 | X | X | X | X |
| SM 40:2 | X | X | X | X |
| SM 40:1 | X | X | X | X |
| SM 40:0 | X | X | X | X |
| SM 41:2 | X | X | | |
| SM 41:1 | X | X | X | X |
| SM 41:0 | X | X | X | X |
| SM 42:4 | | | | X |
| SM 42:3 | X | | X | |
| SM 42:2 | X | X | X | X |
| SM 42:1 | X | X | X | X |
| SM 42:0 | X | X | X | X |
| SM 44:3 | X | | X | |
| SM 44:1 | X | X | X | X |

The species SM 24:1, SM 38:4, SM 38:3 and SM 42:4 were only found at trace levels in human milk.

Relative Abundance of SM Species

Figure 6:
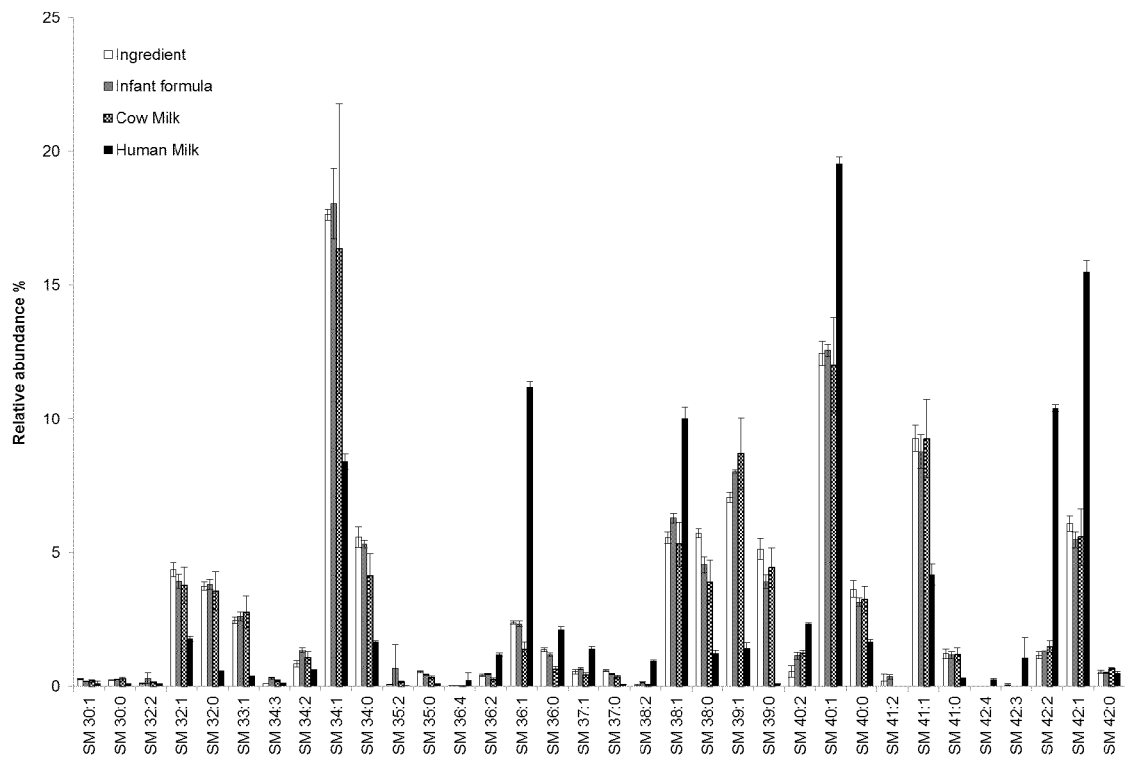
FIG. 6: Shows the relative abundance of main SM species in ingredient, infant formula, cow milk and human milk. (Error bars represented the standard deviation with n=3).

The relative abundance (%) of SM within different milk products was estimated based on the peak area divided by the sum of all peak area corresponding to SM species in the chromatogram per each sample. FIG. 6 shows the relative abundance of the main SM species in ingredient, infant formula, cow's milk and human milk.

The relative abundance of SM species present in ingredient and infant formula was comparable to that of cow's milk, and slightly different from human milkortion of some species (e.g. SM 32:1, SM 32:0, SM 33:1; SM 34:1, SM 38:0, SM 39:1, SM 39:0 and SM 41:1) were lower in human milk than in ingredient, infant formula and cow's milk. Whereas SM 36:2, SM 36:1, SM 36:0, SM 37:1, SM 38:2, SM 38:1, SM 40:1, SM 42:2 and SM 42:1 had higher relative abundance in human milk compared to the other milk products.

Human milk sample consisted of a quality control pool of 6 individual samples collected at or later than 4 weeks after child birth. Knowing that SM abundance in human milk varies in function of the diet and lactation time, this can partly explain the observed differences. Nevertheless, despite the variations in the relative abundance of some SM species, >85% of the SM species that were detected in human milk were also identified in infant formula and in cow's milk.

It is noteworthy that for a given m/z extracted from the MS trace, different LCB-FA combinations could be suggested (e.g. SM 34:1 could correspond to SM d18:1/16:0, d18:0/16:1, d16:1/18:0 etc.). Therefore, we evaluated GC FA profile to gather more information on the SM molecular structures between the different milk products.

Fatty Acid Profile in SM Fraction from Different Milk Products

Regioisomeric structure of SM was investigated by first fractionating the SM and then analysing the FA present in the fractions by GC-FID. Fractionation of SM was performed as described above for LC-MS analysis, but in this case the effluent was directed into a 5-mL glass tube instead of the MS. Each fraction was then subjected to methylation procedure before subsequent GC analysis. The relative abundance of FAs within the SM fraction is represented in FIG. 7.

Figure 7:
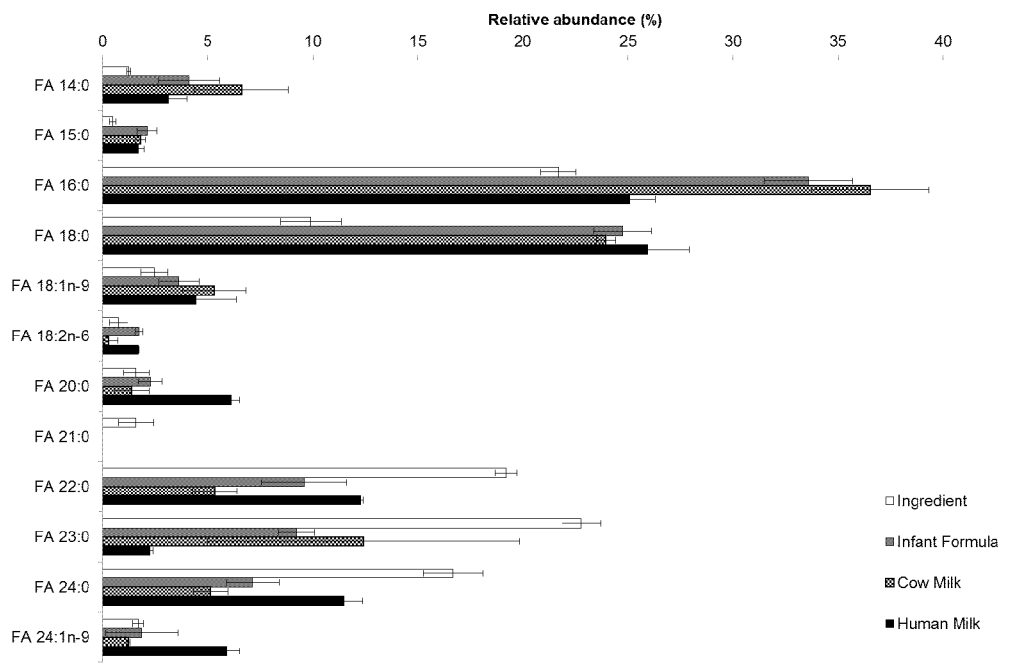
FIG. 7: Shows the relative FA abundance in SM fraction from ingredient, infant formula, cow's milk, and human milk. (Error bars represented the standard deviation with n=3).
Figure 8:
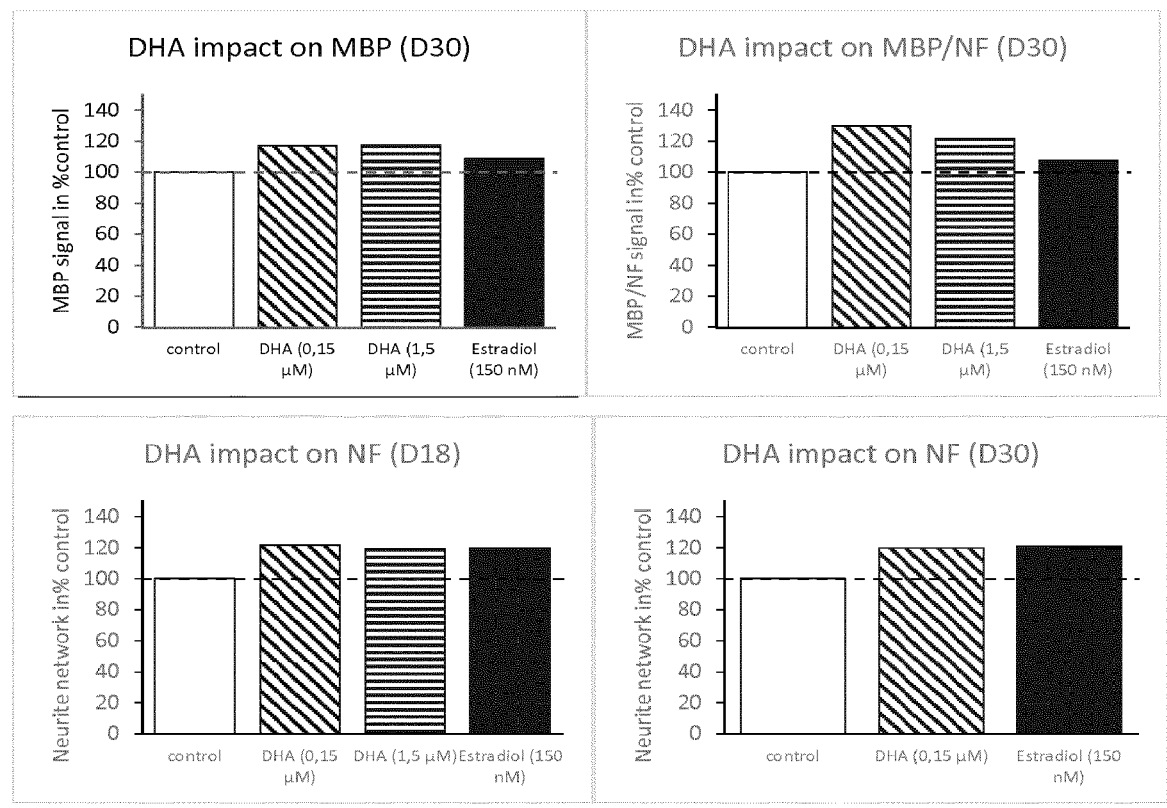
FIG. 8: Shows the impact of DHA on MBP, NF, and/or MBP/NF at day 18 and/or day 30.
Figure 9:
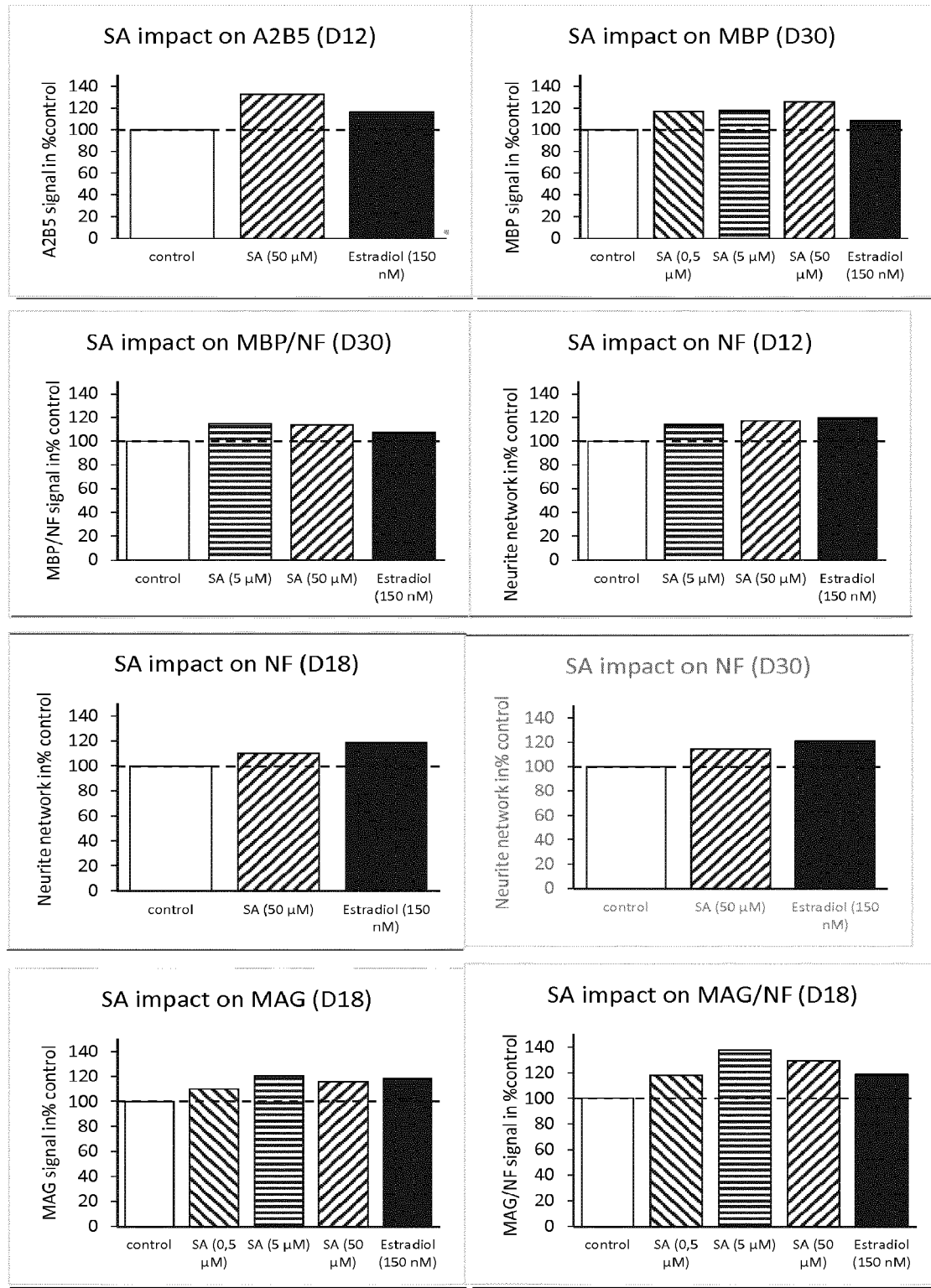
FIG. 9: Shows the impact of stearic acid on A2B5, MBP, MAG, NF, MBP/NF, and/or MAG/NF at day 12, day 18 and/or day 30.
Figure 10:
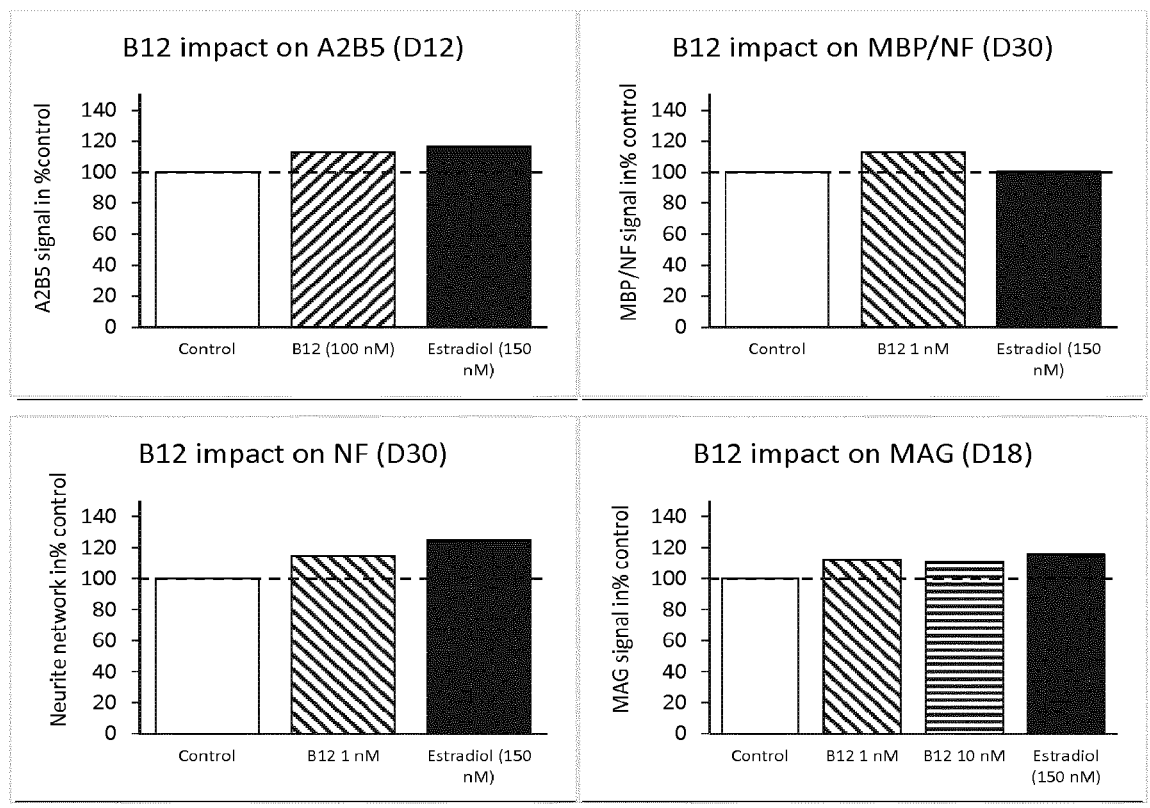
FIG. 10: Shows the impact of vitamin B12 on A2B5, NF, MBP/NF, and/or MAG at day 12, day 18 and/or day 30.
Figure 11:
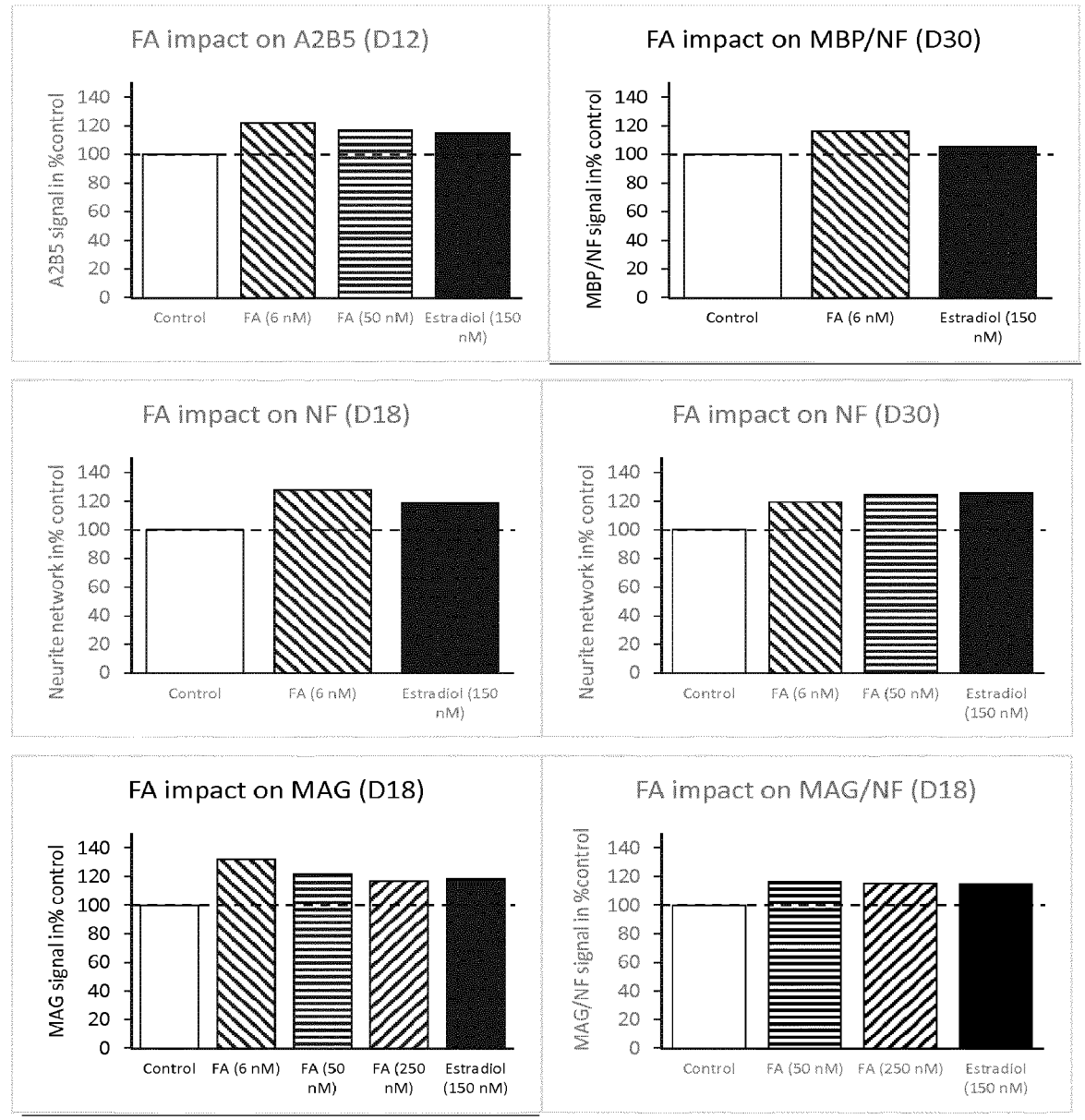
FIG. 11: Shows the impact of folic acid on A2B5, NF, MAG, MAG/NF, and/or MBP/NF at day 12, day 18 and/or day 30.
Figure 12:
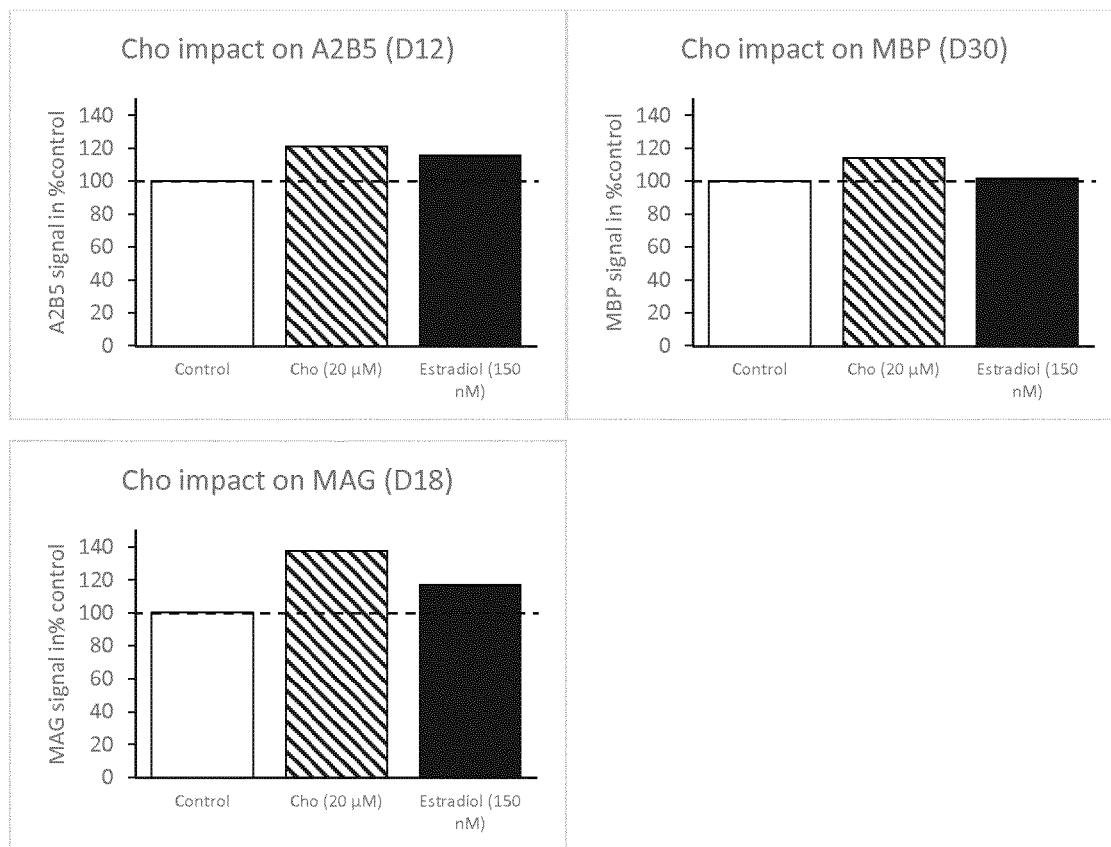
FIG. 12: Shows the impact of choline on A2B5, MAG and/or MBP at day 12, day 18 or day 30.
Figure 13:
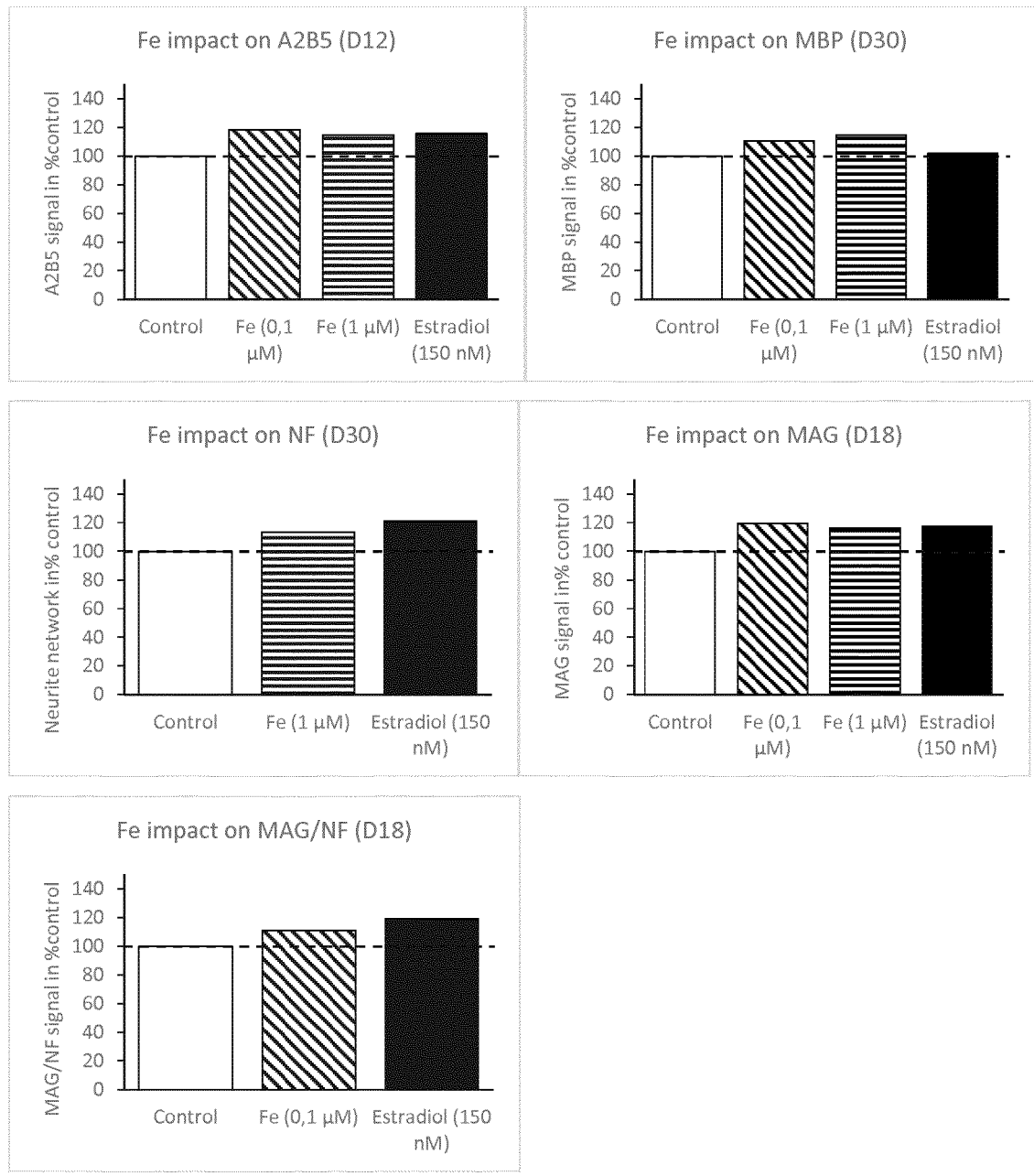
FIG. 13: Shows the impact of Iron on A2B5, MBP, MAG, NF, and/or MAG/NF at day 12, day 18 and/or day 30.
Figure 14:
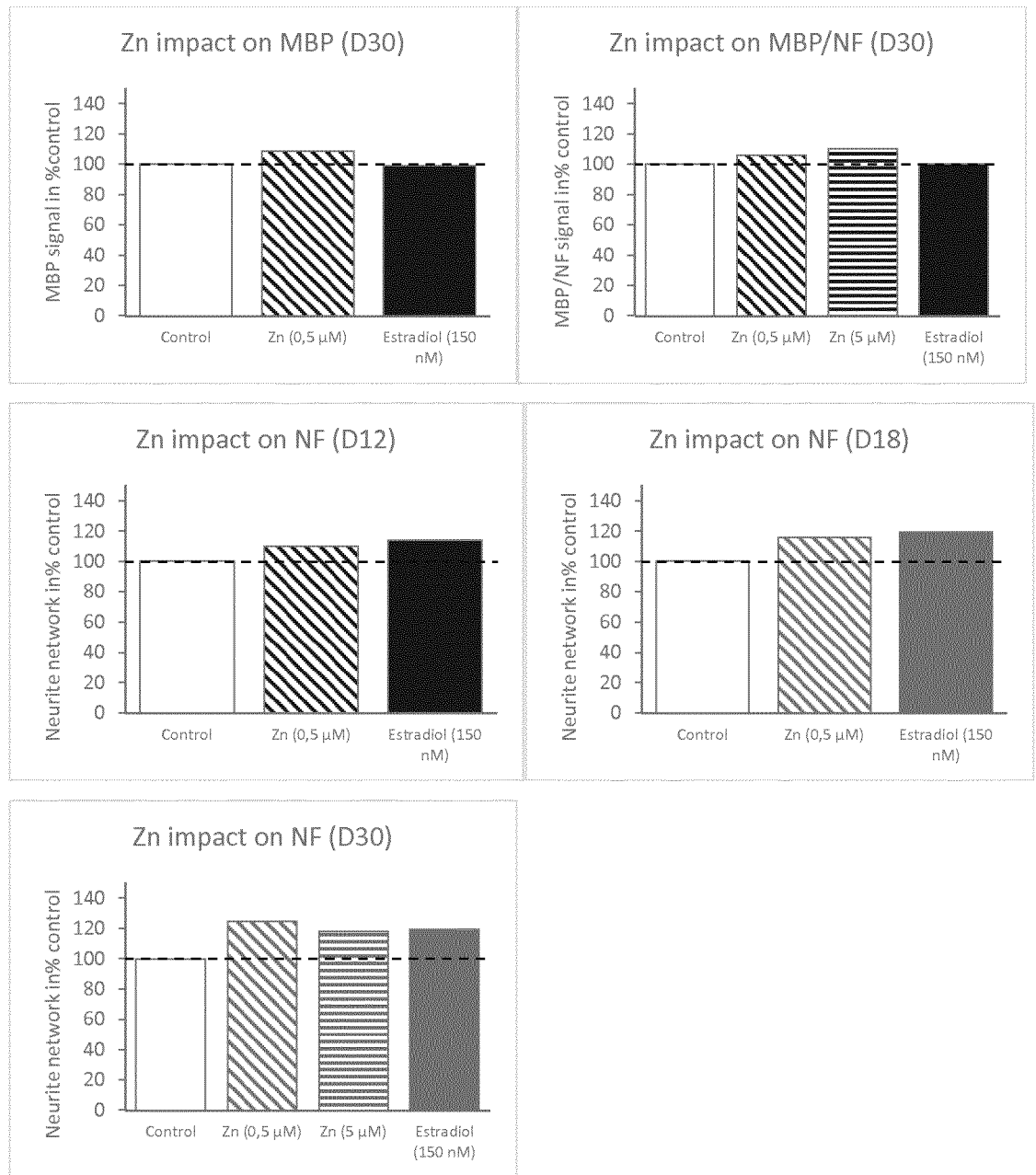
FIG. 14: Shows the impact of Zinc on MBP, NF and/or MBP/NF at day 12, day 18 and/or day 30.
Figure 15:
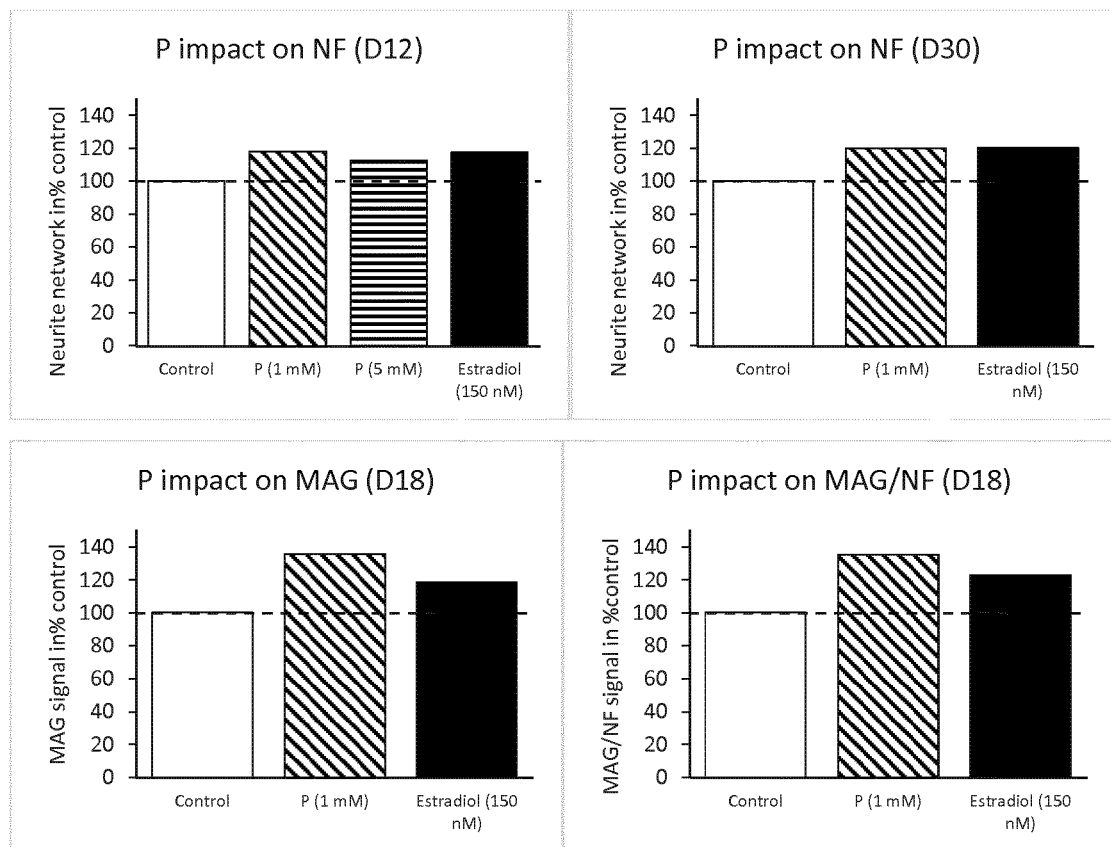
FIG. 15: Shows the impact of phosphorus on MAG, NF, and/or MAG/NF at day 12, day 18 and/or day 30.
Figure 16:
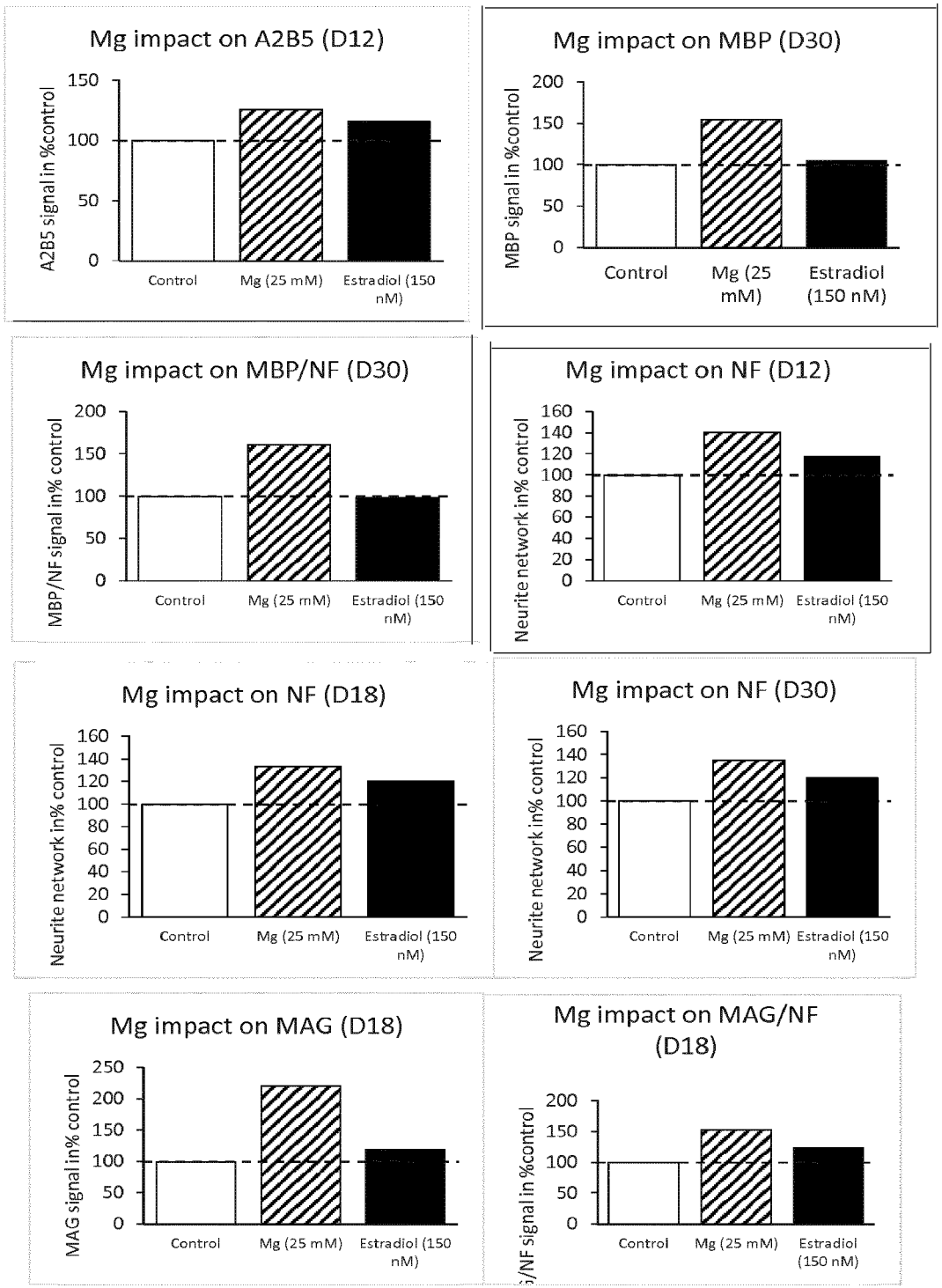
FIG. 16: Shows the impact of magnesium on A2B5, MBP, NF, MAG, MBP/NF and/or MAG/NF at day 12, day 18 and/or day 30.
Figure 17:
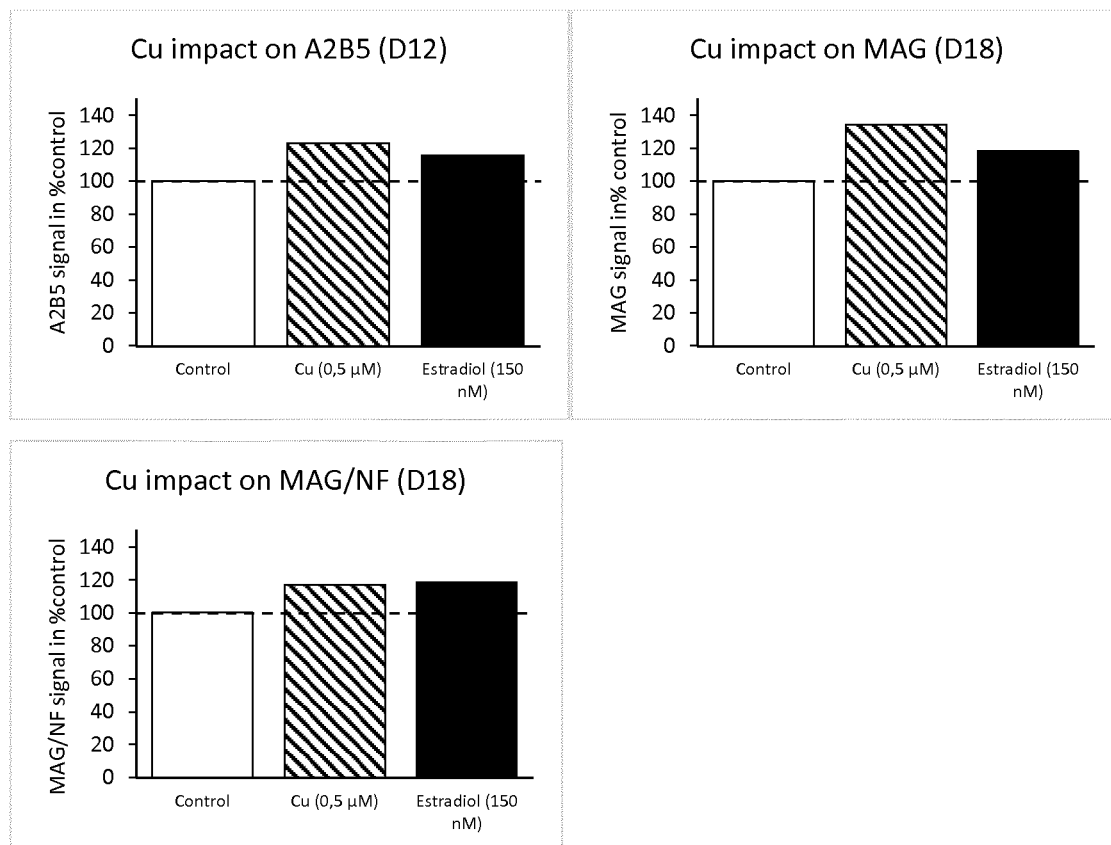
FIG. 17: Shows the impact of copper on A2BF, MAG, and/or MAG/NF at day 12 and/or day 18.
Figure 18:
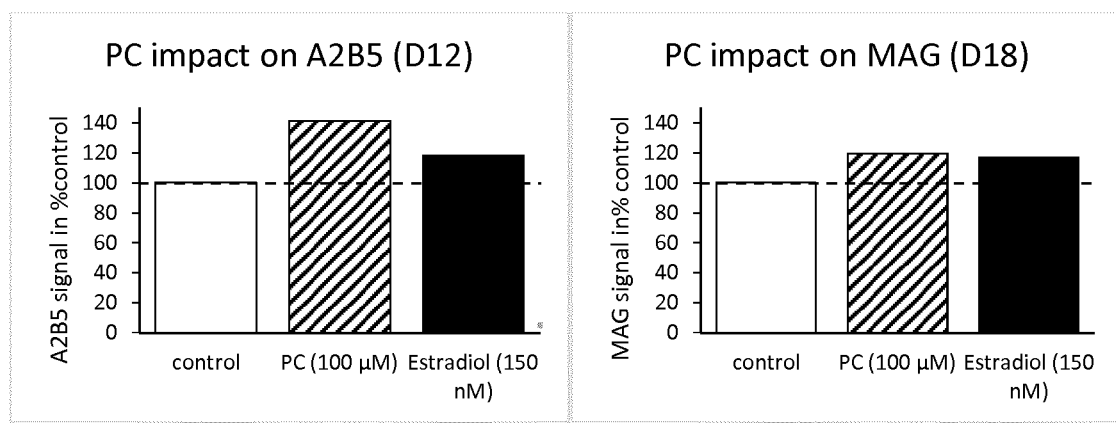
FIG. 18: shows the impact of phosphatidylcholine on A2B5 at day 12 and on MAG at day 18.
Figure 19:
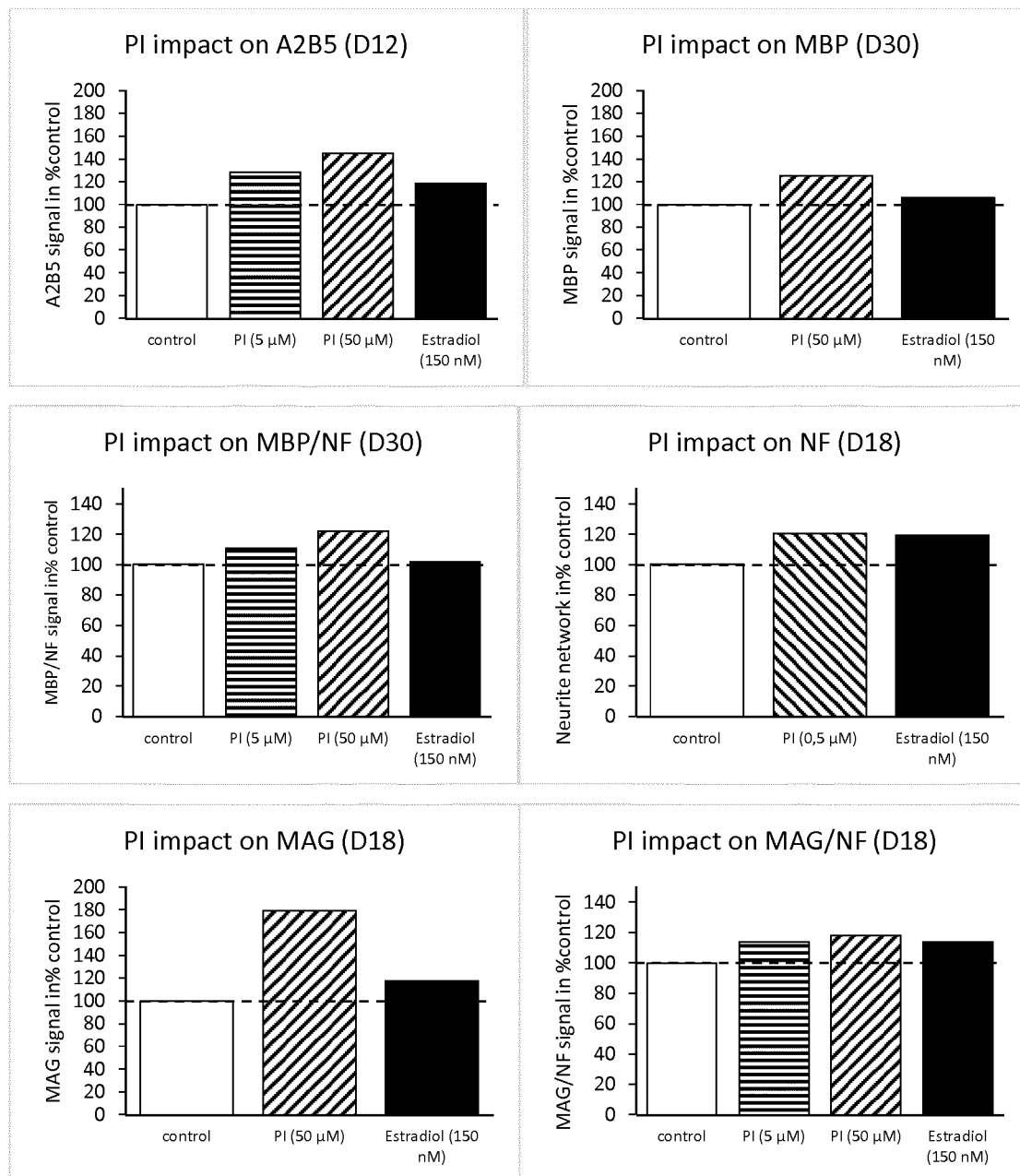
FIG. 19: Shows the impact of phosphatidylinositol on A2B5, MBP, MAG, NF, MAG/NF at day 12, day 18 and/or day 30.
Figure 20:
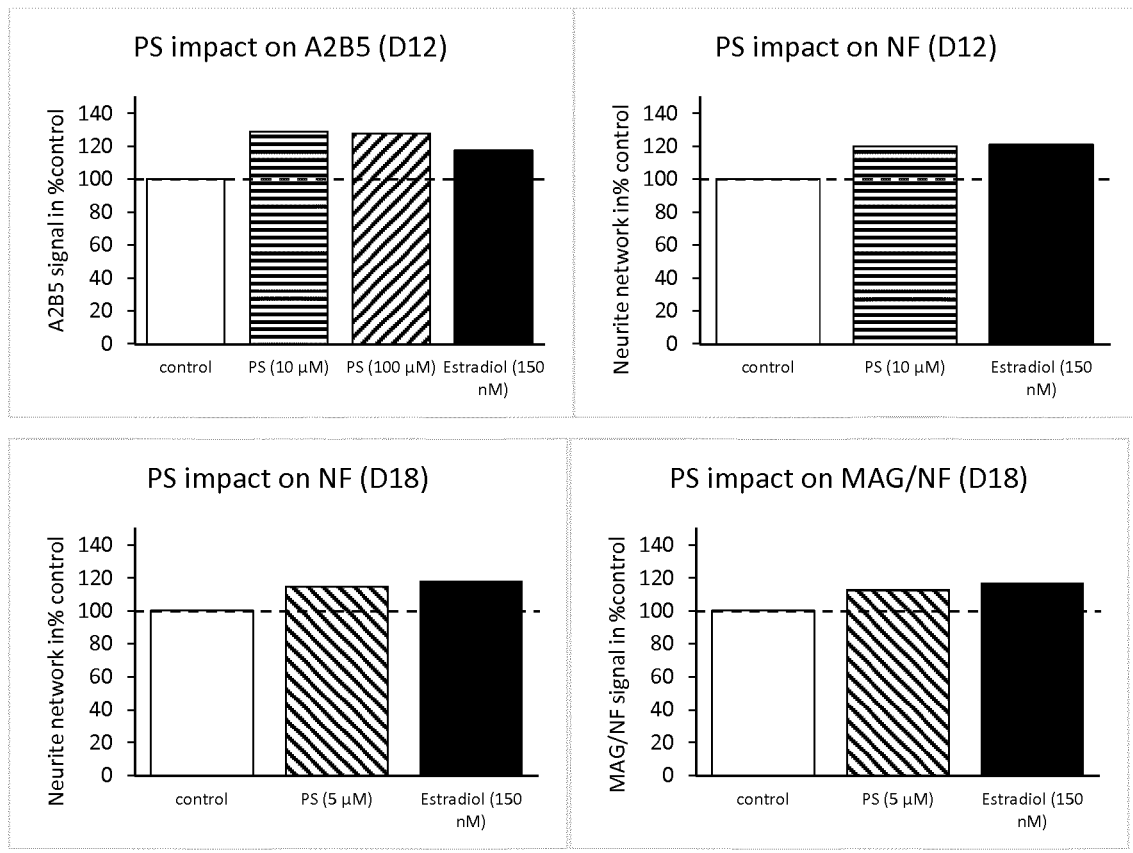
FIG. 20: Shows the impact of phosphatidylserine on A2B5, NF, and/or MAG/NF at day 12 and/or D18.
Figure 21:
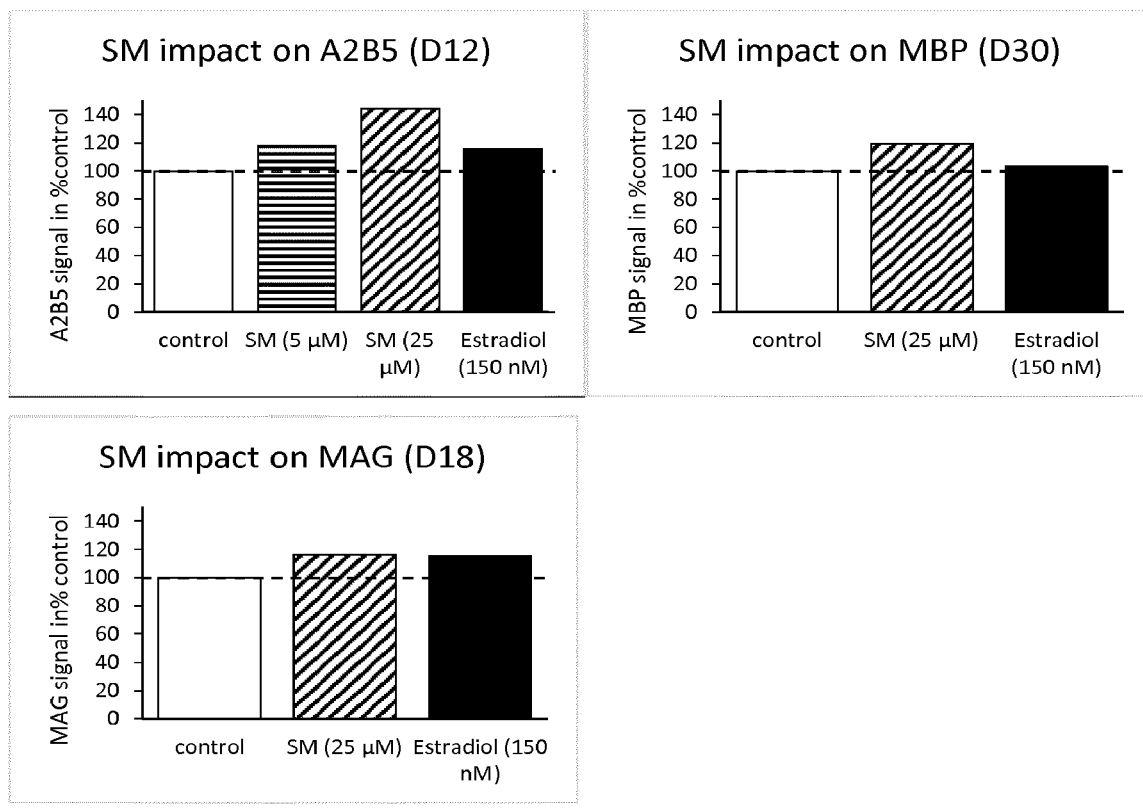
FIG. 21: Shows the impact of sphingomyelin on A2B5, MAG, and/or MBP at day 12, day 18 and/or day 30.
Figure 22:
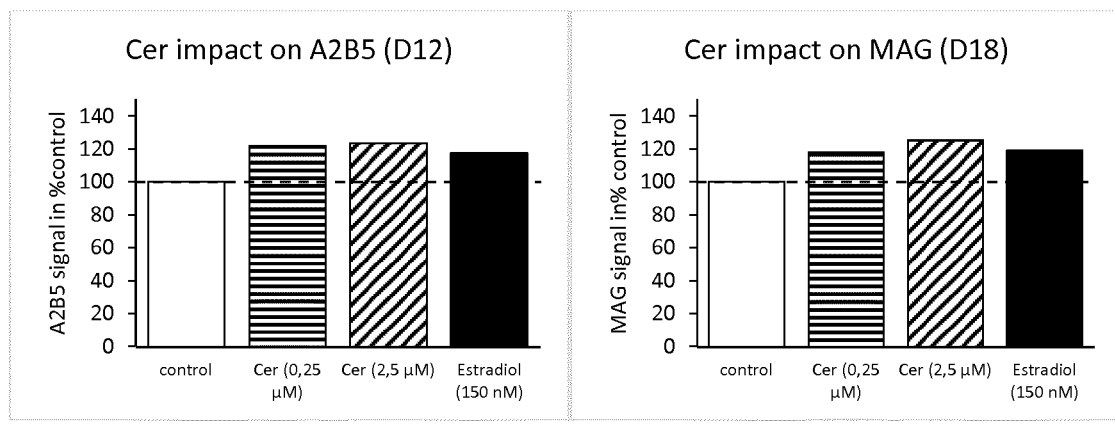
FIG. 22: Shows the impact of ceramide on A2B5 at day 12, and on MAG at day 18.
Figure 23:
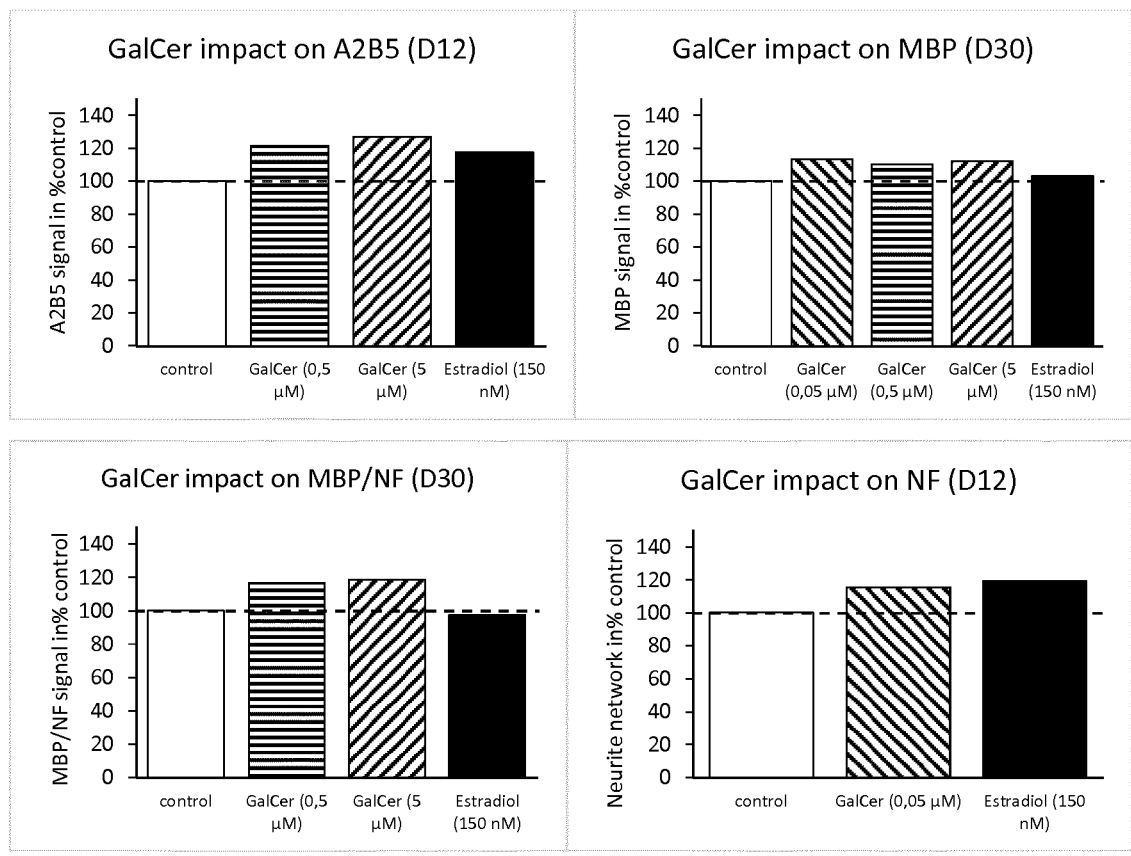
FIG. 23: Shows the impact of galactoceramide on A2B5, MBP, NF, and/or MBP/NF at day 12 and/or day 30.
Figure 24:
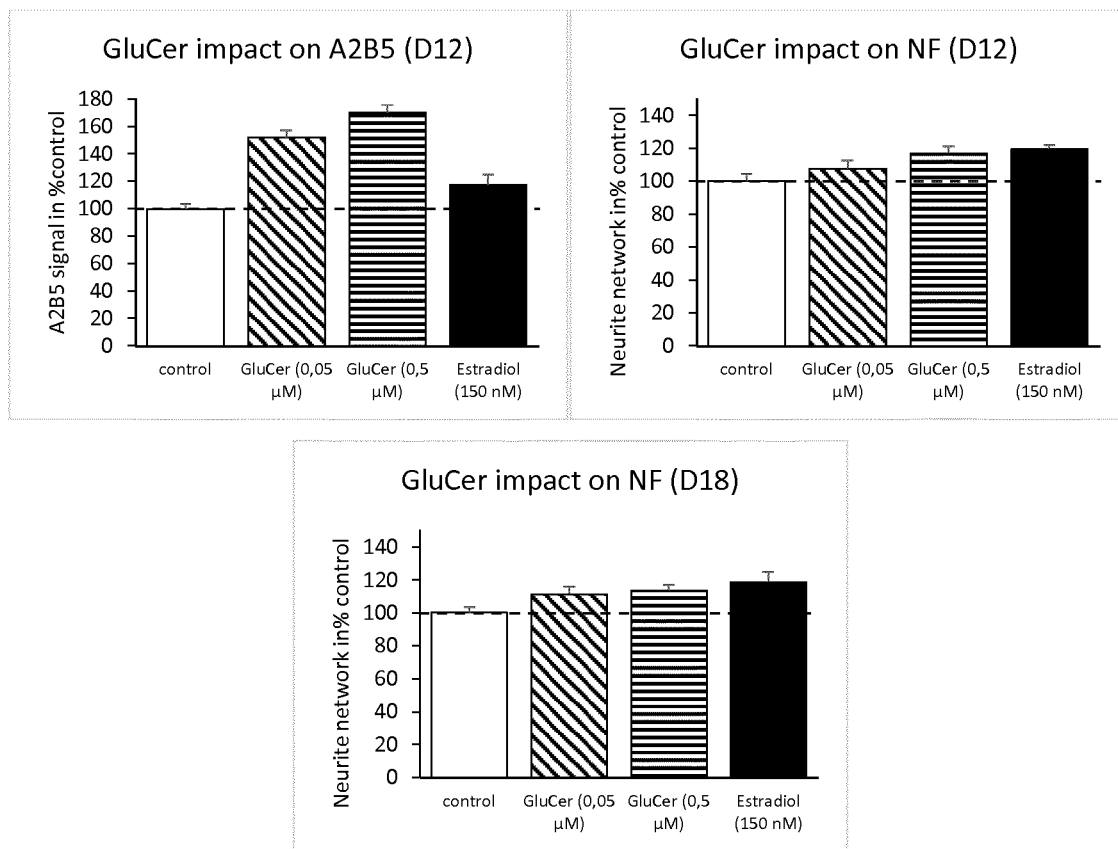
FIG. 24: Shows the impact of glucoceramide on A2B5 at day 12 and NF at day 12 and day 18.
Figure 25:
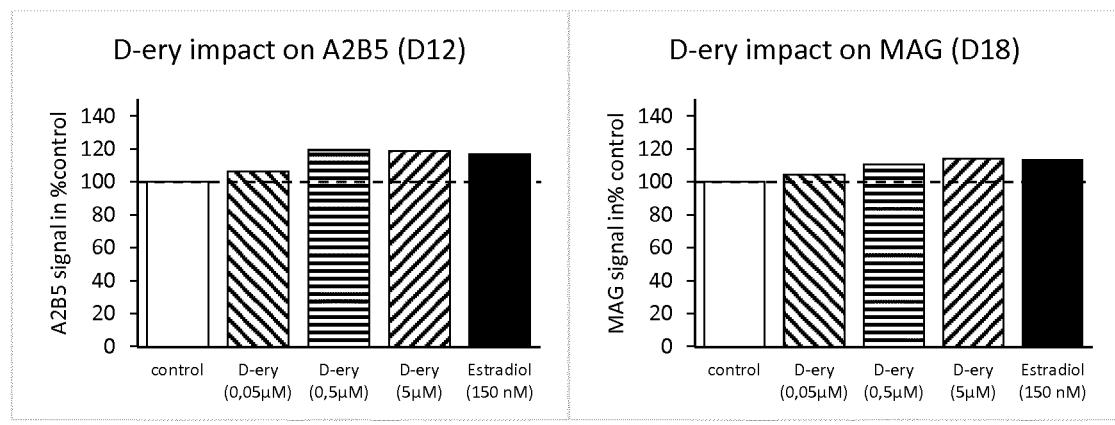
FIG. 25: Shows the impact of D-erythroceramide on A2B5 at day 12 and on MAG at day 18.
Figure 26:
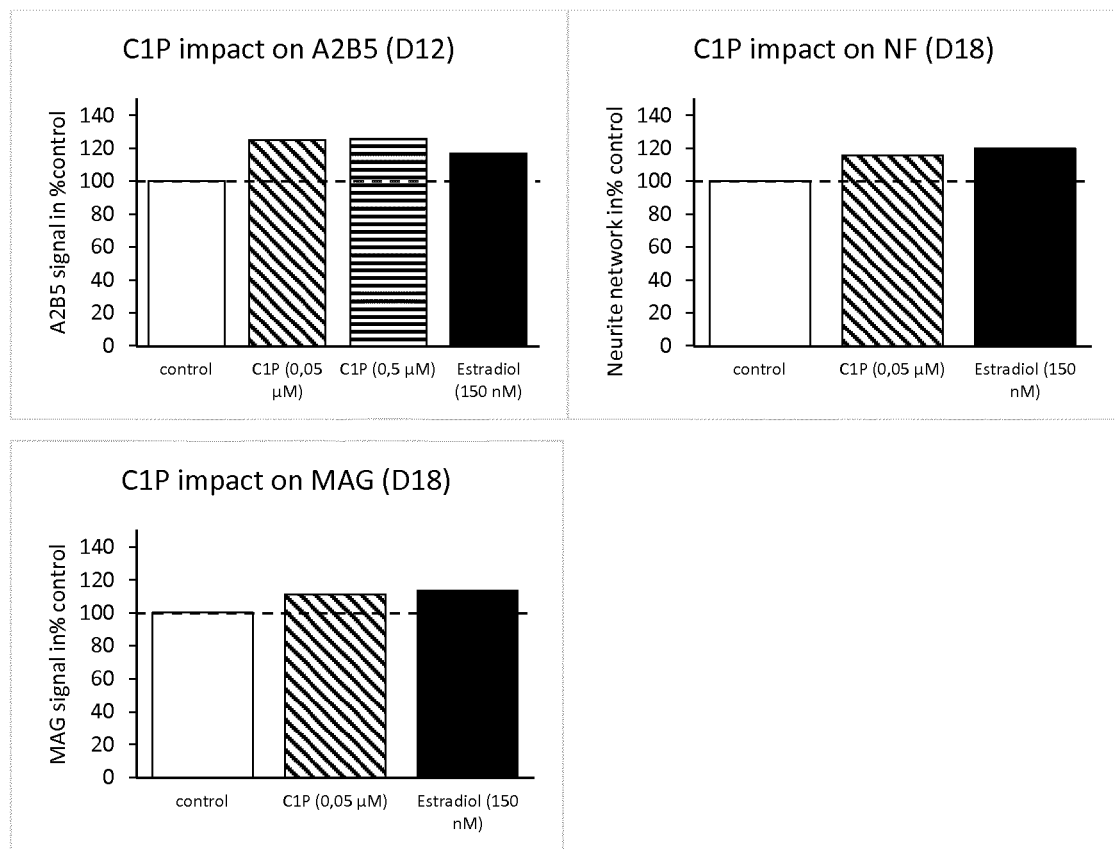
FIG. 26: Shows the impact of Ceramide-1-phosphate on A2B5 at day 12, and on NF and MAG at day 18.
Figure 27:
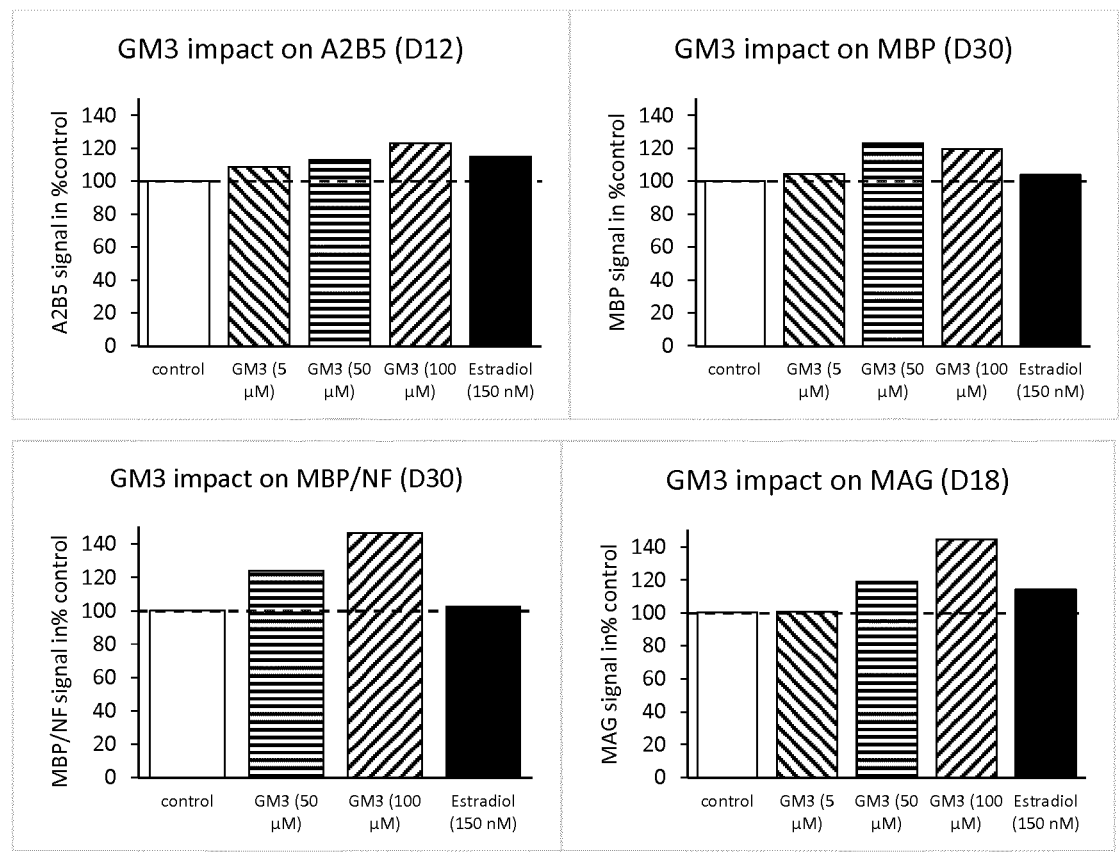
FIG. 27: Shows the impact of monosialoganglioside-3 (GM3) on A2B5, MBP, MAG, and/or MBP/NF at day 12, day 18 and/or day 30.
Figure 28:
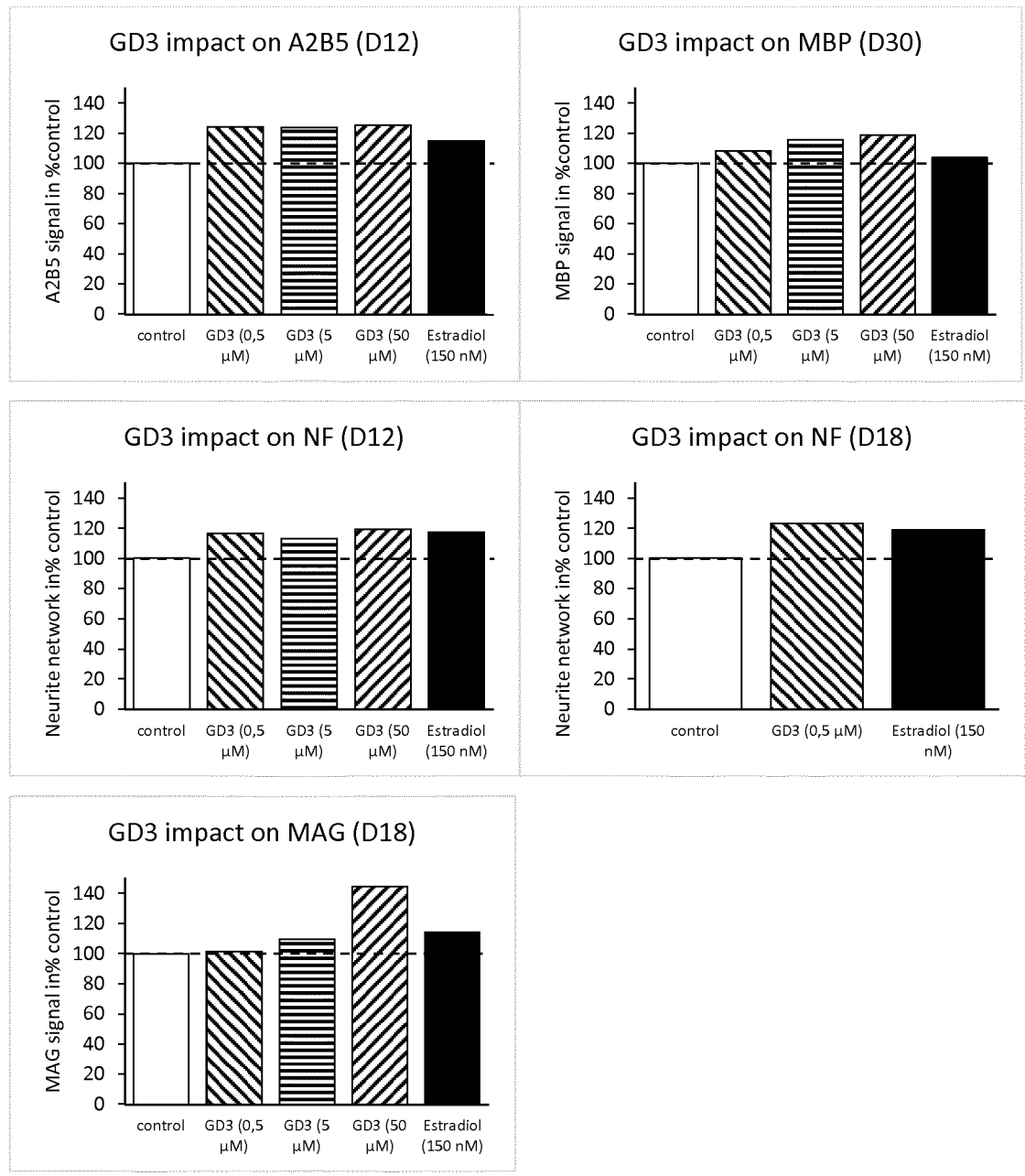
FIG. 28: Shows the impact of disialogangliosides 3 (GD3) on A2B5, MBP, NF and/or MAG at day 12, day 18 and/or day 30.
Figure 29:
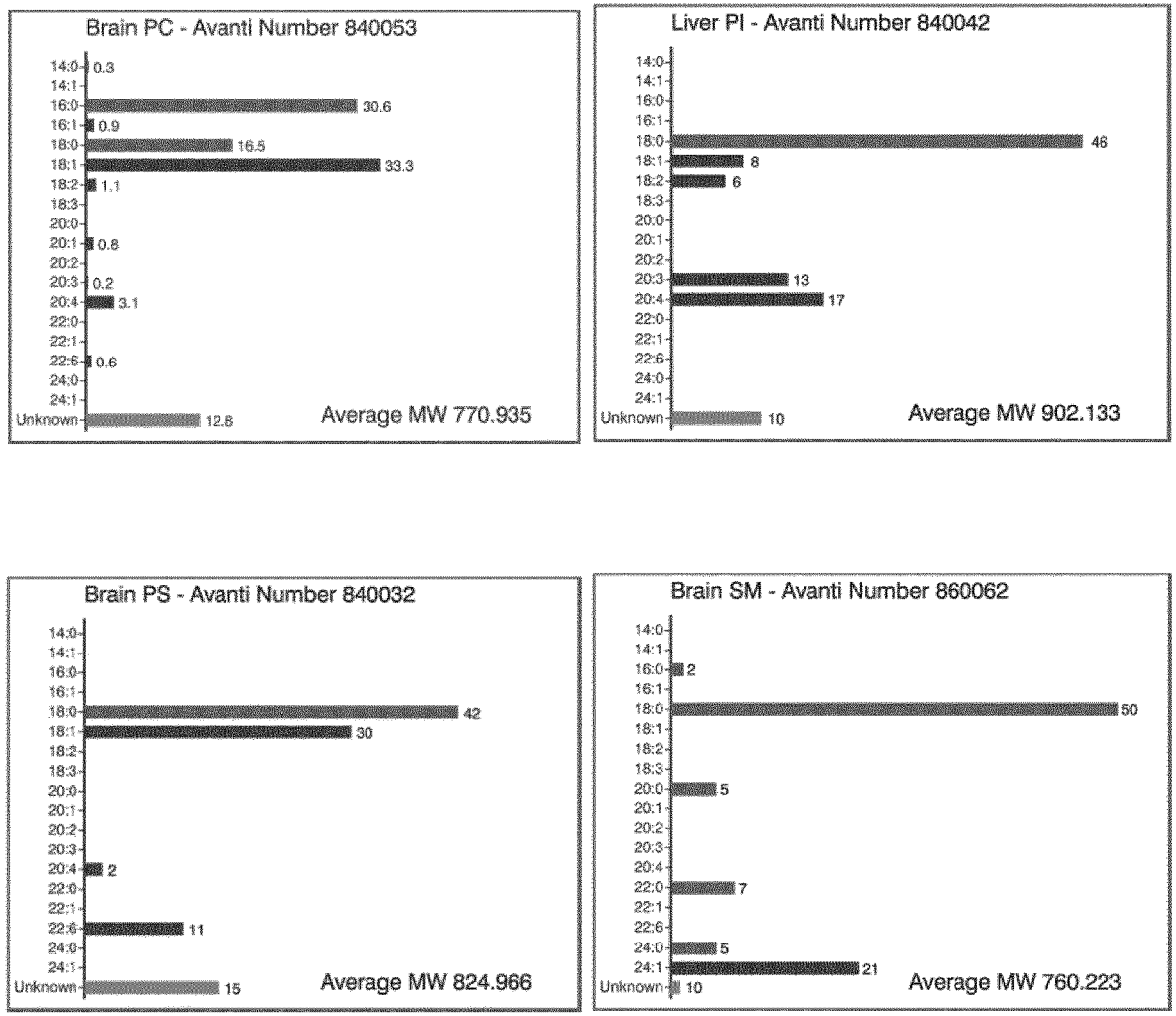
FIG. 29: Shows the fatty acid profile of Phosphatidylinositol (PI), Phosphatidylcholine, Phosphatidyl (PC), Phosphatidylserine (PS), and Sphingomyelin used in example 6.
Figure 30:
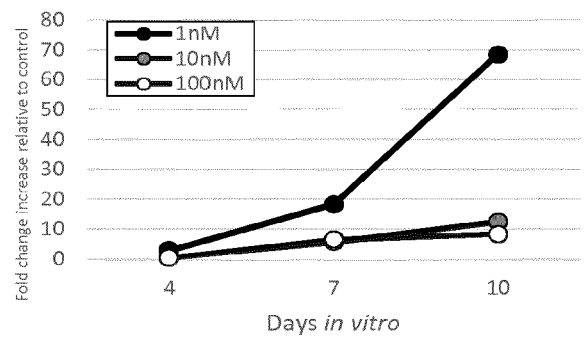
FIG. 30: Shows the impact of vitamin B12 on MAG and MBP mRNA expression and on MBP and BetaIII Co-expression.
Figure 30:
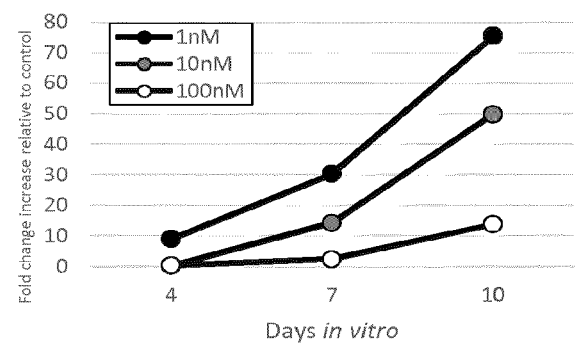
Figure 30:
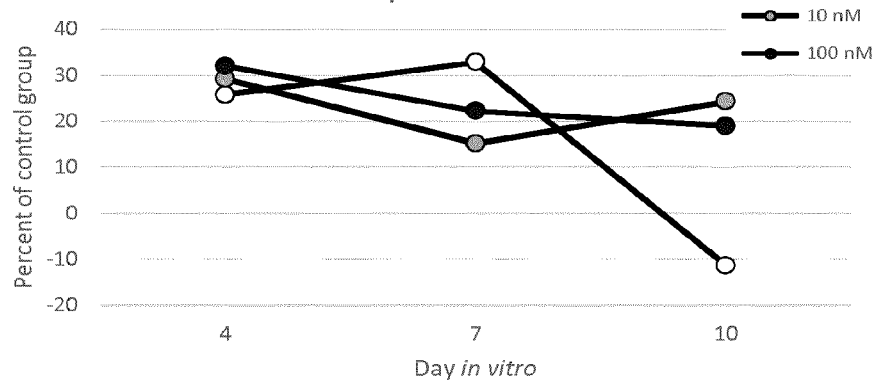
Figure 31:
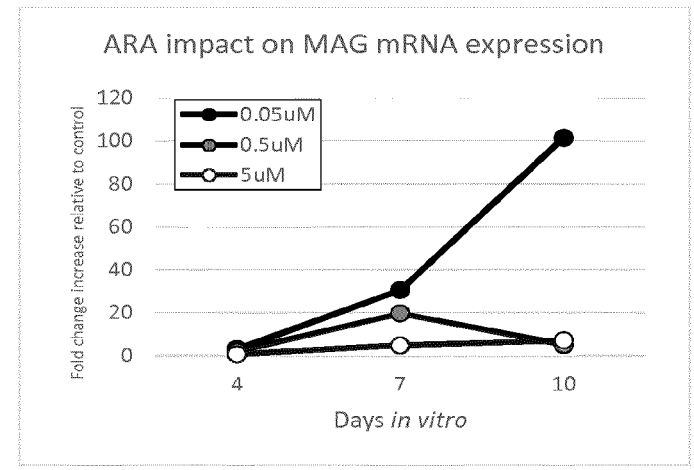
FIG. 31: Shows the impact of ARA on MAG and MBP mRNA expression and on MBP and BetaIII Co-expression.
Figure 31:
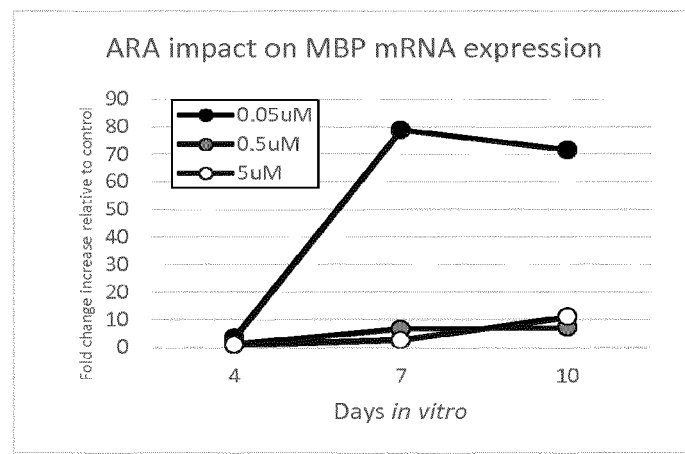
Figure 31:
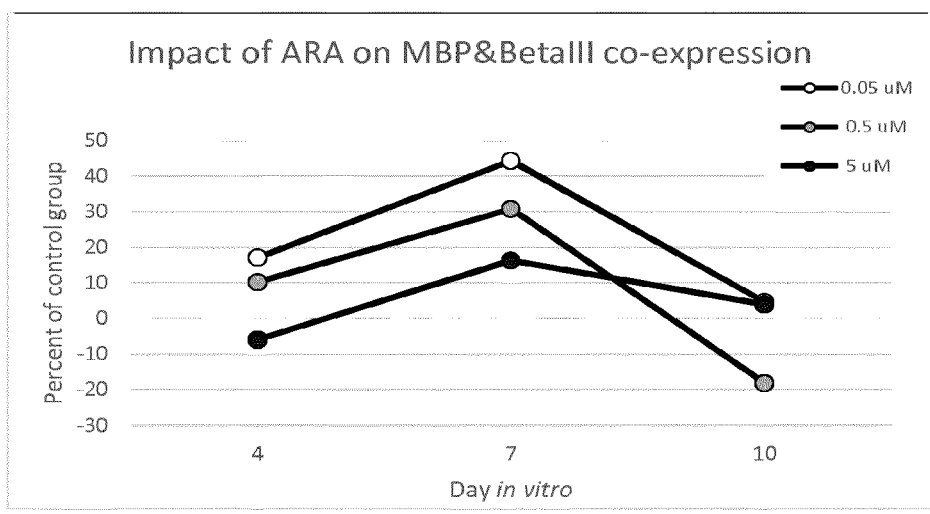
Figure 32:
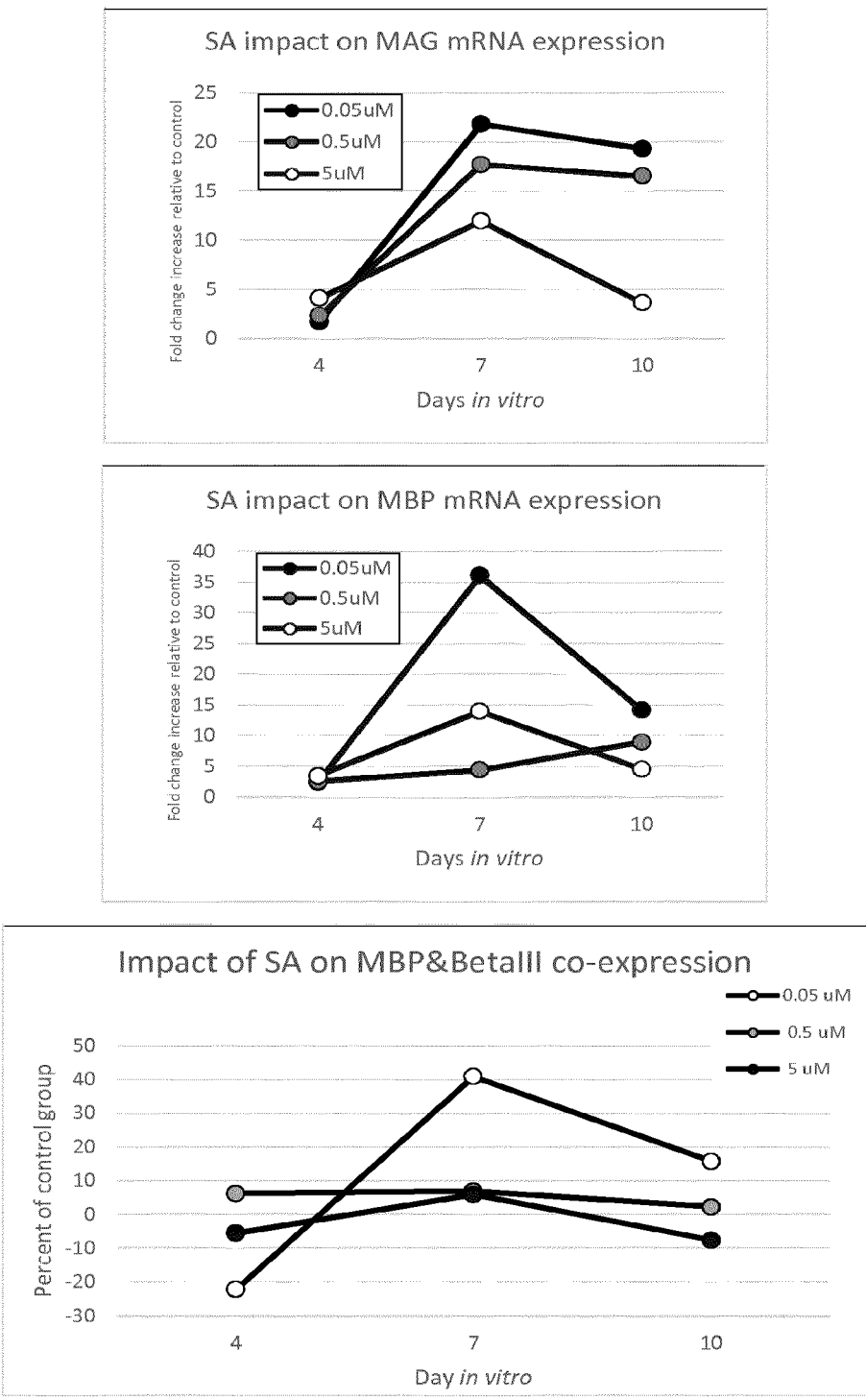
FIG. 32: Shows the impact of stearic acid on MAG and MBP mRNA expression and on MBP and BetaIII Co-expression.
Figure 33:
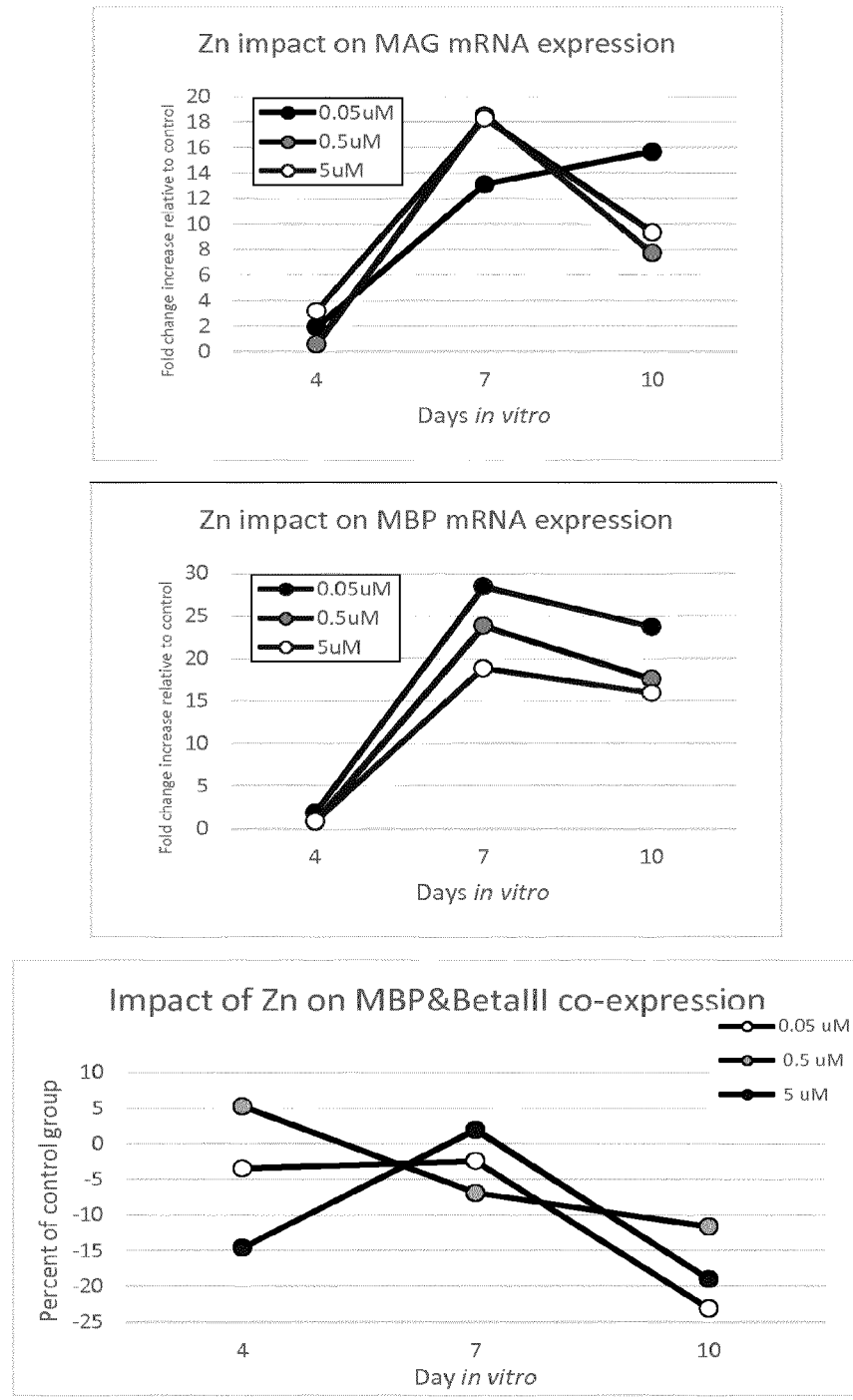
FIG. 33: Shows the impact of zinc on MAG and MBP mRNA expression and on MBP and BetaIII Co-expression.
Figure 34:
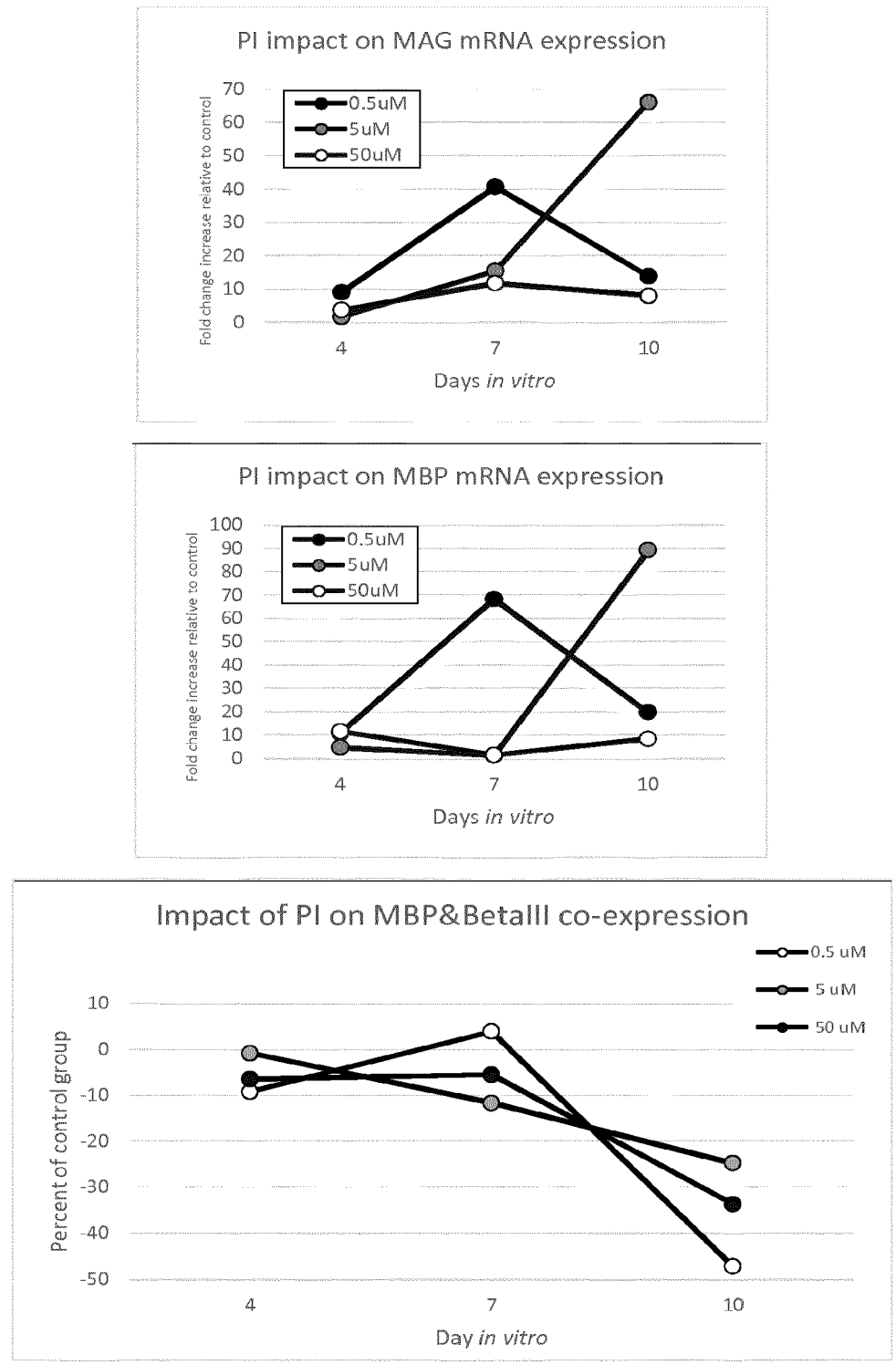
FIG. 34: Shows the impact of phosphatidylinositol on MAG and MBP mRNA expression.
Figure 35:
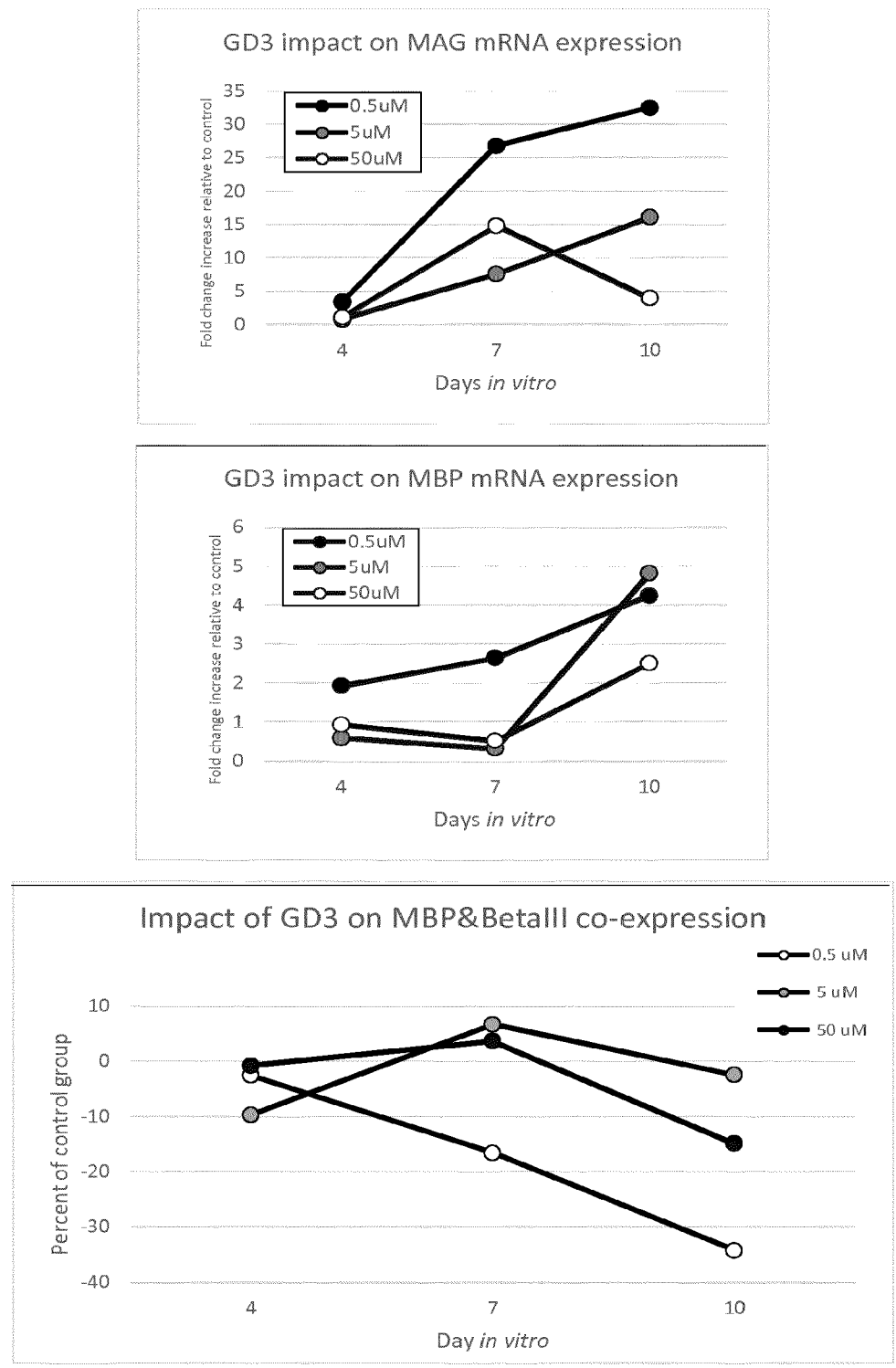
FIG. 35: Shows the impact of GD3 on MAG and MBP mRNA expression and on MBP and BetaIII Co-expression.
Figure 36:
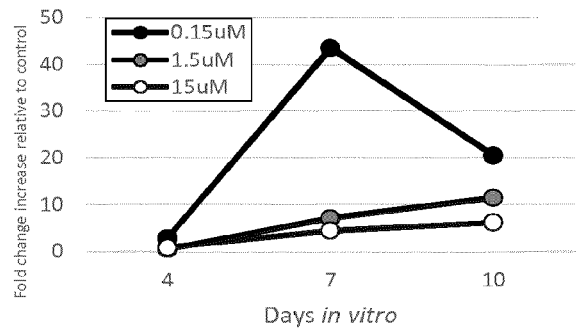
FIG. 36: Shows the impact of DHA on MAG and MBP mRNA expression and on MBP and BetaIII Co-expression.
Figure 36:
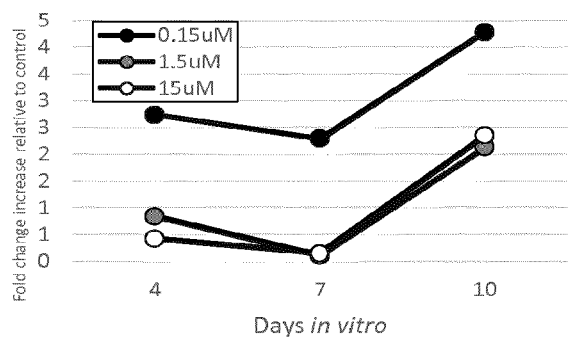
Figure 36:
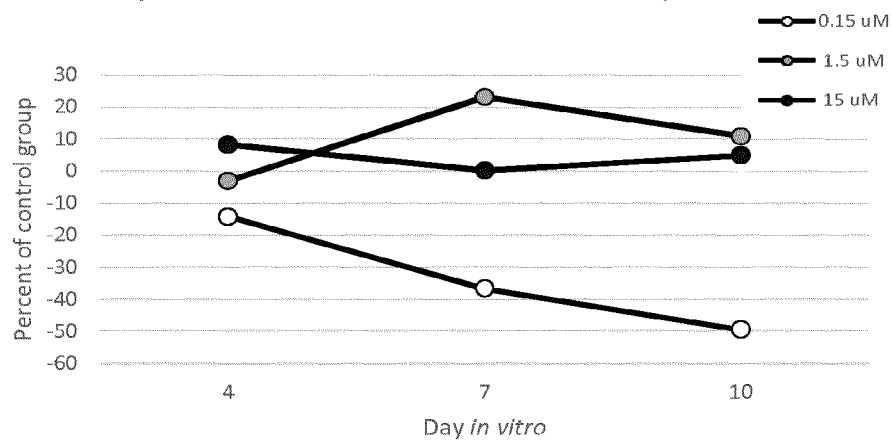
Figure 37:
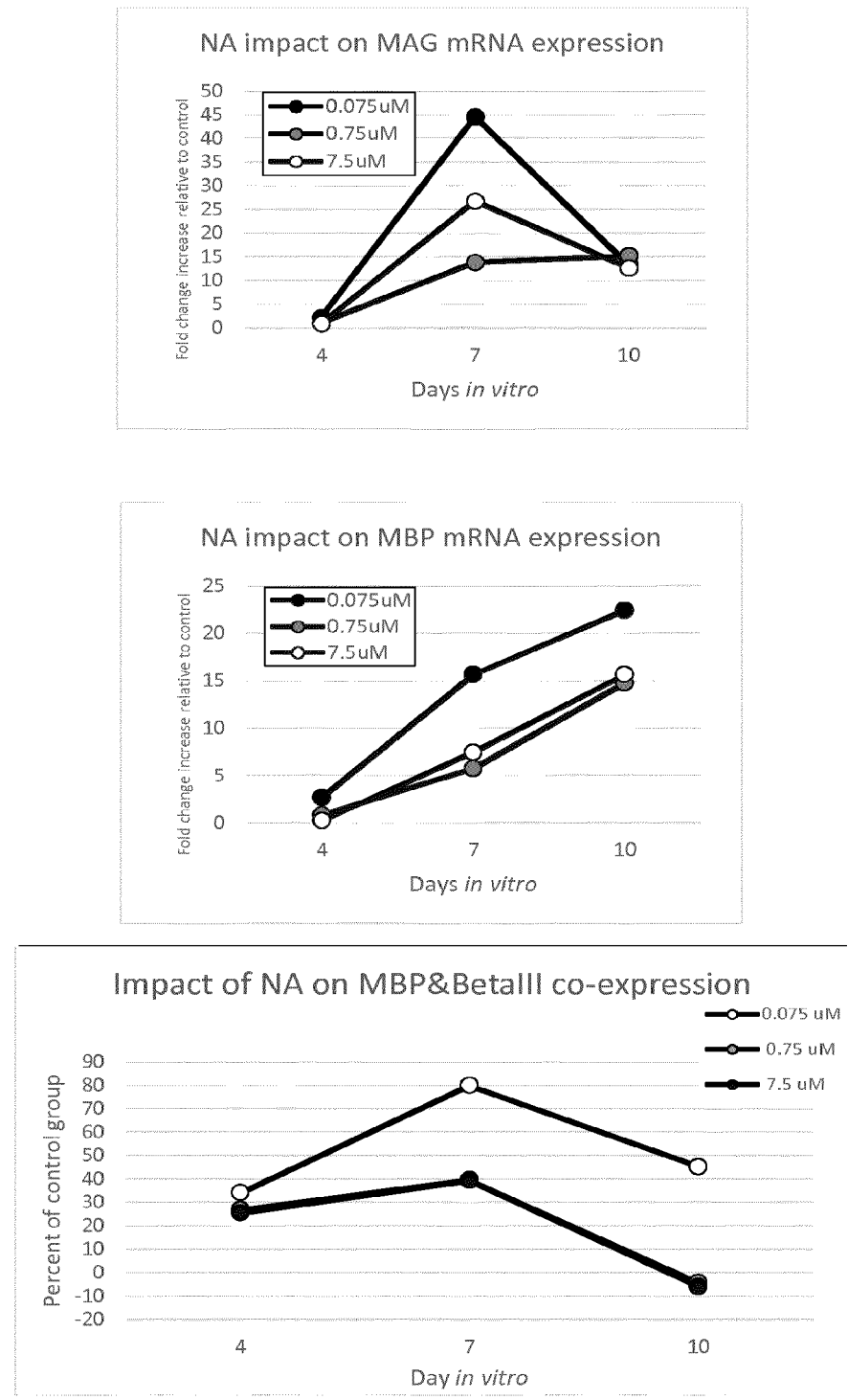
FIG. 37: Shows the impact of nervonic acid on MAG and MBP mRNA expression and on MBP and BetaIII Co-expression.
Figure 38:
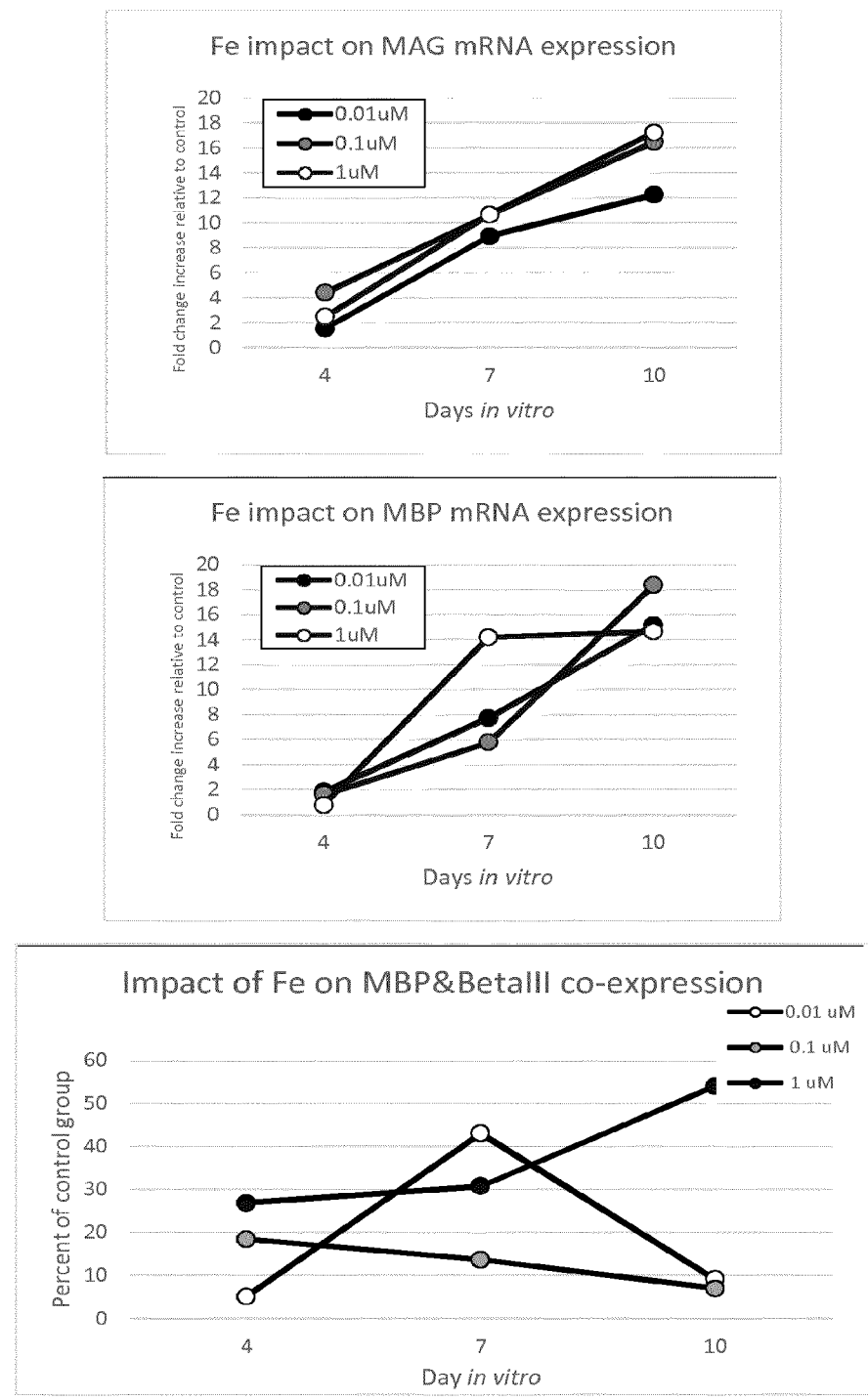
FIG. 38: Shows the impact of Iron on MAG and MBP mRNA expression and on MBP and BetaIII Co-expression.
Figure 39:
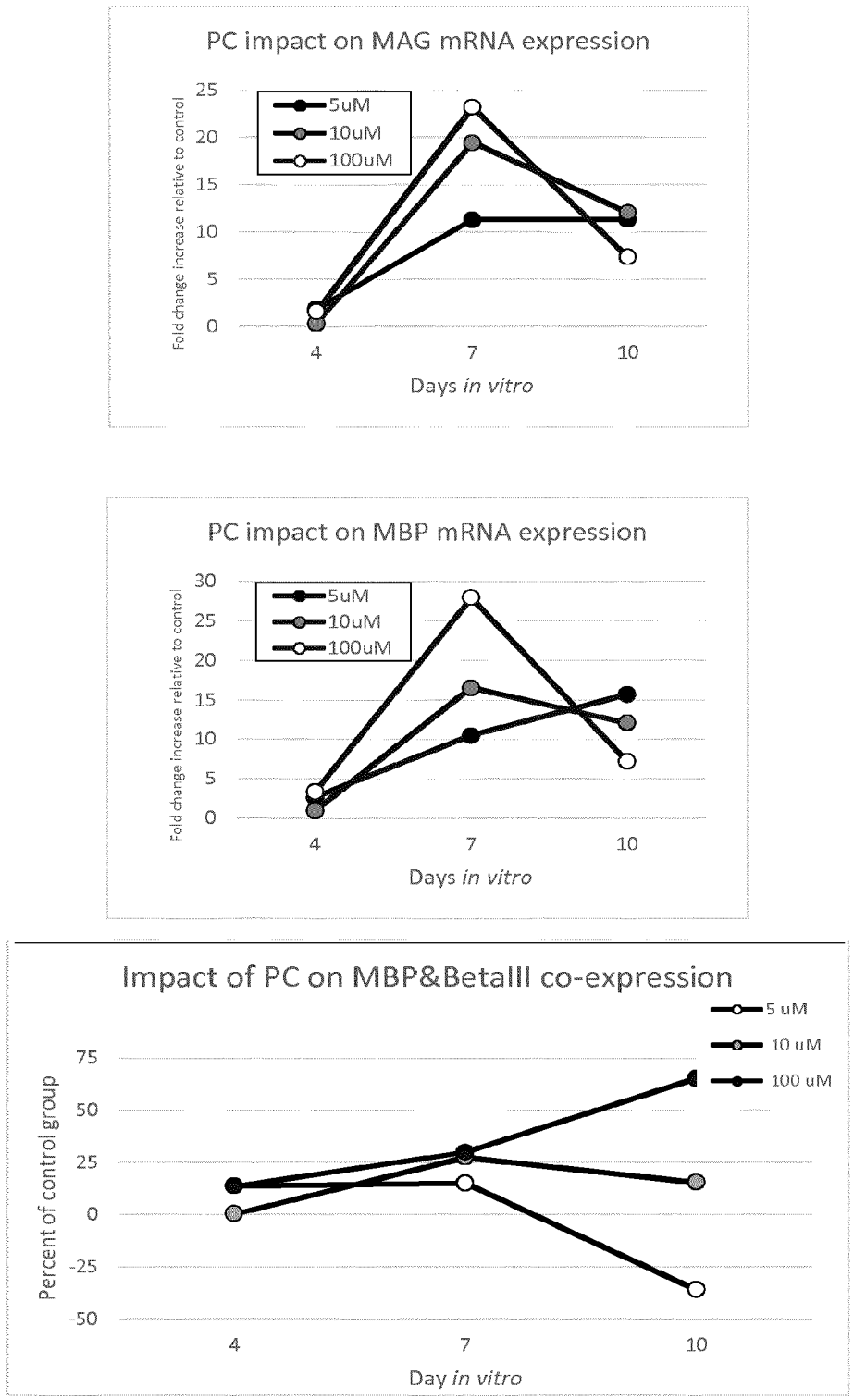
FIG. 39: Shows the impact of phosphatidylcholine on MAG and MBP mRNA expression and on MBP and BetaIII Co-expression.
Figure 40:
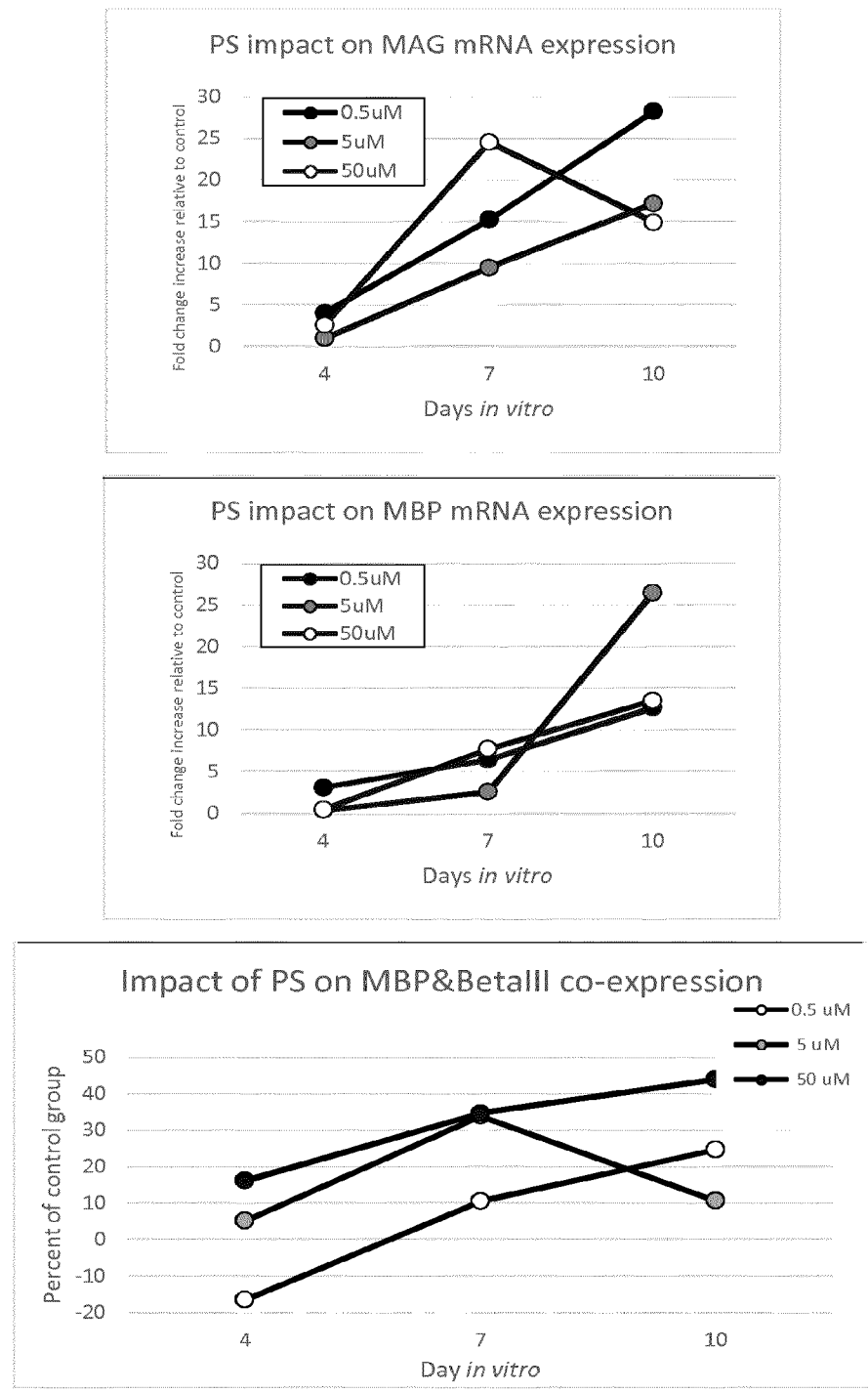
FIG. 40: Shows the impact of phosphatidylserine on MAG and MBP mRNA expression and on MBP and BetaIII Co-expression.
Figure 41:
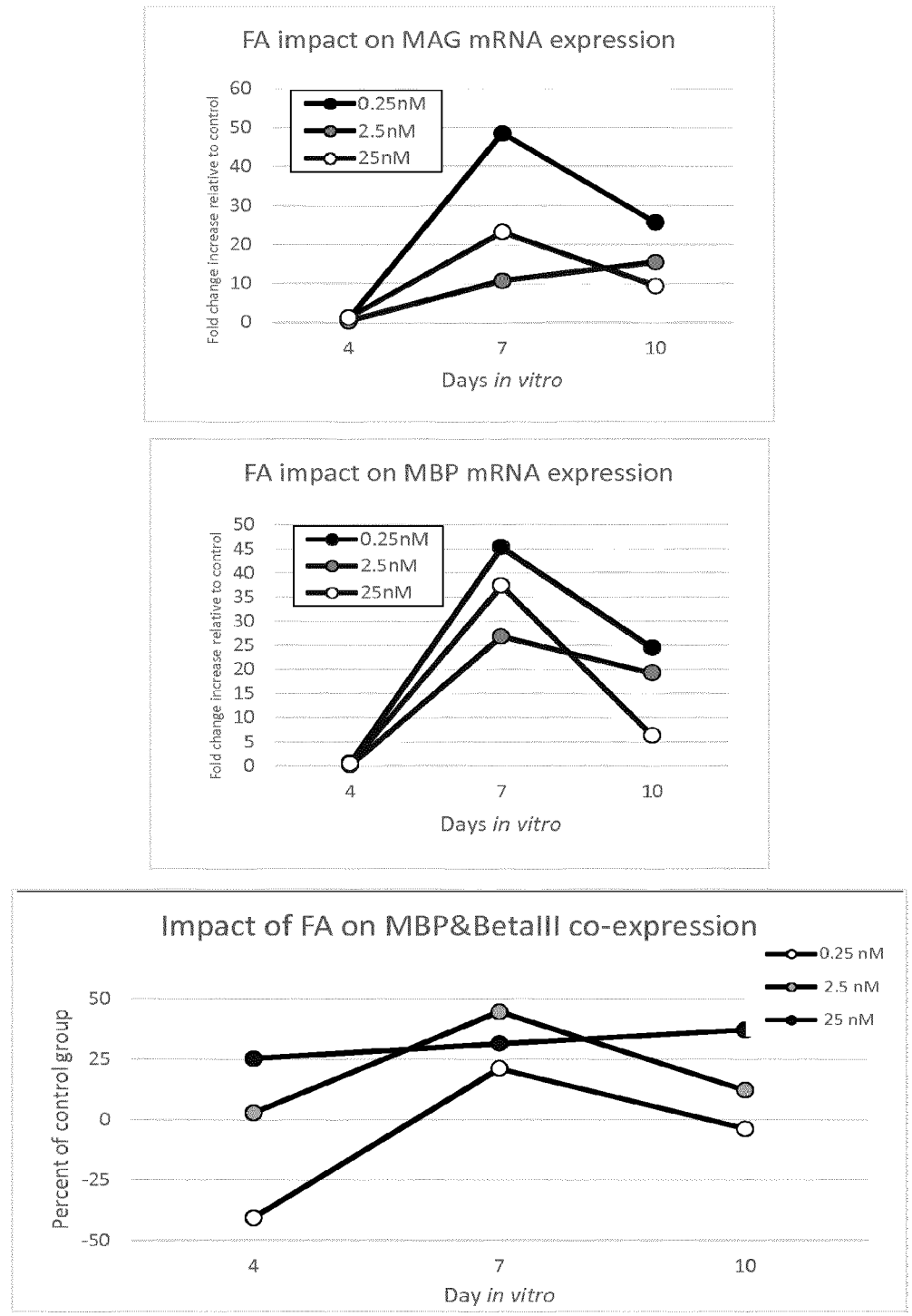
FIG. 41: Shows the impact of folic acid on MAG and MBP mRNA expression and on MBP and BetaIII Co-expression.
Figure 42:
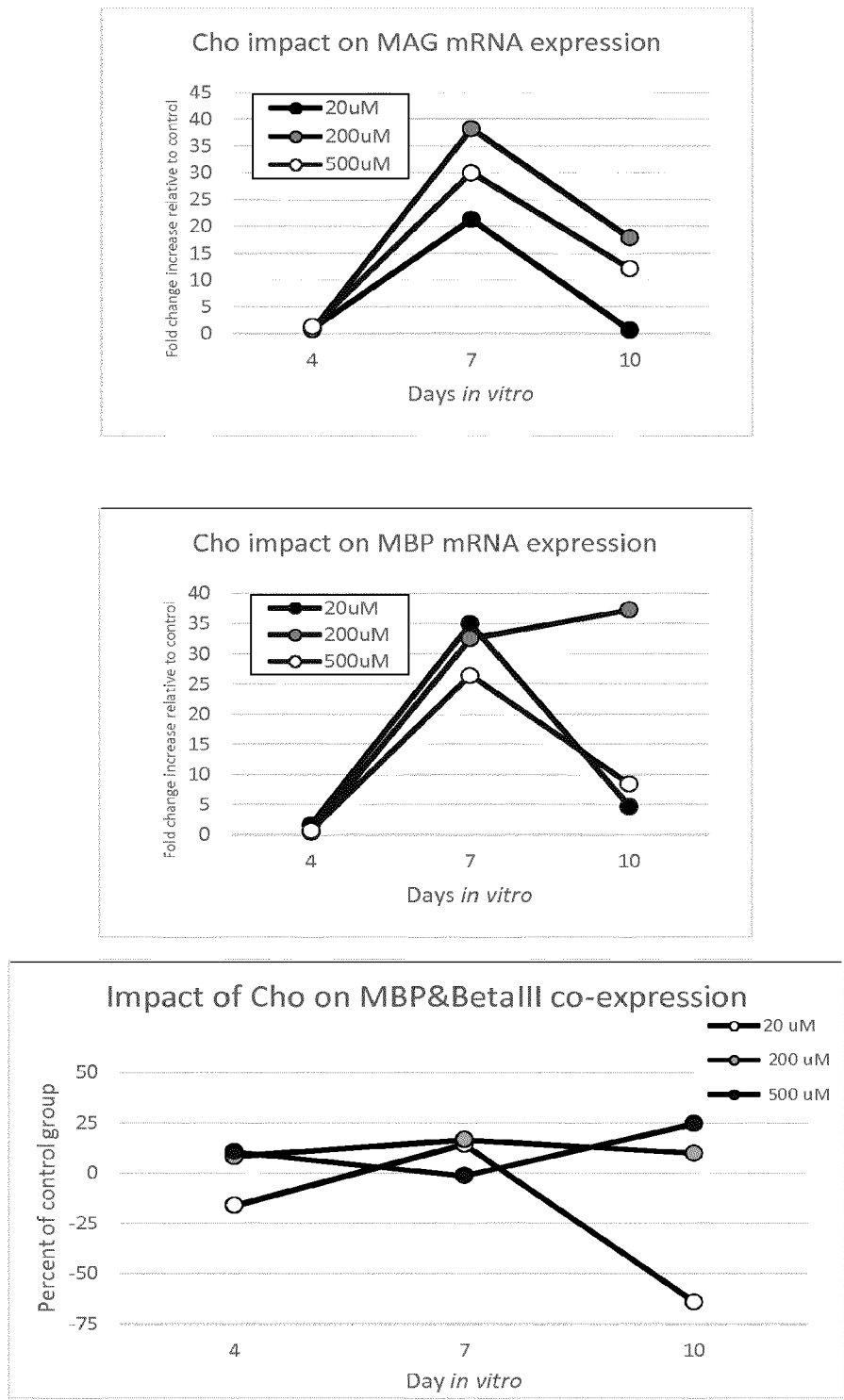
FIG. 42: Shows the impact of choline on MAG and MBP mRNA expression and on MBP and BetaIII Co-expression.
Figure 43:
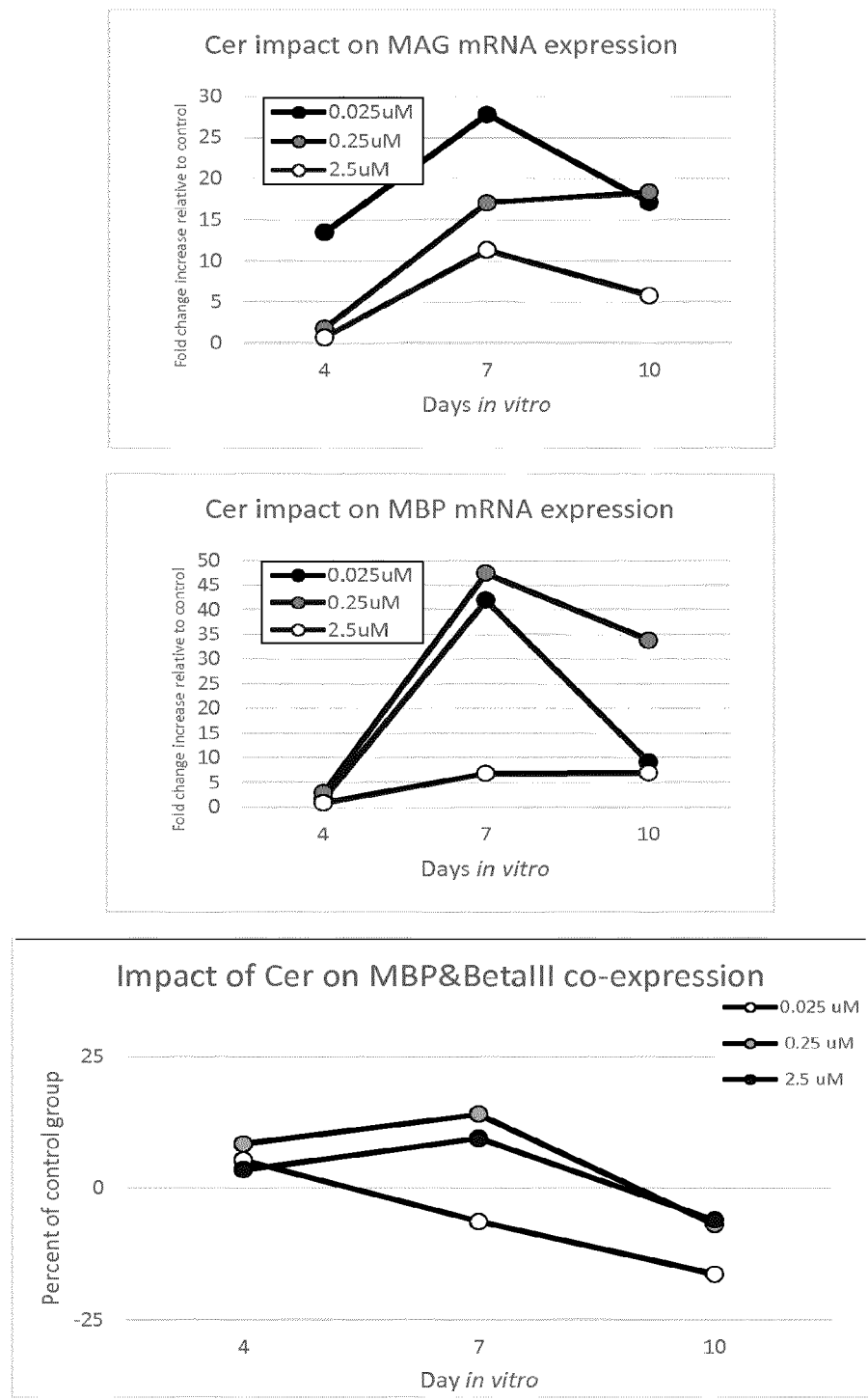
FIG. 43: Shows the impact of ceramide on MAG and MBP mRNA expression and on MBP and BetaIII Co-expression.
Figure 44:
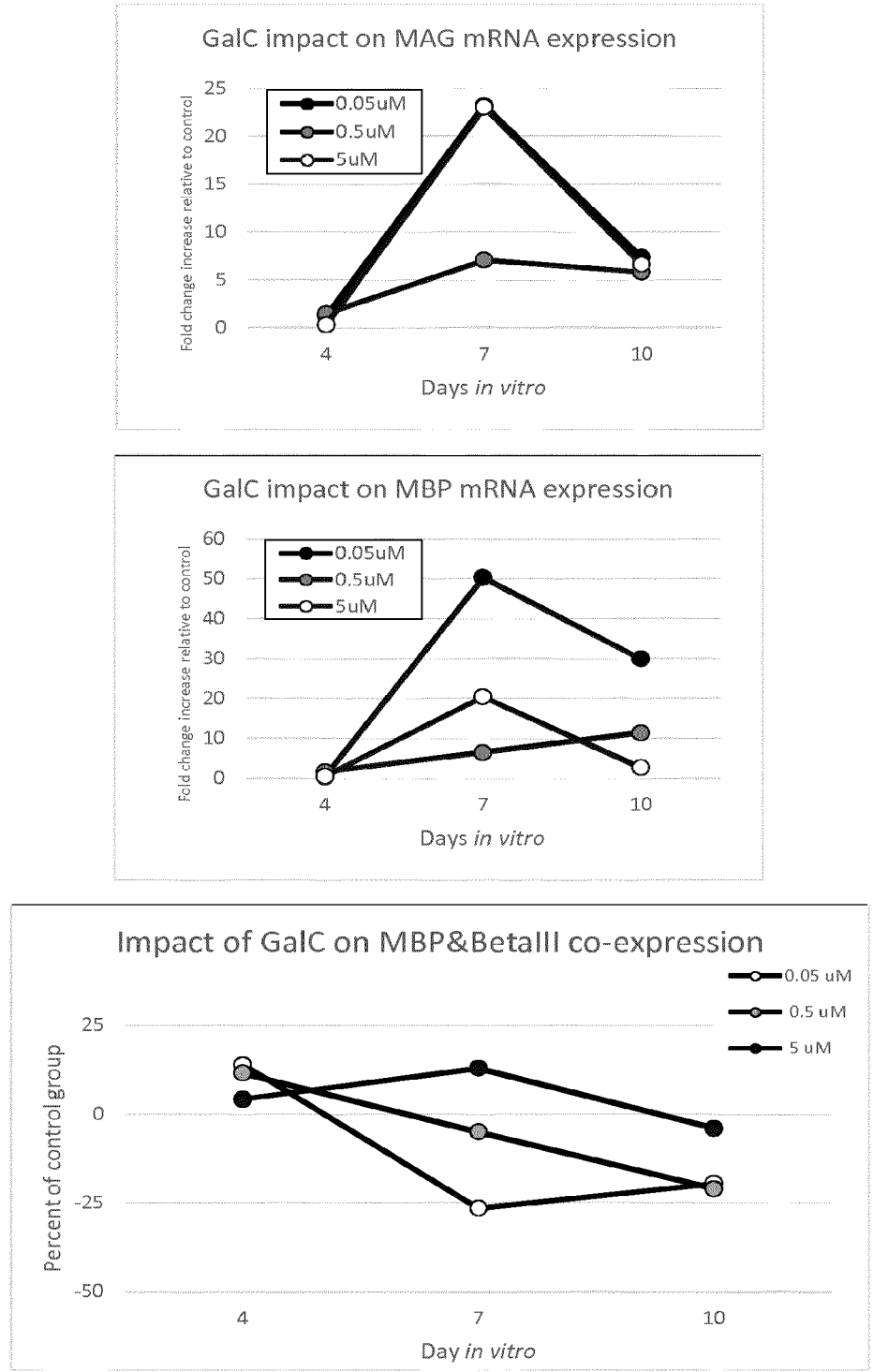
FIG. 44: Shows the impact of galactoceramide on MAG and MBP mRNA expression and on MBP and BetaIII Co-expression.
Figure 45:
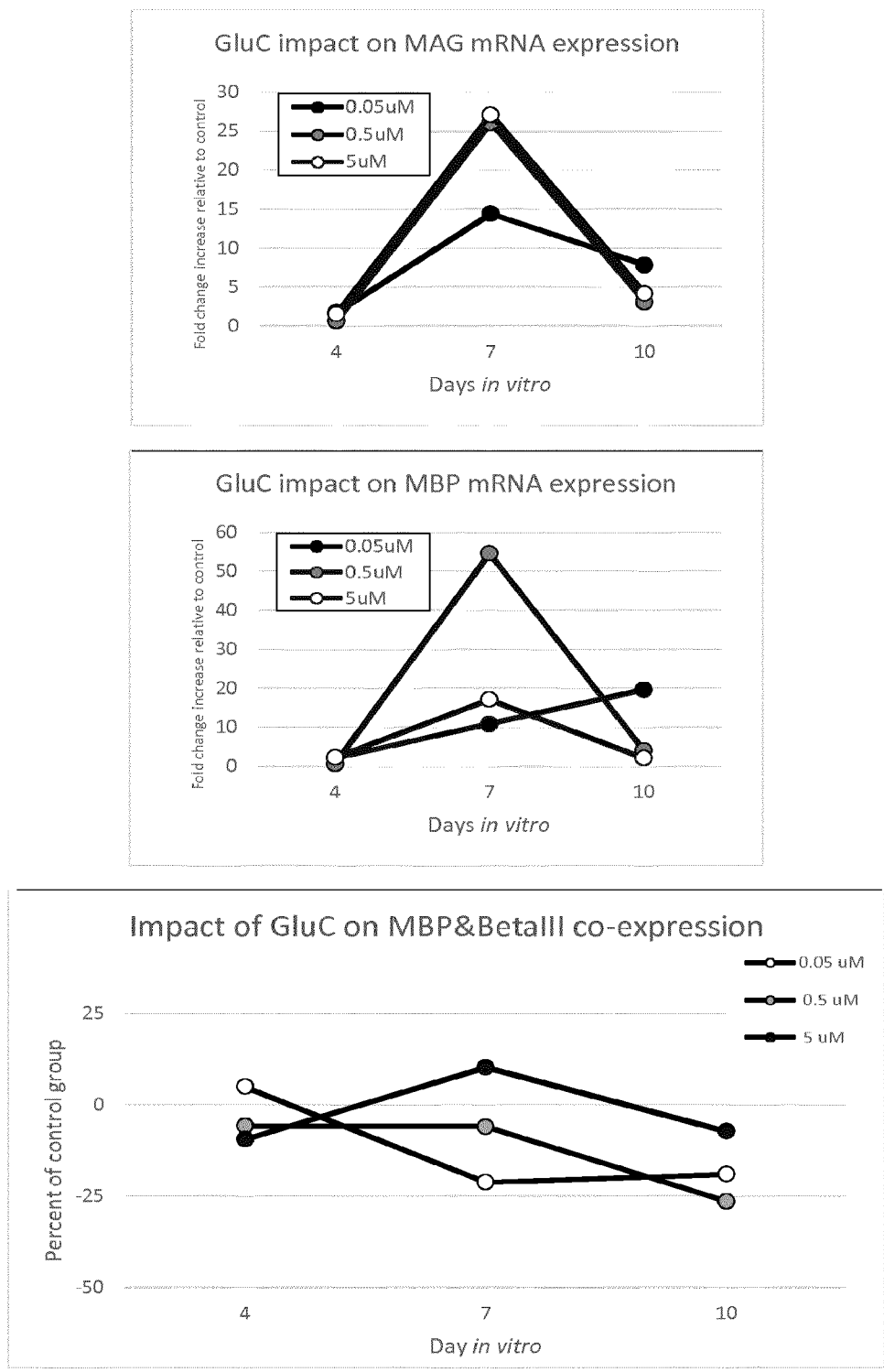
FIG. 45: Shows the impact of glucoceramide on MAG and MBP mRNA expression and on MBP and BetaIII Co-expression.
Figure 46:
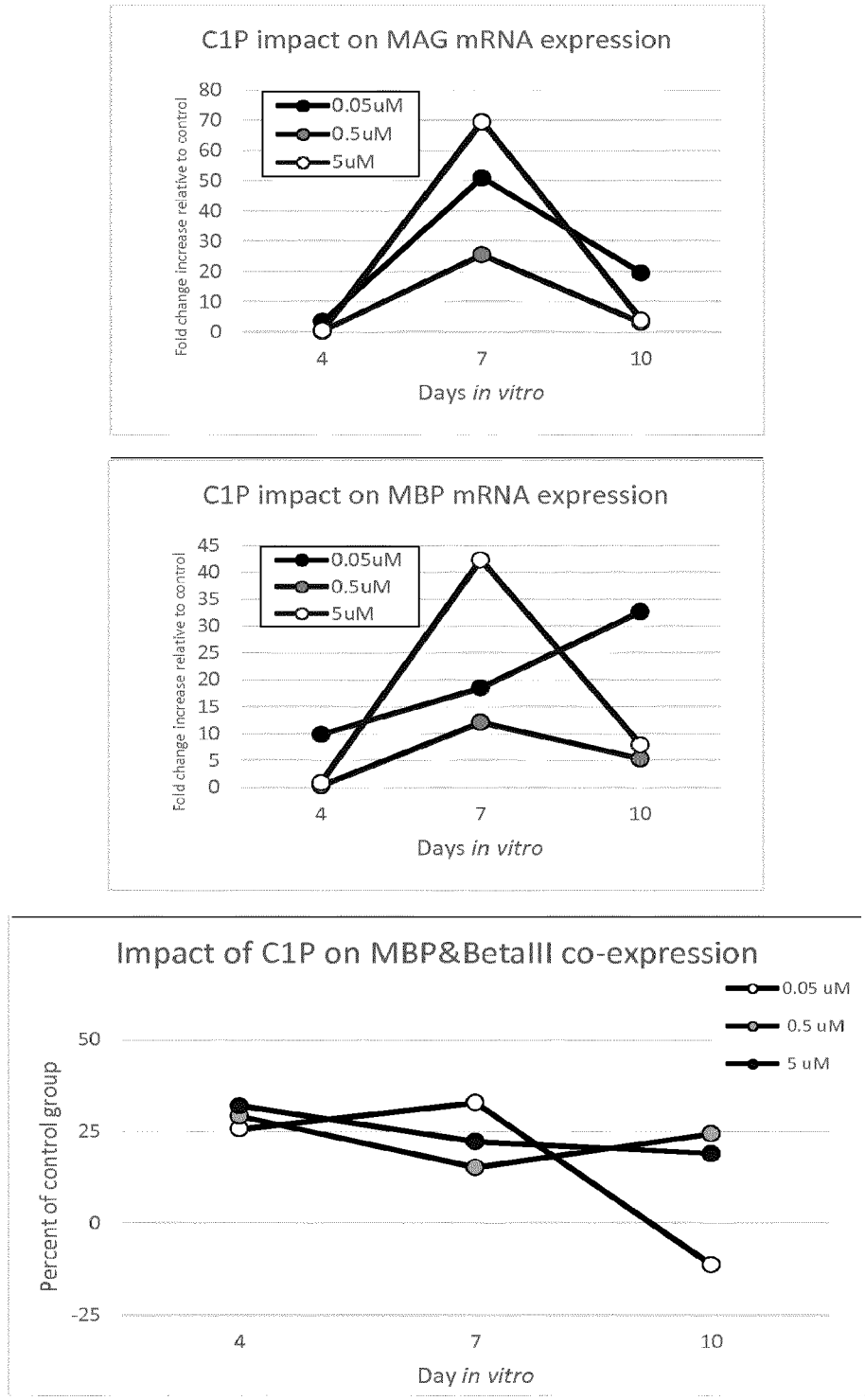
FIG. 46: Shows the impact of Ceramide-1-phosphate on MAG and MBP mRNA expression and on MBP and BetaIII Co-expression.
Figure 47:
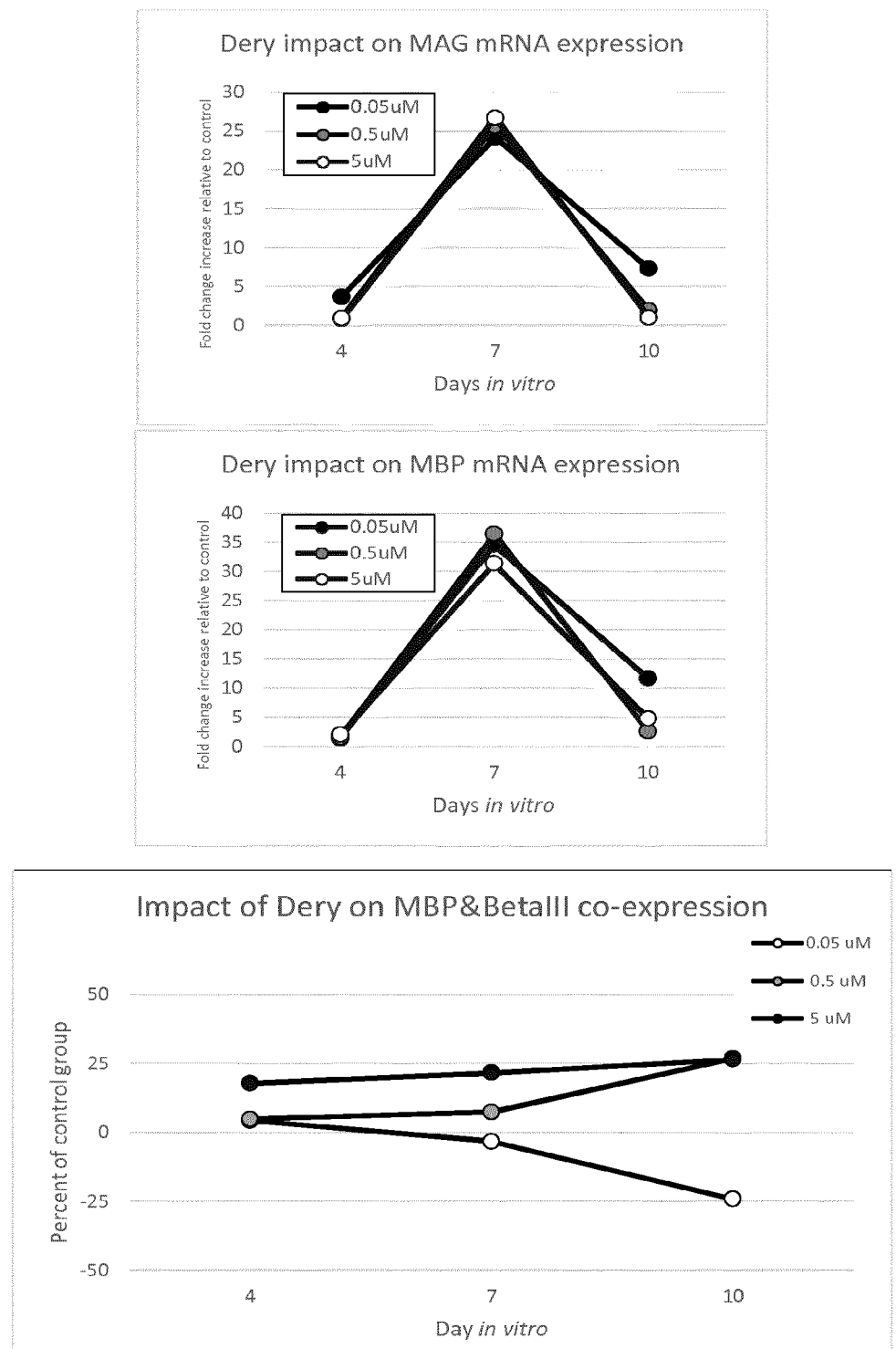
FIG. 47: Shows the impact of D-erythroceramide on MAG and MBP mRNA expression and on MBP and BetaIII Co-expression.
Figure 48:
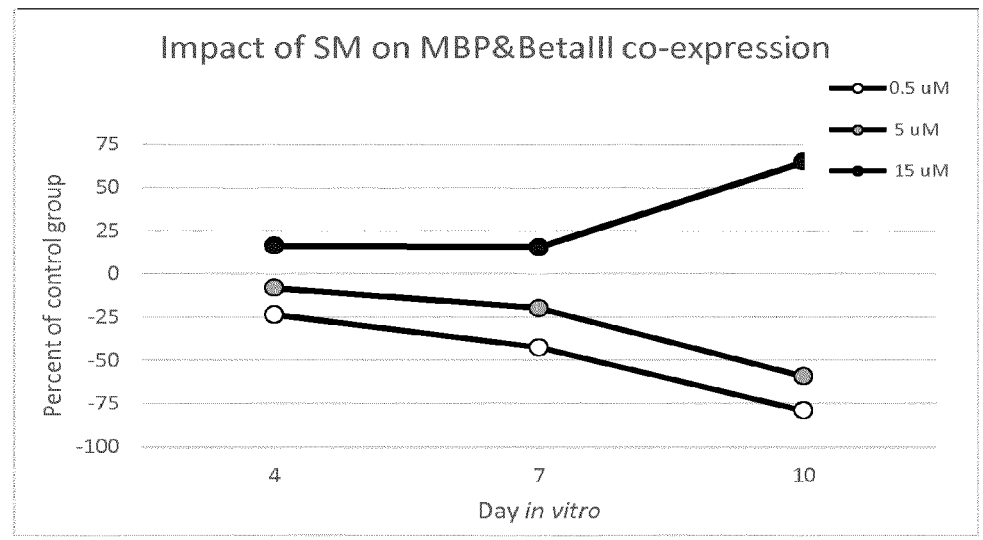
FIG. 48: Shows the impact of sphingomyelin on MBP and BetaIII Co-expression.
Figure 49:
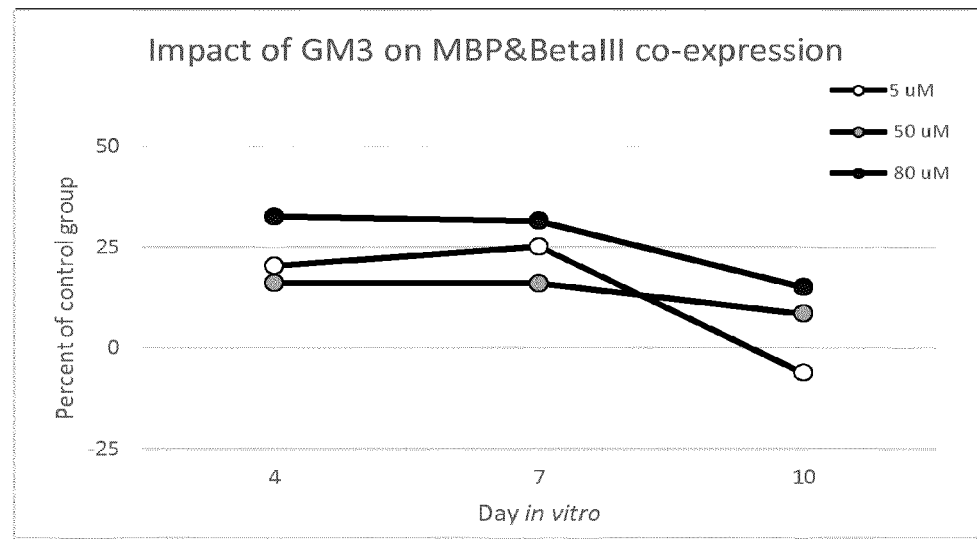
FIG. 49: Shows the impact of GM3 on MBP and BetaIII Co-expression.
Figure 50:
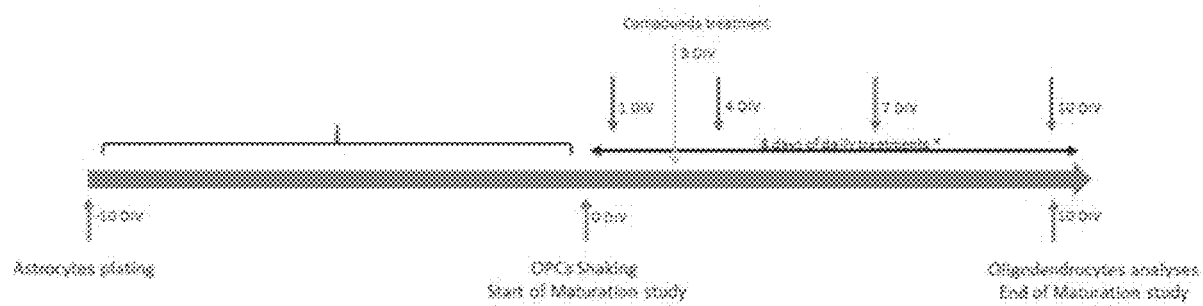
FIG. 50: Shows the experimental procedure for maturation experiments.
Figure 51:
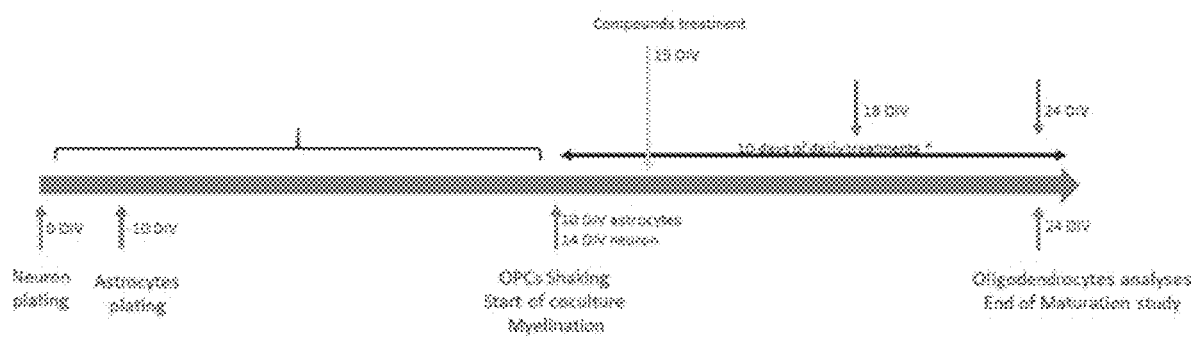
FIG. 51: Shows the experimental procedure for myelination experiments.

As shown in FIG. 7, SM fraction contained mostly saturated FAs (i.e. myristic acid 14:0, pentadecylic acid 15:0, palmitic acid 16:0, stearic acid 18:0, arachidic acid 20:0, behenic acid 22:0, tricosylic acid 23:0 and lignoceric acid 24:0). A higher proportion of SFA was observed in SM fraction from all milk products (Table 9). This is in agreement with literature, revealing high distribution of SFA with carbon chain higher than 18 in SM fraction. This high amount of SFA reflects the structural role of SM, namely lessen fluidity and maintain rigidity of the milk fat globule membrane.

TABLE 9

Percentage of SFA, MUFA and PUFA detected in SM fraction from different milk products.

| | FA | Ingredient | Infant Formula | Cow's Milk | Human Milk |
|---|---|---|---|---|---|
| SFA % | 14:0-16:0; 18:0; 20:0-24:0 | 95.1 ± 2.6 | 92.8 ± 3.9 | 93.1 ± 8.4 | 87.9 ± 2.7 |
| MUFA % | 18:1n-9 | 2.5 ± 0.7 | 3.6 ± 0.9 | 5.3 ± 1.5 | 4.4 ± 1.9 |
| | 24:1n-9 | 1.7 ± 0.3 | 1.9 ± 1.7 | 1.2 ± 0.1 | 5.9 ± 0.6 |
| PUFA % | 18:2n-6 | 0.8 ± 0.4 | 1.7 ± 0.2 | 0.3 ± 0.4 | 1.7 ± 0.1 |

Monounsaturated FAs (MUFAs) represented about 4-11% of the FA in the SM fraction. Oleic acid 18:1n-9 and nervonic acid 24:1n-9 were the 2 MUFAs detected. Interestingly, 24:1n-9 was found in relative higher proportion in human milk compared to the other milk products and this is in agreement with the literature. The only PUFA linoleic acid 18:2n-6 was found relatively higher in the tested infant formula and human milk compared to the other products. Finally, omega-3 PUFAs were not detected in SM fraction. This is also in accordance with data found in the literature showing that arachidonic acid (AA, 20:4n-6), eicosapentaenoic acid (EPA, 20:5n-3) and docosahexaenoic acid (DHA, 22:6n-3) are mainly present in PE, PI and PS.

Example 5

Examples of synthetic nutritional compositions (infant formulas) in accordance with the invention are set out in Table 10 and table 10a

TABLE 10

Nutrition infomation

| nutritional constituents | Unit | per 100 g |
|---|---|---|
| Energy | kJ | 2216 |
| Protein | g | 11 |
| whey protein | g | 7.0 |
| α-lactalbumin | g | 1.8 |
| Casein | g | 3.8 |
| fat | g | 29 |
| linoleic acid | mg | 4160 |
| α-Linolenic acid | mg | 336 |
| AA | mg | 203 |
| DHA | mg | 143 |
| Carbohydrates | g | 52.5 |
| Dietary fiber | g | 2.4 |
| ) Soluble Dietary Fiber (as Oligofuctose) | g | 2.4 |
| Taurine | mg | 38 |
| L-carnitine | mg | 8.0 |
| lutein | μg | 64 |
| nucleotides | mg | 21 |
| L-Tyr | mg | ≥407.4 |
| L-Trp | mg | ≥176.9 |
| VitaminA | μg retinol equivalent | 581 |
| β-carotene | μg | 120 |
| VitaminD | μg | 9.6 |
| VitaminE | mgα-tocopheryl equivalent | 5.9 |
| Vitamin K1 | μg | 54 |
| VitaminB1 | μg | 800 |
| VitaminB2 | μg | 880 |
| VitaminB6 | μg | 440 |
| VitaminB12 | μg | 9.5 |
| Niacin | μg | 4000 |
| folic acid | μg | 346 |
| pantothenic acid | μg | 2800 |
| biotin | μg | 16 |
| VitaminC | mg | 72 |

TABLE 10-continued

Nutrition infomation

| nutritional constituents | Unit | per 100 g |
|---|---|---|
| choline | mg | 230 |
| inositol | mg | 36 |
| Calcium | mg | 288-588 |
| Phosphorous | mg | 160-336 |
| Magnesium | mg | 36 |
| Iron | mg | 13.1 |
| Zinc | mg | 7.1 |
| Manganese | μg | 40 |
| Copper | μg | 266 |
| Iodine | μg | 80 |
| Sodium | mg | 128 |
| Potassium | mg | 520 |
| Chloride | mg | 346 |
| Selenium | μg | 11 |
| Sphingomyelin | mg | 93.8 |

The composition may also contain any additional ingredients ordinarily found in infant formula formulations.

TABLE 10a

| NUTRIENT | UNITS per Litre | Investigational Formula |
|---|---|---|
| Energy | kcal | 662.0 |
| Energy | kJ | 2768.5 |
| Water/Moisture | g | 902.6 |
| Ash | g | 3.4 |
| Protein | | |
| Protein | g | 13.4 |
| 65% Whey | g | 8.7 |
| as alpha-lactalbumin | g | 2.3 |
| 35% Casein | g | 4.7 |
| Carbohydrates | | |
| Available Carbohydrates | g | 68.6 |
| Carbohydrate | g | 73.6 |
| of which lactose | g | 68.6 |
| of which sugars | g | 68.6 |
| Soluble Dietary Fiber (as oligofructose) | g | 5.0 |
| Lipids | | |
| Total Fat | g | 36.0 |
| Fatty acids saturated | g | 14.0 |
| Trans Fatty Acids | g | 0.3 |
| Sphingomyelin | mg | 105.0 |
| Linoleic Acid | mg | 5200.0 |
| Linolenic Acid | mg | 420.5 |
| linoleic:alpha-linolenic acid ratio | ratio | 12.4 |
| ARA | mg | 132.0 |
| DHA | mg | 132.0 |
| ARA/DHA | ratio | 1.0 |
| Vitamins | | |
| Vitamin A (Retinol) | mcg RE | 660.1 |
| Beta-carotene | mcg | 150.0 |
| Vitamin D (Cholecalciferol) | mcg D | 12.0 |

TABLE 10a-continued

| NUTRIENT | UNITS per Litre | Investigational Formula |
|---|---|---|
| Vitamin E (TE) | mg | 5.8 |
| Vitamin K | mcg | 53.6 |
| Vitamin B1 (Thiamine) | mg | 0.8 |
| Vitamin B2 (Riboflavin) | mg | 0.9 |
| Vitamin B6 (Pyridoxine) | mg | 0.6 |
| Vitamin B12 (Cyanocobalamin) | mcg | 7.0 |
| Niacin | mg | 5.0 |
| Folic Acid | mcg | 219.0 |
| Pantothenic Acid | mg | 3.5 |
| Biotin | mcg | 18.0 |
| Vitamin C (Ascorbic acid) | mg | 80.0 |
| Minerals and Trace Elements | | |
| Calcium | mg | 336.7 |
| Phosphorus | mg | 190.0 |
| Ca:P | ratio | 1.8 |
| Magnesium | mg | 45.0 |
| Iron | mg | 8.6 |
| Zinc | mg | 5.5 |
| Manganese | mcg | 50.0 |
| Copper | mg | 0.3 |
| Iodine | mcg | 90.0 |
| Sodium | mg | 175.0 |
| Potassium | mg | 500.0 |
| Chloride | mg | 345.0 |
| Selenium | mcg | 13.5 |
| Other substances | | |
| Choline | mg | 160.0 |
| Inositol | mg | 45.0 |
| Taurine | mg | 37.6 |
| L-Carnitine | mg | 8.8 |
| Lutein | mg | 0.1 |
| Nucleotides (Total) | mg | 20.8 |
| CMP | mg | 10.4 |
| UMP | mg | 4.0 |
| AMP | mg | 3.2 |
| GMP | mg | 1.6 |
| IMP | mg | 1.6 |

The composition may also contain any additional ingredients ordinarily found in infant formula formulations.

Example 6

Co Culture of Neurons and OL

Neurons/Oligodendrocytes were cultured as previously described by Charles et al., 2000. Pregnant female rats of 17 days gestation were killed by cervical dislocation (Rats Wistar) and the foetuses removed from the uterus. The Forebrains were removed and placed in ice-cold medium of Leibovitz (L15) containing 2% of Penicillin-Streptomycin (PS) and 1% of bovine serum albumin (BSA). Forebrains were dissociated by trypsinisation for 20 min at 37° C. (Trypsin EDTA 1x). The reaction was stopped by the addition of Dulbecco's modified Eagle's medium (DMEM) containing DNAase I grade II (0.1 mg/ml) and 10% of foetal calf serum (FCS). Cells were then mechanically dissociated by 3 passages through a 10 ml pipette. Cells were then centrifuged at 180xg for 10 min at 4° C. temperature on a layer of BSA (3.5%) in L15 medium. The supernatant was discarded and the cells of pellet were re-suspended in DMEM containing 10% of FCS. Cells were then centrifuged at 515xg for 10 min at 4° C. The supernatant was discarded and the cells of pellet were re-suspended in a culture medium consisting of Neurobasal supplemented with 2% of B27, 2 mM of L-glutamine (L Glu), 2% of PS solution, 1% of FCS and 10 ng/ml of platelet-derived growth factor (PDGF-AA). Viable cells were counted in a Neubauer cytometer using the trypan blue exclusion test. The cells were seeded at a density of 20000 cells/well in 96 well-plates pre-coated with poly-L-lysine and laminin.

The day following seeding (day 1 of culture), cells were incubated with a test compound (selected from those listed in table 11), or estradiol. Control cells were not incubated with a test compound or estradiol. Estradiol was used as positive control. Estradiol is known to induce OPC proliferation. The positive effect of estradiol on OL differentiation has also been demonstrated, as has its effect on the early myelination process. The positive effect of estradiol on neurite outgrowth was also published (for review see Alevaro et al., 2010).

The plates were maintained at 37° C. in a humidified incubator, in an atmosphere of air (95%)-CO2 (5%). Half of the medium was replaced every other day with fresh medium and test compound or control compound. The test or control compounds were maintained at the defined concentration for the duration of the experiments. Compounds were tested on 1 culture (6 wells per conditions). Cells were then used on day 12, 18 or 30 of culture to measure one of either proliferation of OPC, differentiation of OPC into OL and early myelination process (myelin wrapping), or maturation of OL (myelin maturation) and mature myelination process (myelin wrapping).

Proliferation of OPC—Measurement of A2B5 Positive Cells and Total Axonal Length (NF)

On day 12 of culture, cells were fixed by a cold mixture of absolute ethanol (95%) and pure acetic acid (5%) for 5 min. The cells were then permeabilized and non-specific sites were blocked with a solution of phosphate buffered saline (PBS) containing 0.1% of saponin and 1% FCS for 15 min at room temperature.

Cells were then incubated with Monoclonal Anti-A2B5 conjugated Alexa Fluor® 488 produced in mouse at dilution of 1/200 in PBS containing 1% FCS, 0.1% saponin, for 2 h at room temperature and with anti-NF (Neurofilament 200 phosphorylated and non-phosphorylated) produced in rabbit at dilution of 1/500 in PBS containing 1% FCS, 0.1% saponin for 2 h at room temperature. This antibody was revealed with Alexa Fluor 568 goat anti-rabbit at the dilution of 1/400 in PBS with 1% FCS, 0.1% saponin, for 1 h at room temperature.

The total number of OPC (number of A2B5 positive cells) was quantified (to evaluate the proliferation), the axonal network was measured (total axonal length (NF)) to assess the effect of the compound on the neuronal network (the quality of the myelination is directly linked to the quality of the axonal network).

Differentiation of OPC into OL and Myelination Process (Myelin Wrapping)—Measurement of Number and Area of MAG Positive Cells, Overlap MAG/NF Wrapping, and Total Axonal Length (NF)

On day 18 of culture, cells were fixed by a cold mixture of absolute ethanol (95%) and pure acetic acid (5%) for 5 min. The cells were then permeabilized and non-specific sites were blocked with a solution of phosphate buffered saline (PBS) containing 0.1% of saponin and 1% FCS for 15 min at room temperature.

Cells were then incubated with Monoclonal Anti-MAG produced in mouse at dilution of 1/400 in PBS containing 1% FCS, 0.1% saponin, and with anti-NF (Neurofilament 200 phosphorylated and non-phosphorylated) produced in rabbit at dilution of 1/500 in PBS containing 1% FCS, 0.1% saponin for 2 h at room temperature. These antibodies were revealed with CF 488 A goat anti-mouse at the dilution of 1/800 in PBS with 1% FCS, 0.1% saponin and Alexa Fluor 568 goat anti-rabbit at the dilution of 1/800 in PBS with 1% FCS, 0.1% saponin, for 1 h at room temperature. The total number of OL was quantified (number and area of MAG positive cells) (to evaluate the differentiation process), as well as the wrapping of OPC around axons (overlap MAG/NF wrapping) (myelination process). The axonal network was measured (total axonal length (NF) to assess the effect of the compounds on the neuronal network.

Maturation of OL (Myelin Maturation)—Measurement of Number and Area of MBP Positive Cells, Overlap MBP/NF Wrapping, and Total Axonal Length (NF)

On day 30 of culture, cells were fixed by a cold mixture of absolute ethanol (95%) and pure acetic acid (5%) for 5 min. The cells were then permeabilized and non-specific sites were blocked with a solution of phosphate buffered saline (PBS) containing 0.1% of saponin and 1% FCS for 15 min at room temperature.

Cells were then incubated with Monoclonal Anti-MBP produced in mouse at dilution of 1/1000 in PBS containing 1% FCS, 0.1% saponin, and with anti-NF (Neurofilament 200 phosphorylated and non-phosphorylated) produced in rabbit at dilution of 1/500 in PBS containing 1% FCS, 0.1% saponin for 2 h at room temperature. These antibodies were revealed with CF 488 A goat anti-mouse at the dilution of 1/800 in PBS with 1% FCS, 0.1% saponin and Alexa Fluor 568 goat anti-rabbit at the dilution of 1/400 in PBS with 1% FCS, 0.1% saponin, for 1 h at room temperature. The total number of OL was assessed (number and area of MBP positive cells) (to evaluate the OL maturation) as well as the wrapping of myelin around axon (overlap MBP/NF (wrapping)). The axonal network was measured (Total axonal length (NF)) to assess the effect of the compounds on the neuronal network.

For all measurements, once the culture was done (6 wells per conditions). For each condition tested, 30 pictures (each picture representing a field) per well were taken and analyzed using ImageXpress (Molecular devices) with 20× magnification equipped with LED lamp (excitation 360/480/565 and emission 460/535/620). The 30 pictures were automatically taken and represented 80% of the total surface of the culture well.

Results were expressed in terms of cumulated mean length in µm of neurite network, or myelin sheath labeled for a given marker (MAG or MBP) per field. The overlapping area between NF and MAG or MBP was measured to evaluate the wrapping.

To assess OPC population, MAG positive cell population, MBP positive cell population, an automatic counting of number of positive cells per picture (=field) was done. The results were expressed in mean number of positive cells per field.

All the images were taken under the same conditions.

TABLE 11

| PLATE 1 (A2B5/NF) |
| --- |
| Control |
| Estradiol (150 nM) |
| DHA (0.15 µM) |
| DHA (1.5 µM) |
| Stearic acid (50 µM) |
| Stearic acid (5 µM) |
| Stearic acid (0.5 µM) |
| B12 (100 nM) |
| B12 (10 nM) |
| B12 (1 nM) |
| Folic acid (250 nM) |
| Folic acid (50 nM) |

TABLE 11-continued

| PLATE 1 (A2B5/NF) |
| --- |
| Folic acid (6 nM) |
| Choline (20 µM) |
| Iron (1 µM) |
| Iron (0.1 µM) |
| Zinc (5 µM) |
| Zinc (0.5 µM) |
| Phosphorus (5 mM) |
| Phosphorus (1 mM) |
| Magnesium (25 mM) |
| Copper (0.5 µM) |
| Phosphatidylcholine (100 µM) |
| Phosphatidylinositol (5 µM) |
| Phosphatidylinositol (50 µM) |
| Phosphatidylserine (5 µM) |
| Phosphatidylserine (10 µM) |
| Phosphatidylserine (100 µM) |
| Sphingomyelin (5 µM) |
| Sphingomyelin (25 µM) |
| Ceramide(brain extract):DPPC (1:4) |
| galactoceramides (C18:1/24:1)/(C18:1/18:0):DPPC (1:4) |
| glucoceramides (C18:1/24:1)/(C18:1/18:0):DPPC (1:4) |
| D-erythro-dihydroceramide (C24:1/18:0)/(C18:0/18:1):DPPC (1:4) |
| Ceramide-1-phosphate (C18:1/24:0):DPPC (1:4) |
| GM3:DPPC (1:4) |
| GD3:DPPC (1:4) |

Results are show in FIGS. 8 to 28

Example 7

Materials and Methods

1. Feeder Layer Preparation: Dissociation of Neonatal Cortices and Maintenance of Mixed Glial Cultures Freshly dissected brains were added to a 37° C. water bath for 3 min, then cortices were diced through a P1000 pipette tip to generate smaller fragments. 75 µL of OPC papain solution per brain were added, then tissues were incubated in a 37° C. water bath for 20 min. The tissue suspension was then additioned with mixed glial culture in order to allow inactivation of the OPC papain solution.

Tissue were subsequently triturated using a sterile flame-polished glass Pasteur pipette, then 4 mL of mixed glial culture media per brain was added. Cells were centrifuged at 1200 rpm (~300 g) for 5 min, then cells were resuspended in warm mixed glial culture media and plated into PLL-coated flask.

4 hours following plating, a full media change was performed in order to remove much of the debris caused by the trituration, and promote culture viability. After 3 days of culture, a ⅔ media change was performed, and no subsequent medium change was performed. Cells were then maintained in culture until confluency.

2. Hippocampal Neurons Preparation

Hippocampal neurons were isolated from embryonic (E18) pups of Sprague Dawley rats. Briefly, following animal sacrifice, brains were isolated, meninges removed from the medial aspect of the cerebral hemispheres, then hippocampi dissected out and kept at 4° C. until process completion.

Tissue were then incubated with 2.5% trypsin for 15 min in a water bath at 37° C., then gently washed and kept in culturing media. Hippocampal dissociation was performed by repeatedly pipetting them up and down with a functionalized sterile Pasteur pipette. Following mechanical dissociation, cells were plated at desired density in neuronal plating medium, let recover for 4 hours, then put in compete neuronal culturing medium.

3. Purification of OPCs from Mixed Glial Cultures for Establishment of OL/Hippocampal Neurons o-Cultures On Day 9 of the mixed glial culture, flasks were shaken at 50 rpm for 45 min on an orbital shaker in a 5% C02 tissue culture incubator. The purpose of this shake was to remove any loosely adherent contaminating cells from the monolayer.

Media was then changed and replaced with 4 mL of fresh mixed glial culture media supplemented with 5 μg/mL insulin. Flasks were then repositioned onto the shaker, equilibrated for approximately 3 hours, then shaken for approximately 16 hours at 220 rpm (overnight).

The next morning, mixed glia culture medium containing microglia and OPCs cells were collected and pre-plated on P100 petri dish (not treated for culture) for 30 minutes in order to purify OPCs cells; microglia cells start immediately to adhere to petri while OPCs cells remained in the surnatant medium.

After 30 minutes of pre-plate, medium was collected and OLs were counted and seeded on hippocampal neurons in a final volume of 1 mL OL media.

A full OL media (minus CNTF) change was performed, then cells were maintained in culture until the appropriate experimental timings.

For maturation experiments, the experimental procedure was as follows:
 a. Growth of OPCs on feeder layer of astrocytes for 10 DIV
 b. Isolation of OPCs (Day 0)
 c. Administration of compounds (Day 3)
 d. Quantitative evaluation of maturation at Day 4, 7 and 10.

For myelination experiments, the experimental procedure was as follows:
 a. Growth of hippocampal neurons until complete neuronal network maturation (14 DIV)
 b. Concomitant growth of OPCs on feeder layer of astrocytes for 10 DIV
 c. Isolation of OPCs and coculturing with neurons (Day 14)
 d. Administration of compounds (Day 15)
 e. Quantitative evaluation of myelination at Day 15 (1 day after coculture plating, before compound treatment), 18, 21/23 and 28/29 of coculturing.

4. Acquisition of Images

All cultures at the different experimental time points, were fixed in 4% paraformaldehyde and 4% sucrose at room temperature (RT) for 10 min. Primary and secondary antibodies were applied in GDB buffer (30 mM phosphate buffer, pH 7.4, containing 0.2% gelatin, 0.5% Triton X-100, and 0.8 M NaCl) for 2 h at room temperature. cells were stained with appropriate marker (primary antibody used: Anti-A2B5 antibody (ABCAM cat. ab53521), Rat anti MBP (BIO-RAD cat. aa82-87), Oligodendrocyte Marker O4 Antibody (R&D Systems cat. MAB1326), Anti-βIII Tubulin mAb (Promega cat. G7121); secondary antibody used: Alexa anti rat 555 (Life Tech A-21434), Alexa anti mouse 488 (Life Tech A-11009). Following immunocytochemical staining all images were acquired with Array Scan XTI (ThermoScientific); the objective was 20× at binning 2×2. For each condition and replica well (triplicate) a minimum of 15 images were taken.

For the analysis of all acquired images the HCS Studio Cell Analysis Software was used, in particular the "Scan" application.

OPC Papain Solution (Made Up in MEM)
Papain solution 1.54 mg/mL
L-cysteine 360 μg/mL
DNase I 60 μg/mL
Mixed Glial Culture Media (Made Up in DMEM)
FBS 10%
Pen/Strep (0.33% from stock) 33 units/mL Penicillin and 33 pig/mL Streptomycin
GlutaMAX 1%
OL media
DMEM
100× OL-Supplement
Bovine insulin (from 1 mg/mL stock)
GlutaMAX
Holo-transferrin (from 33 mg/mL stock)
B27 Supplement
FBS
CNTF (from 50 ng/μL stock)

Results are show in FIGS. 30 to 49.

The invention claimed is:

1. A method to promote, support or optimize de novo myelination including de novo myelination trajectory, and/or brain structure, and/or brain connectivity, and/or intellectual potential and/or cognitive potential and/or learning potential and/or cognitive functioning in a formula fed infant up to 12 months of age in need thereof, the method comprising administering a synthetic nutritional composition comprising choline to the formula fed infant up to 12 months of age,
  wherein the synthetic nutritional composition comprises the choline in an amount greater than 30 mg/100 g dry weight of the synthetic nutritional composition,
  the brain structure refers to an amount and/or spatial distribution of myelinated matter throughout the brain and/or in specific brain regions, and the cognitive functioning is optimized if scores of the formula fed infant up to 12 months of age in a standardized neurodevelopmental test are less than one standard deviation different from that of an exclusively breastfed infant up to 12 months of age of a well-nourished mother, and
  the synthetic nutritional composition further comprises iron; a fatty acid derivative comprising at least one of docosahexaenoic acid or arachidonic acid; and a phospholipid selected from the group consisting of phosphatidylcholine, phosphatidylinositole, phosphatidylserine, phosphatidylethanolamine, and sphingomyelin, and mixtures thereof.

2. The method according to claim 1, wherein the formula fed infant up to 12 months of age is a human infant.

3. The method according to claim 1, wherein the synthetic nutritional composition comprises the choline in an amount of 170-300 mg/100 g dry weight of the synthetic nutritional composition.

4. The method according to claim 1, wherein the synthetic nutritional composition further comprises a vitamin.

5. The method according to claim 4, wherein the vitamin is at least one of folic acid or vitamin B12.

6. The method according to claim 1, wherein if the synthetic nutritional composition comprises iron, the iron is in an amount greater than 5 mg/100 g dry weight of the synthetic nutritional composition; if the synthetic nutritional composition comprises folic acid, the folic acid is in an amount greater than 100 mcg/100 g dry weight of the synthetic nutritional composition; if the synthetic nutritional composition comprises vitamin B12, the vitamin B12 is in an amount greater than 5 mcg/100 g dry weight of the synthetic nutritional composition; if the synthetic nutritional composition comprises sphingomyelin, the sphingomyelin is in an amount greater than 300 mg/kg dry weight of the synthetic nutritional composition; if the synthetic nutritional composition comprises a fatty acid derivative comprising DHA, the fatty acid derivative comprising DHA is in an amount of 60 to 350 mg/100 g dry weight of the synthetic nutritional composition; and if the synthetic nutritional composition comprises a fatty acid derivative comprising arachidonic acid, the fatty acid derivative comprising arachidonic acid is in an amount of 60 to 350 mg/100 g dry weight of the synthetic nutritional composition.

7. The method according to claim 1, wherein the synthetic nutritional composition is a composition selected from the group consisting of an infant formula, a composition for infants that is intended to be added or diluted with human breast milk, and a food stuff intended for consumption by an infant either alone or in combination with human breast milk.

8. The method according to claim 1, wherein the synthetic nutritional composition further comprises 60 to 350 mg of a fatty acid derivative comprising DHA/100 g dry weight of the synthetic nutritional composition.

9. The method according to claim 1, wherein the synthetic nutritional composition comprises about 2 to 6 g protein/100 kcal of the synthetic nutritional composition.

* * * * *